US006455507B1

(12) United States Patent
Drach et al.

(10) Patent No.: US 6,455,507 B1
(45) Date of Patent: *Sep. 24, 2002

(54) BENZIMIDAZOLE DERIVATIVES

(75) Inventors: John Charles Drach; Leroy B. Townsend, both of Ann Arbor, MI (US); Frank Leslie Boyd, Jr., Raleigh, NC (US); Stanley Dawes Chamberlain, Research Triangle Park, NC (US); Susan Mary Daluge, Research Triangle Park, NC (US); David Norman Deaton, Research Triangle Park, NC (US); Marc W. Andersen, Raleigh, NC (US); George Andrew Freeman, Research Triangle Park, NC (US)

(73) Assignee: SmithKline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/424,934

(22) PCT Filed: Jun. 8, 1998

(86) PCT No.: PCT/EP98/03380

§ 371 (c)(1),
(2), (4) Date: Mar. 17, 2000

(87) PCT Pub. No.: WO98/56761

PCT Pub. Date: Dec. 17, 1998

(30) Foreign Application Priority Data

Jun. 10, 1997 (GB) ............................................. 9711982
Jul. 11, 1997 (GB) ............................................. 9714552

(51) Int. Cl.$^7$ ........................ A61K 31/70; C07H 17/02; C07D 209/04
(52) U.S. Cl. ............................ 514/43; 514/42; 514/45; 514/46; 514/248; 514/249; 514/252; 514/254; 536/4.1; 536/17.2; 536/17.3; 548/469
(58) Field of Search .................................. 536/4.1, 17.2, 536/17.3; 514/42, 43, 45, 46, 248, 249, 252, 254; 548/469

(56) References Cited

U.S. PATENT DOCUMENTS

| 3,655,901 A | 4/1972 | Jensen |
| 3,839,575 A | 10/1974 | Gauss |
| 4,361,563 A | 11/1982 | Austel et al. |
| 5,248,672 A | 9/1993 | Townsend |
| 5,399,580 A | 3/1995 | Daluge |
| 5,534,535 A | 7/1996 | Townsend |
| 5,574,058 A | 11/1996 | Townsend |
| 5,631,259 A | 5/1997 | Jähne et al. |

FOREIGN PATENT DOCUMENTS

| EP | 0008391 A | 3/1980 |
| EP | A 0 304624 | 3/1989 |
| EP | 0 350 467 | 1/1990 |
| EP | 0 515 156 | 11/1992 |
| EP | 0521463 A | 1/1993 |
| FR | 1476350 | 2/1967 |
| FR | 1491244 | 7/1967 |
| WO | WO 92/07867 | 5/1992 |
| WO | Wo9207867 A | 5/1992 |
| WO | 93/18009 | 9/1993 |
| WO | WO94/08456 | 4/1994 |
| WO | WO96/01833 | 1/1996 |

OTHER PUBLICATIONS

Gosselin et al., "Synthesis and biological evaluation of new 5,6–dichlorobenzimidazole nucleoside derivatives," Antiviral Chem. Chemotherapy, vol. 5, pp. 243–256 (1994).

Revankar et al., The synthesis of 2–chloro–1–(β–D–ribofuranosyl)benzimidazole and certain related derivatives (1), J. Heterocycles, vol. 5, pp. 477–483 (1968).

Revankar et al., The synthesis of 2–chloro–1–βD–ribofuranosyl–5,6–dimethylbenzimidazole and certain related derivatives (1), J. Heterocycles, vol. 5, No. 4, pp. 615–620 (1968).

Gordon et al., "Kinetics of Decay in the Expression of Interferon–Dependent mRNAs Responsible for Resistance to Virus," Proc. Natl Acad. Sci. USA, 77(1) pp. 452–456 (1980).

Devivar et al., "Benzimidazole Ribonucleosides: Observation of an Unexpected Nitration When Performing Non–Aqueous Diazotizations with t–butyl Nitrite," Biorganic & Medicinal Chem. Letters, 2(9), pp. 1105–1110 (Sep. 1992).

Tigges et a., "Human CDB+ Herpes Simplex Virus–Specific Cytotoxic T–Lymphocyte Clones Recognize Diverse Viron Protein Antigens," J. Virology, 66(3), pp. 1622–1634 (1992).

Antaki, P.; J. Chem. Soc., 1951, pp. 2873–2877, "Some glycosylbenziminazoles".

Simonov A. M. and Pozharskii A. F.; Journal of General Chemistry of the USSR, vol. 33, 1963, pp. 2289–2293, "Investigations in the field of benzimidazole . . . ".

Phillips Et Al.; Tetrahedron Letters, vol. 37 No. 7/96, pp. 4887–4890, "Solid Phase Synthesis of Benzimidazoles".

Yaping Et Al; Tetrahedron Letters, vol. 39, No. 20, 5/98, pp. 3121–3124, "Remarkably Selective Palladium–Catalyzed. . . ".

Primary Examiner—James O. Wilson
(74) Attorney, Agent, or Firm—Nixon & Vanderhye

(57) ABSTRACT

Benzimidazole derivatives useful for treating or preventing viral infections such as those caused by herpes viruses or in the treatment of restenosis following surgical techniques. Methods of preparing these benzimidazole derivatives and pharmaceutical compositions containing them are described.

29 Claims, No Drawings

BENZIMIDAZOLE DERIVATIVES

FIELD OF THE INVENTION

The present invention relates to certain benzimidazole derivatives and their use in medical therapy particularly for the treatment or prophylaxis of virus infections such as those caused by herpes viruses. The invention also relates to the preparation of the benzimidazole derivatives and pharmaceutical formulations containing them.

BACKGROUND OF THE INVENTION

Of the DNA viruses, those of the herpes group are the source of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6) and human herpes virus type 7 (HHV-7) and type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

HSV infection is often characterized by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal. VZV is a herpes virus which causes chickenpox and shingles. Chickenpox is the primary disease produced in a host without immunity, and in young children is usually a mild illness characterized by a vesicular rash and fever. Shingles or zoster is the recurrent form of the disease which occurs in adults who were previously infected with VZV. The clinical manifestations of shingles are characterized by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital HCMV disease is characterized by jaundice, hepatosplenomegaly, petechial rash and multiple organ dysfunction and is associated with long-term sequelae such as hearing loss and mental deficiency. Infection can result in retinitis leading to blindness or, in less severe forms, failure to thrive, and susceptibility to chest and ear infections. CMV infection in patients whose immune systems are immature or who are immunocompromised for example as a result of malignancy, treatment with immunosuppressive drugs following transplantation or infection with Human Immunodeficiency Virus, may give rise to retinitis, colitis, esophagistis, hepatitis, meningoencephalitis, pneumonitis, gastrointestinal disorders and neurological diseases. In addition, these CMV disease syndromes can affect patients who are not immunocompromised.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumors, Hodgkin's disease, nasopharyngeal carcinoma, Burkitt lymphoma, non-Hodgkin B-cell lymphoma, thymomas and oral hairy leukoplakia. EBV infections have also been found in association with a variety of epithelial-cell-derived tumors of the upper and lower respiratory tracts including the lung.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease etiology. HHV-8 has been implicated in cancer.

Hepatitis B virus (HBV) is a viral pathogen of world-wide major importance. The virus is etiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

GB 682,960, GB 690,119 and GB 696,952 disclose benzimidazole glycosides useful as intermediates in the preparation of therapeutic substances. Mochalin et. al. (SU 443035; Zh. Org. Khim. 12(1), 58–63 (1976)) describe the synthesis of certain unsubstituted benzimidazote pyranosides. Gosselin et. al. (*Antiviral Chem. Chemother.* 5(4), 243–56, 1994) disclose certain 5,6,-dichlorobenzimidazole arabinopyranosyl compounds with antiviral activity. Townsend et. al. (*Chemical Reviews*, vol. 70 no. 3, 1970) discloses certain 1-glycosylbenzimidazoles. U.S. Pat. No. 5,585,394 discloses 1-benzenesulfonyl-1,3-dihyro-2H-benzimidazol-2-one derivatives which have affinity for the vasopressin and oxytocin receptors. EP 0 521 463 A2 describes certain cyclohexanol analogues for antiviral and anti-parasitic use.

DETAILED DESCRIPTION OF THE INVENTION

It has now been discovered that certain 6-membered ring-containing benzimidazole derivatives are useful for the treatment or prophylaxis of viral infections. According to a first aspect of the present invention, there is provided compounds of formula (I)

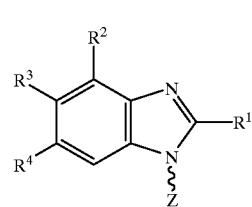

(I)

wherein:

$R^1$ is halogen, hydroxy, azido, $C_{1-8}$alkyl, $C_{1-8}$alkoxy, $C_{2-6}$alkenyl, $C_{2-6}$alkynyl, $C_{6-14}$aryl$C_{2-6}$alkenyl, $C_{6-14}$aryl$C_{2-6}$alkynyl, or —NR$^{19}$R$^{20}$ (where R$^{19}$ and R$^{20}$ may be the same or different and are hydrogen, $C_{1-8}$alkyl, cyano$C_{1-8}$alkyl, hydroxy$C_{1-8}$alkyl, halo$C_{1-}$ salkyl, $C_{3-7}$cycloalkyl, $C_{1-8}$alkyl$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-8}$alkyl, heterocycle$C_{1-8}$alkyl, $C_{1-8}$alkylcarbonyl, $C_{6-14}$arylsulfonyl, or $R^{19}R^{20}$ together with the N atom to which they are attached form a 3, 4, 5 or 6 membered heterocyclic ring), $OR^{21}$ (where $R^{21}$ is hydrogen, $C_{1-8}$alkyl, $C_{3-7}$cycloalkyl, or $C_{6-14}$aryl), or $SR^{22}$ (where $R^{22}$ is hydrogen, $C_{1-8}$alkyl, hydroxy$C_{1-8}$alkyl, $C_{3-7}$cycloalkyl, or $C_{6-14}$aryl);

$R^2$ is hydrogen or halogen;

$R^3$ and $R^4$ may be the same or different and are hydrogen, halogen, $C_{1-8}$alkyl, $C_{6-14}$aryl, heterocycle$C_{6-14}$aryl, $C_{1-8}$alkoxy, halo$C_{1-8}$alkyl or $-SR^{24}$ (where $R^{24}$ is hydrogen, $C_{1-8}$alkyl, $C_{6-14}$aryl, or $C_{6-14}$aryl$C_{1-8}$alkyl);

Z is a substituent of formula (Ia), (Ib), or (Ic)

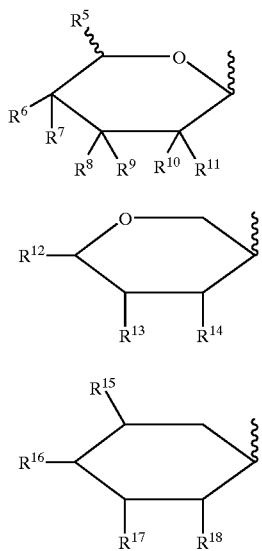

wherein:

$R^5$ is hydrogen, $C_{1-8}$alkyl, halo$C_{1-8}$alkyl or $C_{1-8}$alkoxy;

$R^6$ is hydrogen, hydroxy, halogen, $C_{1-8}$alkyl, hydroxy$C_{1-8}$alkyl, halo$C_{1-8}$alkyl or $C_{1-8}$alkoxy;

$R^7$ is hydrogen, hydroxy, halogen, $C_{1-8}$alkyl, hydroxy$C_{1-8}$alkyl, halo$C_{1-8}$alkyl, $C_{1-8}$alkoxy, or $R^6$ and $R^7$ together form a ketone or alkene;

$R^8-R^{11}$ may be the same or different and are hydrogen, hydroxy, halogen, $C_{2-8}$alkyl, hydroxy$C_{1-8}$alkyl, halo$C_{1-8}$alkyl, $C_{1-8}$alkoxy, or any of $R^8$ and $R^9$ or $R^{10}$ and $R^{11}$ together form a ketone or alkene;

$R^{12}-R^{18}$ may be the same or different and are hydrogen, hydroxy, $C_{1-8}$alkyl or hydroxy$C_{1-8}$alkyl;

or a pharmaceutically acceptable derivative thereof, provided that a compound of formula (I) cannot be 2,5-dimethyl-1-(2,3,4-tri-O-acetyl-beta-D-xylopyranosyl)-1H-benzimidazole or 5,6-dimethyl-1-(2,3,4-tri-O-acetyl-beta-D-arabinopyranosyl)-benzimidazole-2-thione;

further provided that when Z is a substituent of formula (Ia):
 a) $R^2$, $R^3$, and $R^4$ cannot all be hydrogen; and
 b) $R^1$ cannot be $NR^{19}R^{20}$ where $R^{19}$ and $R^{20}$ together with the N atom to which they are attached form a 5 membered heterocyclic ring containing S;

further provided that when Z is a substituent of formula (Ib):
 a) $R^1$ cannot be $NR^{19}R^{20}$ where $R^{19}$ and $R^{20}$ together with the N atom to which they are attached form a 5 membered heterocyclic ring containing S; and further provided that when Z is a substituent of formula (Ic):
 a) and when $R^{15}-R^{18}$ are all hydrogen, then $R^1$ cannot be hydroxy, amino or $SR^{22}$ where $R^{22}$ is H; and
 b) $R^1$ cannot be $NR^{19}R^{20}$ where $R^{19}$ and $R^{20}$ together with the N atom to which they are attached form a 5 membered heterocyclic ring containing S.

Particularly preferred $R^1$ groups include halogen and $-NR^{19}R^{20}$ where $R^{19}$ is hydrogen and $R^{20}$ is $C_{1-8}$alkyl (particularly $C_{1-3}$alkyl, with isopropyl being especially preferred), $C_{3-7}$cycloalkyl (cyclopropyl is especially preferred), $C_{1-8}$alkyl$C_{3-7}$cycloalkyl or $C_{3-7}$cycloalkyl$C_{1-8}$alkyl.

In certain particularly preferred compounds, $R^2$ is hydrogen.

Particularly preferred $R^3$ and $R^4$ groups include hydrogen, halogen (chlorine is especially preferred), and $C_{1-8}$alkoxy, (particularly $C_{1-3}$alkoxy, with methoxy being especially preferred). In certain particularly preferred compounds, one or both of $R^3$ and $R^4$ are chlorine, desirably both.

In certain especially preferred compounds, $R^5$ is hydrogen.

Particularly preferred substituents at $R^{6-18}$ include hydrogen, hydroxy, $C_{1-8}$alkyl (particularly $C_{1-3}$alkyl, with methyl and ethyl being especially preferred) and hydroxy$C_{1-8}$alkyl (particularly hydroxy$C_{1-3}$alkyl, with hydroxymethyl being especially preferred).

Preferred compounds of formula (I) are compounds wherein Z is substituent of formula (Ia).

Other preferred compounds of formula (I) are compounds wherein Z is a substituent of formula (Ib).

In a further aspect of the present invention, there is provided compounds of formula (II)

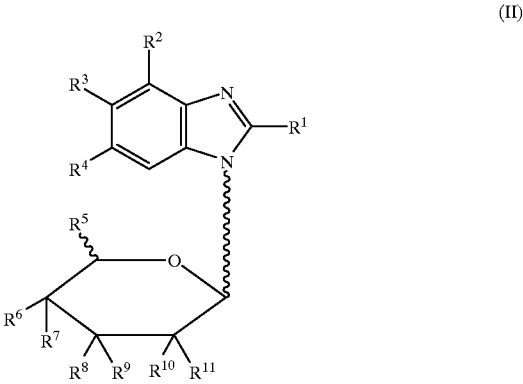

wherein:

$R^1$ is halogen, hydroxy, azido, $C_{1-8}$alkyl, $C_{1-8}$alkoxy, $C_{2-6}$alkenyl, $C_{2-6}$alkynyl, $C_{6-14}$aryl$C_{2-6}$alkenyl, $C_{6-14}$aryl$C_{2-6}$alkynyl, or $-NR^{19}R^{20}$ (where $R^{19}$ and $R^{20}$ may be the same or different and are hydrogen, $C_{18}$alkyl, cyano$C_{1-8}$ alkyl, hydroxy$C_{1-8}$alkyl, halo$C_{1-8}$alkyl, $C_{3-7}$cycloalkyl, $C_{1-8}$alkyl$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-6}$alkyl, heterocycle$C_{1-8}$alkyl, $C_{1-8}$alkylcarbonyl, $C_{6-14}$arylsulfonyl, or $R^{19}R^{20}$ together with the N atom to which they are attached form a 3, 4, 5 or 6 membered heterocyclic ring), $OR^{21}$ (where $R^{21}$ is hydrogen, $C_{1-8}$alkyl, $C_{3-7}$cycloalkyl, or $C_{6-14}$aryl), or $SR^{22}$ (where $R^{22}$ is hydrogen, $C_{1-8}$alkyl, hydroxy$C_{1-8}$alkyl, $C_{3-7}$cycloalkyl, or $C_{6-14}$aryl);

$R^2$ is hydrogen or halogen;

$R^3$ and $R^4$ may be the same or different and are hydrogen, halogen, $C_{1-8}$alkyl, $C_{6-14}$aryl, heterocycle$C_{6-14}$aryl, $C_{1-8}$alkoxy, halo$C_{1-8}$alkyl or —$SR^{24}$ (where $R^{24}$ is hydrogen, $C_{1-8}$alkyl, $C_{6-14}$aryl, or $C_{6-14}$aryl$C_{1-8}$alkyl);

$R^5$ is hydrogen, $C_{1-8}$alkyl, halo$C_{1-8}$alkyl, $C_{1-8}$alkoxy;

$R^6$ is hydrogen, hydroxy, halogen, $C_{1-8}$alkyl, hydroxy$C_{1-8}$alkyl, halo$C_{1-8}$alkyl, $C_{1-8}$alkoxy;

$R^7$ is hydrogen, hydroxy, halogen, $C_{1-8}$alkyl, hydroxy$C_{1-8}$alkyl, halo$C_{1-8}$alkyl, $C_{1-8}$alkoxy, or $R^6$ and $R^7$ together form a ketone or alkene;

$R^8$–$R^{11}$ may be the same or different and are hydrogen, hydroxy, halogen, $C_{2-8}$alkyl, hydroxy$C_{1-8}$alkyl, halo$C_{1-8}$alkyl, $C_{1-8}$alkoxy, or any of $R^8$ and $R^9$ or $R^{10}$ and $R^{11}$ together form a ketone or alkene;

or a pharmaceutically acceptable derivative thereof, provided that a compound of formula (I) cannot be 2,5-dimethyl-1-(2,3,4-tri-O-acetyl-beta-D-xylopyranosyl)-1H-benzimidazole or 5,6-dimethyl-1-(2,3,4-tri-O-acetyl-beta-D-arabinopyranosyl)-benzimidazole-2-thione;

further provided that when Z is a substituent of formula (Ia):
a) $R^2$, $R^3$, and $R^4$ cannot all be hydrogen; and
b) $R^1$ cannot be $NR^{19}R^{20}$ where $R^{19}$ and $R^{20}$ together with the N atom to which they are attached form a 5 membered heterocyclic ring containing S.

A preferred embodiment of the present invention are compounds of formula (III)

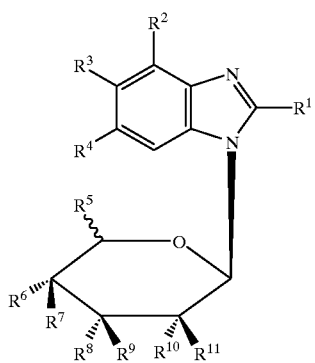

(III)

wherein:
$R^1$ is halogen, hydroxy, azido, $C_{1-8}$alkyl, $C_{1-8}$alkoxy, $C_{2-6}$alkenyl, $C_{2-6}$alkynyl, $C_{6-14}$aryl$C_{2-6}$alkenyl, $C_{6-14}$aryl$C_{2-6}$alkynyl, or —$NR^{19}R^{20}$ (where $R^{19}$ and $R^{20}$ may be the same or different and are hydrogen, $C_{1-8}$alkyl, cyano$C_{1-8}$alkyl, hydroxy$C_{1-8}$alkyl, halo$C_{1-8}$alkyl, $C_{3-7}$cycloalkyl, $C_{1-8}$alkyl$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-6}$alkyl, heterocycle$C_{1-8}$alkyl, $C_{1-8}$alkylcarbonyl, $C_{6-14}$arylsufonyl, or $R^{19}R^{20}$ together with the N atom to which they are attached form a 3, 4, 5 or 6 membered heterocyclic ring), $OR^{21}$ (where $R^{21}$ is hydrogen, $C_{1-8}$alkyl, $C_{3-7}$cycloalkyl, or $C_{6-14}$aryl), or $SR^{22}$ (where $R^{22}$ is hydrogen, $C_{1-8}$alkyl, hydroxy$C_{1-8}$alkyl, $C_{3-7}$cycloalkyl, or $C_{6-14}$aryl);

$R^2$ is hydrogen or halogen;

$R^3$ and $R^4$ may be the same or different and are hydrogen, halogen, $C_{1-8}$alkyl, $C_{6-14}$aryl, heterocycle$C_{6-14}$aryl, $C_{1-8}$alkoxy, halo$C_{1-8}$alkyl or —$SR^{24}$ (where $R^{24}$ is hydrogen, $C_{1-8}$alkyl, $C_{6-14}$aryl, or $C_{6-14}$aryl$C_{1-8}$alkyl);

$R^5$ is hydrogen, $C_{1-8}$alkyl, halo$C_{1-8}$alkyl, $C_{1-8}$alkoxy;

$R^6$ is hydrogen, hydroxy, halogen, $C_{1-8}$alkyl, hydroxy$C_{1-8}$alkyl, halo$C_{1-8}$alkyl, $C_{1-8}$alkoxy;

$R^7$ is hydrogen, hydroxy, halogen, $C_{1-8}$alkyl, hydroxy$C_{1-8}$alkyl, halo$C_{1-8}$alkyl, $C_{1-8}$alkoxy, or $R^6$ and $R^7$ together form a ketone or alkene;

$R^8$ –$R^{11}$ may be the same or different and are hydrogen, hydroxy, halogen, $C_{2-8}$alkyl, hydroxy$C_{1-8}$alkyl, halo$C_{1-8}$alkyl, $C_{1-8}$alkoxy, or any of $R^8$ and $R^9$ or $R^{10}$ and $R^{11}$ together form a ketone or alkene;

or a pharmaceutically acceptable derivative thereof, provided that a compound of formula (I) cannot be 2,5-dimethyl-1-(2,3,4-tri-O-acetyl-beta-D-xylopyranosyl)-1H-benzimidazole or 5,6-dimethyl-1-(2,3,4-tri-O-acetyl-beta-D-arabinopyranosyl)-benzimidazole-2-thione;

further provided that when Z is a substituent of formula (Ia):
a) $R^2$, $R^3$, and $R^4$ cannot all be hydrogen; and
b) $R^1$ cannot be $NR^{19}R^{20}$ where $R^{19}$ and $R^{20}$ together with the N atom to which they are attached form a 5 membered heterocyclic ring containing S.

Compounds of formula (I) in which Z is a substituent of formula (Ic) provide a further aspect of the invention.

Preferred compounds of formula (I), (II), and (III) are those wherein:
$R^1$ is halogen;
$R^2$ is hydrogen;
$R^3$ and $R^4$ are halogen;
$R^5$ and $R^7$ are hydrogen;
$R^6$ is hydroxy or hydrogen;
$R^8$ and $R^{10}$ are hydroxy;
$R^9$ and $R^{11}$ are hydrogen;
$R^{12}$ is hydrogen, $C_{1-8}$alkyl, or hydroxy$C_{1-8}$alkyl;
$R^{13}$ is hydroxy;
$R^{14}$–$R^{18}$ may be the same or different and are hydrogen or hydroxy;
or a pharmaceutically acceptable derivative thereof.

A preferred compound of Formula (III) is 2-bromo-5,6-dichloro-1-β-D-ribopyranosyl-1H-benzimidazole, represented by formula (XI):

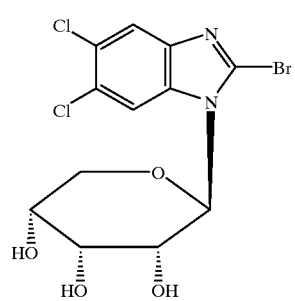

(XI)

The compounds of formula (I) including compounds of formula (II) and (III) above and their pharmaceutically acceptable derivatives are hereinafter referred to as the compounds according to the invention.

The compounds according to the invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

The present invention includes within its scope each possible alpha and beta anomer of the compounds of formula (I) and their physiologically functional derivatives, substantially free of the other anomer, that is to say no more than about 5% w/w of the other anomer.

Compounds of formula (I) in the beta anomeric form are preferred.

Preferred compounds of the present invention include:
(3S,4R,5R,6S)-2-Bromo-5,6-dichloro-1-(tetrahydro4,5-dihydroxy-6-(hydroxymethyl)-2H-pyran-3-yl)-1H-benzimidazole;
(±)-Trans-2-(2-bromo-5,6-dichloro-1H-benzimidazol-1-yl)cyclohexanol;
(±)-(1R*, 2S*, 3R*)-3-(2-Bromo-5,6-dichloro-1H-benzimidazol-1-yl)-1,2-cyclohexanediol;
2-bromo-5,6-dichloro-1-β-D-ribopyranosyl-1H-benzimidazole;
5,6-dichloro-N-(1-methylethyl)-1-β-D-ribopyranosyl-1H-benzimidazol-2-amine;
2-bromo-5,6-dichloro-4-fluoro-1-β-D-ribopyranosyl-1H-benzimidazole;
2-bromo-5,6,-dichloro-1-(2,3,4-tri-O-acetyl-β-D-ribopyranosyl)-1H-benzimidazole;
2-bromo-5,6-dichloro-1-β-L-ribopyranosyl-1H-benzimidazole;
2-bromo-6-chloro-5-methyl-1-β-D-ribopyranosyl-1H-benzimidazole; and
2-bromo-5,6,-dichloro-1-(4-deoxy-β-D-erythro-pentopyranosyl)-1H-benzimidazole;
2-Bromo-5,6-dichloro-1-(beta-L-ribopyranosyl)-1H-benzimidazole;
2-Bromo-5,6-dichloro-1-(beta-L-xylopyranosyl)-1H-benzimidazole;
2-Bromo-5,6-dichloro-1-(2-deoxy-alpha-D-erythro-pentopyranosyl)-1H-benzimidazole;
or pharmaceutically acceptable derivatives thereof.

The term "alkyl", alone or in combination with any other term, refers to a straight-chain or branch-chain saturated aliphatic hydrocarbon radical containing the specified number of carbon atoms, or where no number is specified, preferably from 1–10 and more preferably from 1–6 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like, with methyl and ethyl being preferred.

The term "alkenyl," alone or in combination with any other term, refers to a straight-chain or branched-chain mono-or poly-unsaturated aliphatic hydrocarbon radical containing the specified number of carbon atoms, or where no number is specified, preferably from 2–10 carbon atoms and more preferably, from 2–6 carbon atoms. References to alkenyl groups include groups which may be in the E- or Z-form or a mixture thereof and which when they contain at least three carbon atoms, may be branched. Examples of alkenyl radicals include, but are not limited to, ethenyl, E- and Z-propenyl, isopropenyl, E- and Z-butenyl, E- and Z-isobutyenyl, E- and Z-pentenyl, E- and Z-hexenyl, E,E-, E,Z-, Z, E- and Z,Z-hexadienyl and the like.

The term "alkynyl" refers to hydrocarbon groups of either a straight or branched configuration with one or more carbon-carbon triple bonds which may occur in any stable point along the chain, such as ethynyl, propynyl, butynyl, pentynyl, and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like, with methoxy being preferred.

Alkenyl and alkynyl substituents may optionally contain one or more heteroatoms such as nitrogen, sulfur, or oxygen.

The term "aryl," alone or in combination with any other term, refers to a carbocyclic aromatic radical (such as phenyl or naphthyl) containing the specified number of carbon atoms, preferably from 6–14 carbon atoms, and more preferably from 6–10 carbon atoms, optionally substituted with one or more substituents selected from C1–6 alkoxy, (for example methoxy), nitro, halogen, (for example chloro), amino, carboxylate and hydroxy. Examples of aryl radicals include, but are not limited to phenyl, naphthyl, indenyl, indanyl, azulenyl, fluorenyl, anthracenyl and the like.

The term "heterocycle" and "heterocyclic" radical, unless otherwise defined herein, refers to a stable 3–7 membered monocyclic heterocyclic ring or 8–11 membered bicyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom which results in the creation of a stable structure. Preferred heterocycles include 5–7 membered monocyclic heterocycles and 8–10 membered bicyclic heterocycles. Examples of such groups include imidazolyl, imidazolinoyl, imidazolidinyl, quinolyl, isoqinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, benzoxazolyl, oxopiperidinyl, oxopyrrolidinyl, oxoazopinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyranofuranyl.

Preferred heterocycles include imadazolyl, pyrrolyl, pyrrolinyl, piperidinyl, piperazinyl, and morpholinyl.

The term "halogen" refers to a radical of fluorine, chlorine, bromine or iodine.

The term "haloC$_{1-8}$ alkyl" means a C$_{1-8}$alkyl group in which one or more hydrogens is replaced by halo and preferably containing one, two or three halo groups. Examples of such groups include trifluoromethyl and fluoroisopropyl.

The term "pharmaceutically effective amount" refers to an amount effective in treating a virus infection, for example a CMV or HBV infection, in a patient either as monotherapy or in combination with other agents. The term "treating" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylactically effective amount" refers to an amount effective in preventing a virus infection, for example a CMV or HBV infection, or preventing the occurrence of symptoms of such an infection, in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the antiviral agent.

As used herein, the compounds according to the invention are defined to include pharmaceutically acceptable derivatives or prodrugs thereof. A "pharmaceutically acceptable derivative" or "pharmaceutically acceptable prodrug" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

The compounds according to the invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate; cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectianate, persulfate, phenylproprionate, picrate, pivalate, propionate, succinate, tartrate, thiocyanate, tosylate and undecanoate.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-P-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium and N—W+4 (wherein W is $C_{1-4}$ alkyl). Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids Physiologically acceptable salts of a compound with a hydroxy group include the anion of said compound in combination with a suitable cation such as $Na^+$, $NH_4^+$, and $NW_4^+$ (wherein W is a $C_{1-4}$alkyl group).

Pharmaceutically acceptable salts include salts of organic carboxylic acids such as ascorbic, acetic, citric, lactic, tartaric, malic, maleic, isothionic, lactobionic, p-aminobenzoic and succinic acids; organic sulphonic acids such as methanesulphonic, ethanesulphonic, benzenesulphonic and p-toluenesulphonic acids and inorganic acids such as hydrochloric, sulphuric, phosphoric, sulphamic and pyrophosphoric acids.

For therapeutic use, salts of the compounds according to the invention will be pharmaceutically acceptable. However, salts of acids and bases which are non-pharmaceutically acceptable may also find use, for example, in the preparation or purification of a pharmaceutically acceptable compound.

Preferred salts include salts formed from hydrochloric, sulfuric, acetic, succinic, citric and ascorbic acids.

Preferred esters of the compounds according to the invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

In such esters, unless otherwise specified, any -alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

Preferred carboxylic acid esters of compounds according to the invention include the acetate, butyrate and valerate esters. L-valyl is a particularly preferred amino acid ester.

Any reference to any of the above compounds also includes a reference to a pharmaceutically acceptable salts thereof.

In a further aspect of the invention there are provided the compounds according to the invention for use in medical therapy particularly for the treatment or prophylaxis of viral infections such as herpes viral infections. Compounds according to the invention have been shown to be active against CMV infections, although early results suggest that these compounds could also be active against other herpes virus infections such as HSV-1 and -2, HHV 6, 7, and 8, VZV, EBV as well as against HBV infections.

Other viral conditions which may be treated in accordance with the invention have been discussed in the introduction hereinbefore. The compounds according to the invention are particularly suited to the treatment or prophylaxis of CMV infections and associated conditions. Examples of CMV conditions which may be treated in accordance with the invention have been discussed in the introduction hereinbefore.

According to another aspect, the present invention provides a method for the treatment or prevention of the symptoms or effects of a viral infection in an infected animal, for example, a mammal including a human, which comprises treating said animal with a therapeutically effective amount of a compound according to the invention. According to a particular embodiment of this aspect of the invention, the viral infection is a herpes virus infection, such as CMV, HSV-1, HSV-2, VZV, EBV, HHV-6, HHV-or HHV-8. A further aspect of the invention includes a method for the treatment or prevention of the symptoms or effects of an HBV infection.

The compounds according to the invention may also be used in adjuvant therapy in the treatment of HIV infections or HIV-associated symptoms or effects, for example Kaposi's sarcoma.

The present invention further provides a method for the treatment of a clinical condition in an animal, for example, a mammal including a human which clinical condition includes those which have been discussed in the introduction hereinbefore, which comprises treating said animal with a therapeutically effective amount of a compound according to the invention. The present invention also includes a method for the treatment or prophylaxis of any of the aforementioned infections or conditions.

In yet a further aspect, the present invention provides the use of a compound according to the invention in the manufacture of a medicament for the treatment or prophylaxis of any of the above mentioned viral infections or conditions.

The above compounds according to the invention and their pharmaceutically acceptable derivatives may be employed in combination with other therapeutic agents for the treatment of the above infections or conditions. Combination therapies according to the present invention comprise the administration of at least one compound of the present invention and at least one other pharmaceutically active ingredient. The active ingredient(s) and pharmaceutically active agents may be administered simultaneously in either a the same or different pharmaceutical formulations or sequentially in any order. The amounts of the active ingredient(s) and pharmaceutically active agent(s) and the relative timings of administration will be selected in order to achieve the desired combined therapeutic effect. Preferably the combination therapy involves the administration of one compound according to the invention and one of the agents mentioned herein below.

Examples of such further therapeutic agents include agents that are effective for the treatment of viral infections or associated conditions such as (1 alpha, 2 beta, 3 alpha)-9-[2,3-bis(hydroxymethyl)cyclobutyl]guanine [(−)BHCG, SQ-34514], oxetanocin-G (3,4-bis-(hydroxymethyl)-2-oxetanosyl]guanine), acyclic nucleosides (e.g. acyclovir, valaciclovir, famciclovir, ganciclovir, penciclovir), acyclic nucleoside phosphonates (e.g. (S)-1-(3-hydroxy-2-phosphonyl-methoxypropyl)cytosine (HPMPC), ribonucleotide reductase inhibitors such as 2-acetylpyridine 5-[(2-chloroanilino)thiocarbonyl) thiocarbonohydrazone, 3'azido-3'-deoxythymidine, other 2',3'-dideoxynucleosides such as 2',3'-dideoxycytidine, 2',3'-dideoxyadenosine, 2',3'-dideoxyinosine, 2',3'-didehydrothymidine, protease inhibitors such as indinavir, ritonavir, nelfinavir, [3S-[3R*(1R*, 2S*)]]-[3[[(4-aminophenyl)sulfonyl](2-methylpropyl) amino]-2-hydroxy-1-(phenylmethyl)propyl]-tetrahydro-3-furanyl ester (141W94), oxathiolane nucleoside analogues such as (−)-cis-1-(2-hydroxymethyl)-1,3-oxathiolane 5-yl)-cytosine (lamivudine) or cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclopropylamino)-9 H-purin-9-yl]-2-cyclopentene-1-methanol, ribavirin, 9-[4-hydroxy-2-(hydroxymethyl)but-1-yl]-guanine (H2G), tat inhibitors such as 7-chloro-5-(2-pyrryl)-3H-1,4-benzodiazepin-2-(H)one (Ro5-3335), 7-chloro-1,3-dihydro-5-(1H-pyrrol-2yl)-3H-1,4-benzodiazepin-2-amine (Ro24-7429), interferons such as α-interferon, renal excretion inhibitors such as probenecid, nucleoside transport inhibitors such as dipyridamole; pentoxifylline, N-acetylcysteine (NAC), Procysteine, α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof, or non-nucleoside reverse transcriptase inhibitors (NNRTIs) such as nevirapine (BI-RG-587), loviride (α-APA) and delavuridine (BHAP), and phosphonoformic acid, and 1,4-dihydro-2H-3,1-benzoxazin-2-ones NNRTIs such as (−)-6-chloro4-cyclopropylethynyl-4-trifluoromethyl-1,4-dihydro-2H-3,1-benzoxazin-2-one (L-743,726 or DMP-266), and quinoxaline NNRTIs such as isopropyl (2S)-7-fluoro-3,4-dihydro-2-ethyl-3-oxo-1(2H)-quinoxalinecarboxylate (HBY1293).

More preferably the combination therapy involves the administration of one of the above mentioned agents and a compound within one of the preferred or particularly preferred sub-groups within formula (I) as described above. Most preferably the combination therapy involves the joint use of one of the above named agents together with one of the compounds of formula (I) specifically named herein.

The present invention further includes the use of a compound according to the invention in the manufacture of a medicament for simultaneous or sequential administration with at least one other therapeutic agent, such as those defined hereinbefore.

In a further aspect of the present invention there is provided a method of treatment or prophylaxis of restenosis by administration of a compound according to the invention.

Restenosis is the narrowing of the blood vessels which can occur after injury to the vessel wall, for example injury caused by balloon angioplasty or other surgical techniques, and is characterized by excessive proliferation of smooth muscle cells in the walls of the blood vessel treated. Restenosis following angioplasty (RFA) occurs in patients who have been treated for coronary artery disease by balloon angioplasty. It is thought that in many patients suffering from RFA, viral infection, particularly by CMV and/or HHV-6, of the patient plays a pivotal role in the proliferation of the smooth muscle cells in the coronary vessel treated.

Restenosis can occur following a number of surgical techniques, for example, transplant surgery, vein grafting, coronary by-pass grafting and, most commonly, following angioplasty.

Angioplasty is a surgical techniques wherein atherosclerotic stenoses in the peripheral, renal and coronary vasculature are opened up by compressing and/or earing the plaque on the vessel walls, typically by means a pressurized balloon catheter. Unfortunately, in 25 to 50% of cases, particularly those involving the coronary vasculature, the treated vessel restenoses within a few months so that the operation must be repeated. Alternatives to the balloon catheter, such as pulsed lasers and rotary cutters, have been developed with a view to reducing or preventing restenosis following angioplasty, but have met with limited success. A number of drugs including anti-coagulants and vasodilators have also been tried with disappointing or equivocal results.

There is now a strong body of evidence, from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

The present invention further includes a process for the preparation of compounds of formula (I) and pharmaceutically acceptable derivatives thereof which comprises:

A) Reacting a compound of formula (I) wherein $R^1$ is hydrogen and $R^2$, $R^3$, and $R^4$ are as hereinbefore defined, and $R^5$–$R^{18}$ are as hereinbefore defined, with a suitable halogenation agent such as N-bromosuccinimide (NBS); or when $R^1$ is a suitable leaving atom or group, for example, a halo atom such as bromine or an organo (for example alkyl) sulphone, or organo (for example alkyl or aralkyl) sulphonate such as methylsulphone (MeS(O)$_2$—), methylsulphonate (MeS(O)$_2$O—) or tosylate (4-MePhS(O)$_2$O—), with a nucleophile such as amines, alkoxides, mercaptides; or B) Reacting a compound of formula (IV)

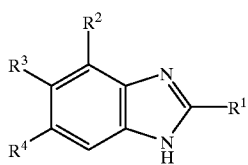

(IV)

wherein $R^1$ is hydrogen, a halo atom, —NR$^{19}$R$^{20}$ (wherein $R^{19}$ and $R^{20}$ are as hereinbefore defined), and $R^2$, $R^3$, $R^4$ and $R^5$ are as hereinbefore described with a compound of formula (Va), (Vb), or (Vc)

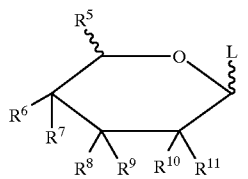

(Va)

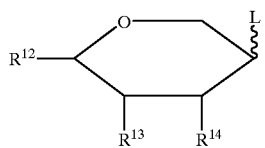

(Vb)

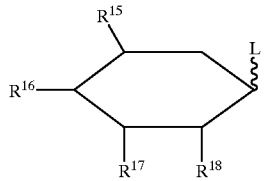

(Vc)

wherein $R^5$–$R^{18}$ are as is hereinbefore defined and L is a suitable leaving group for example, a halo (for example, fluoro, chloro or bromo), an organosulphonyloxy, an alkyl or arylthio (for example, phenylthio) or an aryl or aliphatic ester group such as benzoate or acetate, or a methoxy. Alternatively, intermediates of formula (Vb) and (Vc) where L is amino may be reacted with appropriate aromatic nitro compounds as described in WO9/07646. Thereafter or simultaneously therewith one or more of the following further steps may be additionally performed in any desired or necessary order:

(i) removing any remaining protecting group(s);
(ii) converting a compound of formula (I) or a protected form thereof into a further compound of formula (I) or protected form thereof;
(iii) converting the compound of formula (I) or a protected form thereof into a pharmaceutically acceptable derivative of the compound of formula (I) or a protected form thereof;
(iv) converting a pharmaceutically acceptable derivative of the compound of formula (I) or a protected form thereof into the compound of formula (I) or a protected form thereof;
(v) converting a pharmaceutically acceptable derivative of the compound of formula (I) or a protected form thereof into another pharmaceutically acceptable derivative of the compound of formula (I) or a protected form thereof;
(vi) where necessary, separating the enantiomers and diastereomers of the compound of formula (I) or of a protected derivative thereof or of a pharmaceutically acceptable derivative of a compound of formula (I) using methods known to persons skilled in the art.

A. Process A may conveniently be used for the preparation of a compound of formula (I) wherein $R^1$ is a halogen. Such compounds may conveniently be prepared by reacting a compound of formula (I) wherein $R^1$ is hydrogen and $R^2$–$R^{18}$ are as hereinbefore defined with a halogenating agent. Halogenation may be effected in a conventional manner, for example, bromination using a brominating agent such as N-bromosuccinimide (NBS) in an aprotic solvent such as tetrahydrofuran (THF) or preferably 1,4-dioxane heated to 60–150° C.

Compounds of formula (I) wherein $R^1$ is —NR$^{19}$R$^{20}$ (wherein $R^{19}$ and $R^{20}$ are as hereinbefore defined) may conveniently be prepared from compounds of formula (I) wherein $R^1$ is a halo atom, such as bromo or chloro atom, by reaction with an appropriate amine HNR$^{19}$R$^{20}$, wherein $R^{19}$ and $R^{20}$ are as hereinbefore defined. Typically, the reaction is effected at an elevated temperature, 70–80° C., in an organic solvent such as ethanol or dimethylsulfoxide. Amines of formula HNR$^{19}$R$^{20}$ are commercially available or are readily prepared by a person skilled in the art.

Compounds of formula (I) wherein $R^1$ is —OR$^{21}$ (wherein $R^{21}$ is as hereinbefore defined) may conveniently be prepared from compounds of formula (I) wherein $R^1$ is a halo atom, such as bromo or chloro atom, by reaction with an appropriate alcohol of formula HOR$^{21}$ (wherein $R^{21}$ is as hereinbefore defined). Typically, the reaction is effected at −20 to 100° C., preferably at 25° C., in HOR$^{21}$ or dimethylsulfoxide as solvent and in the presence of a strong base such as sodium hydride. Alcohols of formula HOR$^{21}$ are available commercially or may be readily prepared by a person skilled in the art.

Compounds of formula (I) wherein $R^1$ is —SR$^{22}$ (wherein $R^{22}$ is as hereinbefore defined) may conveniently be prepared from compounds of formula (I) wherein $R^1$ is a halo atom, such as bromo or chloro atom, by reaction with an appropriate thiol of formula HSR$^{22}$ (wherein $R^{22}$ is as hereinbefore defined). Typically, the reaction is effected at −20 to 100° C., preferably at 25° C., in N,N-dimethylformamide or dimethylsulfoxide as solvent and in the presence of a strong base such as sodium or potassium hydride. Thiols of formula HSR$^2$ are available commercially or may be readily prepared by a person skilled in the art.

Compounds of formula (I) in which $R^3$ or $R^4$ is an aryl or heterocyclic group, and $R^5$–$R^{18}$ are as hereinbefore defined, may be prepared from compounds of formula (I) in which $R^3$ or $R^4$ is a halo atom, such as a bromo atom, by reaction with an aryl or heterocyclic trialkyltin (IV) reagent. These reactions are typically effected in the presence of a palladium catalyst such as tetrakis(triphenylphosphine)palladium (0), palladium (II) acetate, or palladium (II) chloride bis (acetonitrile) also in the presence of a solvent such as N,N-dimethylformamide and at an elevated temperature, preferably 90° C. The desired aryl or heterocyclic trialkyltin (IV) reagent may be obtained commercially or may be readily prepared by a person skilled in the art.

The protecting groups may be removed by conventional chemical techniques well known to a skilled person.

Compounds of formula (I) wherein any of $R^6$–$R^{18}$ is a hydroxy group or $R^6$–$R^{11}$ is either a hydroxy group or a fluorine atom and $R^1$–$R^5$ are as hereinbefore defined may be prepared from a corresponding compound of formula (I) wherein any of $R^6$–$R^{18}$ is a protected hydroxy group or $R^6$–$R^{11}$ is a protected hydroxy group or a fluorine atom. Conventional protecting groups may be used for $R^6$–$R^{18}$. Advantageously, ester groups such as those described above in relation to the esters of compounds of formula (I) may be used. These protecting groups may be removed either by conventional chemical techniques such as sodium carbonate in water and methanol or enzymatically, for example, using pig liver esterase. Alternatively, $R^6$–$R^{18}$ may include silyl ethers such as tert-butyldiphenyl-, tert-butyldimethyl-, and triisopropylsilyl ethers which may be deprotected to give a hydroxyl group using an appropriate fluoride source, for example HF/pyridine, $Bu_4NF$ or $Et_4NF$ or a cyclic acetal or ketal such as benzylidene or isopropylidene which can be removed under acidic conditions, for example, using tosic acid and methanol.

Alternatively, the compounds of formula (I) where any of $R^6$–$R^{18}$ is a protected hydroxy group or $R^6$–$R^{11}$ is either a protected hydroxy group or a fluorine atom and $R^2$, $R^3$, $R^4$ and $R^5$ are as hereinbefore defined may be reacted with an agent or under conditions whereby the leaving group $R^1$ is converted to the desired $R^1$ group simultaneously with removal of the protecting groups. Examples of such agents include cyclopropylamine and other primary and secondary amines providing that these agents are sufficiently nucleophilic and are not sterically hindered.

B. Compounds of formula (I) wherein $R^1$ is as hereinbefore defined may be prepared by reaction of a compound of formula (IV) wherein $R^1$ is as hereinbefore defined and $R^2$, $R^3$, and $R^4$ are as hereinbefore defined, with a compound of formula (V), wherein $R^5$–$R^{18}$ are as hereinbefore defined and protected when appropriate and L is as hereinbefore described. The reaction of compounds of formula (IV) with those of formula (V) may be effected using a Lewis acid such as trimethylsilyl trifluoromethanesulfonate, stannic chloride, or boron trifluoride, the former being preferred. The reaction is generally effected in an aprotic solvent and at an elevated temperature, for example, in acetonitrile at 15–30° C. or 1,2-dichloroethane at 70–90° C. Alternatively, the reactions of compounds of formula (IV) with those of formula (V) may be effected by applying procedures of pyrimidine nucleoside synthesis as described and referenced by Tohru Ueda in *Chemistry of Nucleosides and Nucleotides*, vol. 1 (Leroy B. Townsend, ed.) pp. 1–112, Plenum Press, New York, 1988 or purine nucleoside synthesis as described and referenced by Prem C. Srivastva, Roland K. Robins and Rich B. Meyer, Jr., ibid, pp. 113–281 or pyranose nucleoside synthesis as described and referenced by P. Herdewijn, A. Van Aerschot, J. Balzarini and E. De Clerq in *Nucleosides and Nucleotides*, Volume 10, 1991, pp. 119–127, and U.S. Pat. No. 5,399,580, incorporated herein by reference hereto.

The compound of formula (IV) is advantageously trimethylsilylated at the $N_1$-position in the above procedures to improve solubility; for example, by treatment with trimethylsilylchloride, hexamethyl disilazane or, most preferably, N,O-bis(trimethylsilyl)acetamide (BSA). The silylation can be effected in a solvent, preferably 1,2-dichloroethane or acetonitrile, preferably at 70–80° C. After completion of the silylation reaction, a Lewis acid may be added, followed by the addition of the compound of formula (V).

Compounds of formula (Va) may be purchased, for example, from Aldrich (Milwaukee, Ill.) or Pfanstiehl (Waukegan, Ill.) or may be prepared by literature methods well known to persons skilled in the art, for example J. Barbat et at., *Carbohydrate Research*, 116 (1983), pp. 312–316; M. Fuertes et al., *J. Org. Chem.*, 40 (1975), pp. 2372–2377; L. Lerner et al., *J. Med. Chem.*, 30 (1987), pp. 1521–1525.

Compounds of formula (Va) in which $R^5$ is as hereinbefore defined and only one of $R^6$–$R^{11}$ is an unprotected hydroxyl and L is methoxy may undergo deoxygenation via a phenyl thiocarbonate prepared by reaction of the previous free hydroxyl with a chlorothionoformate such as phenylchlorothioformate. The intermediate thionocarbonate is removed via a reductant, such as tributyltin huydride. This reaction is typically effected in the presence of a radical initiator, 2,2'-azobisisobutyronitrile, for example, and in the presence of an aromatic solvent, toluene for example. This intermediate can then eventually be converted to a compound of formula (Va) in which hydroxyls are protected as esters, acetyl esters for example, by reaction with an acid, acetic acid for example, and an acylating agent, acetic anhydride for example. This reaction is typically effected in the acylating agent as solvent at 0–100° C. alternatively, deoxygenation may be effected. for example, as described by P. Collins and R. Ferrier in *Monosaccharides* (1995), John Wiley & Sons, New York, p. 213, and references therein.

Fluorinated compounds of formula (Va) may be prepared by methods known to one skilled in the art, for example, by reaction of an unprotected hydroxyl group of a compound of formula (Va) with a fluorinating agent, diethylaminosulfur trifluoride for example. This reaction is typically effected in an aprotic solvent, such as chloroform or toluene, and at an elevated temperature, advantageously 75° C. Fluorinated and other halogenated deoxy sugars of formula (Va) may also be prepared in analogous fashion as described for like and different carbohydrates by P. Collins and R. Ferrier in *Monosaccharides* (1995), John Wiley & Sons, New York, pp. 248–262 and references therein.

Compounds of formula (Va) in which $R^5$ is as hereinbefore defined and only one of $R^6$–$R^{11}$ is an unprotected hydroxy may be oxidized to a ketone by methods known to persons skilled in the art, for example methods described or referenced by R. C. Petter et al. in *Tetrahedron Letters*, 30 (1989), pp. 659–662, S. Czernecki et al. in *Tetrahedron Letters*, 26 (1985), pp. 1699–1702, or M. Hudlicky in *Oxidations in Organic Chemistry ACS Monograph* 186 (1990), American Chemical Society, Washington D.C. Such ketone compounds may be treated with appropriate Grignard reagents or alkyl metal reagents and carbon nucleophiles to effect alkylation to give a new compound of formula (Va), for example, as described by P. Collins and R. Ferrier in *Monosaccharides* (1995), John Wiley & Sons, New York, p. 3092 and references therein. Additionally Wittig reagents may be employed to prepare olefins of formula (Va), for example, as described by P. Collins and R. Ferrier, ibid, p. 263 and references therein or as described by R. C. Petter et al. in *Tetrahedron Letters*, 90 (1989), pp. 659–662. Hydroboration-oxidation of olefins of formula (Va) using procedures described by H. Redlich et al. in *Synthesis*, (1992), pp. 1112–1118 or as described by Acton et al. in the *Journal of Medicinal Chemistry*, 22 (1972), pp. 518–526, leads to hydroxyl methyl derivatives of formula (Va). Additionally, hydride reagents may be used to effect inversion of hydroxyl stereochemistry of $R^6$–$R^{11}$ from such a described ketone by methods known to persons skilled in the art and using commonly accepted appropriate practices of carbonyl reduction as those described by M. Hudlicky in *Reductions in Organic Chemistry ACS Monograph* 188 (1996), American Chemical Society, Washington, D.C., pp. 149–190.

Compounds of formula (Vb) and (Vc) may be made by methods known to persons skilled in the art.

Compounds of formula (IV), wherein $R^1$ is hydrogen or a halo atom, most preferably chloro or bromo, and $R^2$, $R^3$, and $R^4$ are as hereinbefore defined, may be prepared in accordance with the methods described in PCT specification WO92/07867 incorporated herein by reference. Alternatively, compounds of formula (IV), wherein $R^1$ is hydrogen or a halo atom, most preferably chloro or bromo, and $R^2$, $R^3$, and $R^4$ are as hereinbefore defined, may be prepared in accordance with the methods described by Leroy Townsend, et al. *J. Med. Chem.*, Vol. 38, 1995, pg. 4098.

Alternatively, compounds of formula (IV) wherein $R^1$ is —$NR^{19}R^{20}$ wherein $R^{19}$ and $R^{20}$ are as hereinbefore defined, may be prepared by reacting a compound of formula (VI)

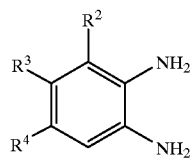

(VI)

wherein $R^2$, $R^3$, and $R^4$ are as hereinbefore defined, with an agent capable of cyclizing the diamine into a benzimidazole. Typically, compounds of formula (VI) may be reacted with an isothiocyanate of formula (VII)

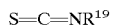

S=C=$NR^{19}$ (VII)

wherein $R^{19}$ is as hereinbefore defined. The reaction may be carried out in the presence of an agent to promote cyclization such as methyl iodide or a carbodiimide such as dicyclohexyl carbodiimide or, 1-cyclohexyl-3-(2-morpholinoethyl) carbodiimide metho-p-toluenesulfonate in the presence of an aprotic aromatic solvent such as toluene and most preferably pyridine and at an elevated temperature, preferably 75–150° C.

Compounds of formula (VII) may be prepared by methods well known skilled person or readily available in the chemical literature or obtained comercially.

Compounds of formula (IV) wherein $R^1$ is hydrogen may be obtained commercially or alternatively may be prepared by reacting a compound of formula (VI) wherein $R^2$, $R^3$, and $R^4$ are as hereinbefore defined with formamidine or most preferably formic acid at ambient temperature to 100° C., advantageously 80° C.

Compounds of formula (VI) may be obtained commercially or may be prepared by methods known to persons skilled in the art or readily available in the chemical literature.

Alternatively, compounds of formula (VI) may be conveniently prepared from compounds of formula (VIII)

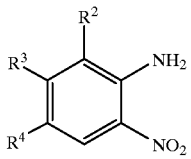

(VIII)

wherein $R^2$, $R^3$, and $R^4$ are as hereinbefore defined, in the presence of a reducing agent, reduced iron for example, and in the presence of an acid, most preferably hydrochloric acid, and in the presence of a solvent such as ethyl alcohol and in the temperature range of 50–78° C. (B. Fox and T. L. Threlfall, Org. Syn. Coll. Vol. 5, 1973, p. 346). Alternatively, such ortho phenylenediamines may be prepared in the presence of a reducing agent such as Raney nickel also in the presence of hydrogen. This reaction is also run in the presence of a solvent, ethyl alcohol for example, at ambient temperature (K. Dimroth, et al, Org. Syn. Coll. Vol. 5, 1973, p.1130). Alternatively, such ortho phenylenediamines may be prepared in the presence of a reducing agent such as sodium hydrosulfite. Typically this reaction is effected in the presence of a polar, protic solvent, preferably a mixture of water and ethanol, and at an elevated temperature, preferably reflux.

Compounds of formula (VIII) may be prepared by methods well known to a skilled person or are readily available commercially. Alternatively, compounds of formula (VIII), where $R^2$ is a halogen atom such as fluorine, chlorine or bromine atom, and $R^3$ and $R^4$ are as hereinbefore defined, may be prepared from compounds of formula (VIII) wherein $R^2$ is hydrogen by reaction with an appropriate halogenating agent such as 1-fluoro-1,4-diazoniabicyclo[2.2.2]octane bis (tetrafluoroborate), N-chlorosuccinimide or N-bromosuccinimide, in the presence of an aprotic solvent such as acetonitrile or N,N-dimethylformamide and at an elevated temperature from 50–100° C.

Alternatively, compounds of formula (VII) wherein $R^4$ is —$SR^{24}$ (wherein $R^{24}$ is as hereinbefore defined) may be prepared from compounds of formula (VIII) wherein $R^4$ is a halo atom and $R^2$ and $R^3$ are as hereinbefore defined by reaction with $HSR^{24}$. This reaction is typically effected in the presence of a strong base such as sodium or potassium hydride and in the presence of a solvent such as dimethylsulfoxide, most preferably N,N-dimethylformamide at ambient temperatures.

Alternatively, compounds of formula (VIII) may advantageously be prepared from compounds of formula (IX),

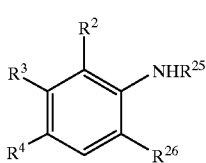

(IX)

wherein $R^{25}$ is hydrogen, $R^{26}$ is a protecting group such as an amide, trifluoroacetamide for example, and $R^2$, $R^3$, and $R^4$ are as hereinbefore defined, by reaction with a nitrating agent such as nitric acid. This reaction is effected in a solvent such as sulfuric acid at temperatures of –20 to 25° C., most preferably at 0° C. The protecting group, $R^{26}$, may be conveniently removed at the end of the reaction sequence with either acid, 2 normal sulfuric acid for example, or base, sodium carbonate in methanol and water for example, at temperatures of 25–100° C.

Compounds of formula (IX) wherein $R^{25}$ is hydrogen and $R^{26}$ is a protecting group such as an amide, trifluoroacetamide for example, and $R^2$, $R^3$ and $R^4$ are as hereinbefore defined, may be prepared from compounds of formula (IX) wherein $R^{25}$ and $R^{26}$ are hydrogen and $R^2$, $R^3$ and $R^4$ are as hereinbefore defined by reaction with an appropriate acylating agent such as trifluoroacetic anhydride. These reactions are effected in the presence of an aprotic solvent such as acetontrile, most preferably 1,4-dioxane, from −10 to 40° C., advantageously at 0° C.

Alternatively, compounds of formula (VIII) in which $R^2$, $R^3$ and $R^4$ are as hereinbefore defined can be prepared from compounds of formula (X)

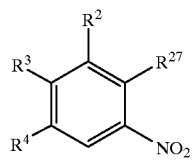
(X)

wherein $R^{27}$ is a halo atom, fluoro or chloro atom for example, by reaction with ammonia. These reactions are typically effected in the presence of a solvent such as ethyl alcohol or 1,4-dioxane and at elevated temperatures, advantageously 100° C.

Compounds of formula (IX) in which $R^{25}$ and $R^{26}$ are hydrogen and $R^2$, $R^3$ and $R^4$ are as hereinbefore defined may be prepared by methods well known to a skilled person or readily available in the chemical literature or obtained commercially.

Compounds of formula (X) may be obtained commercially or may be readily prepared by a person skilled in the art.

Compounds of formula (I) wherein Z is a substituent of formula (Ib) may be made according to Scheme I or by any method known to persons skilled in the art.

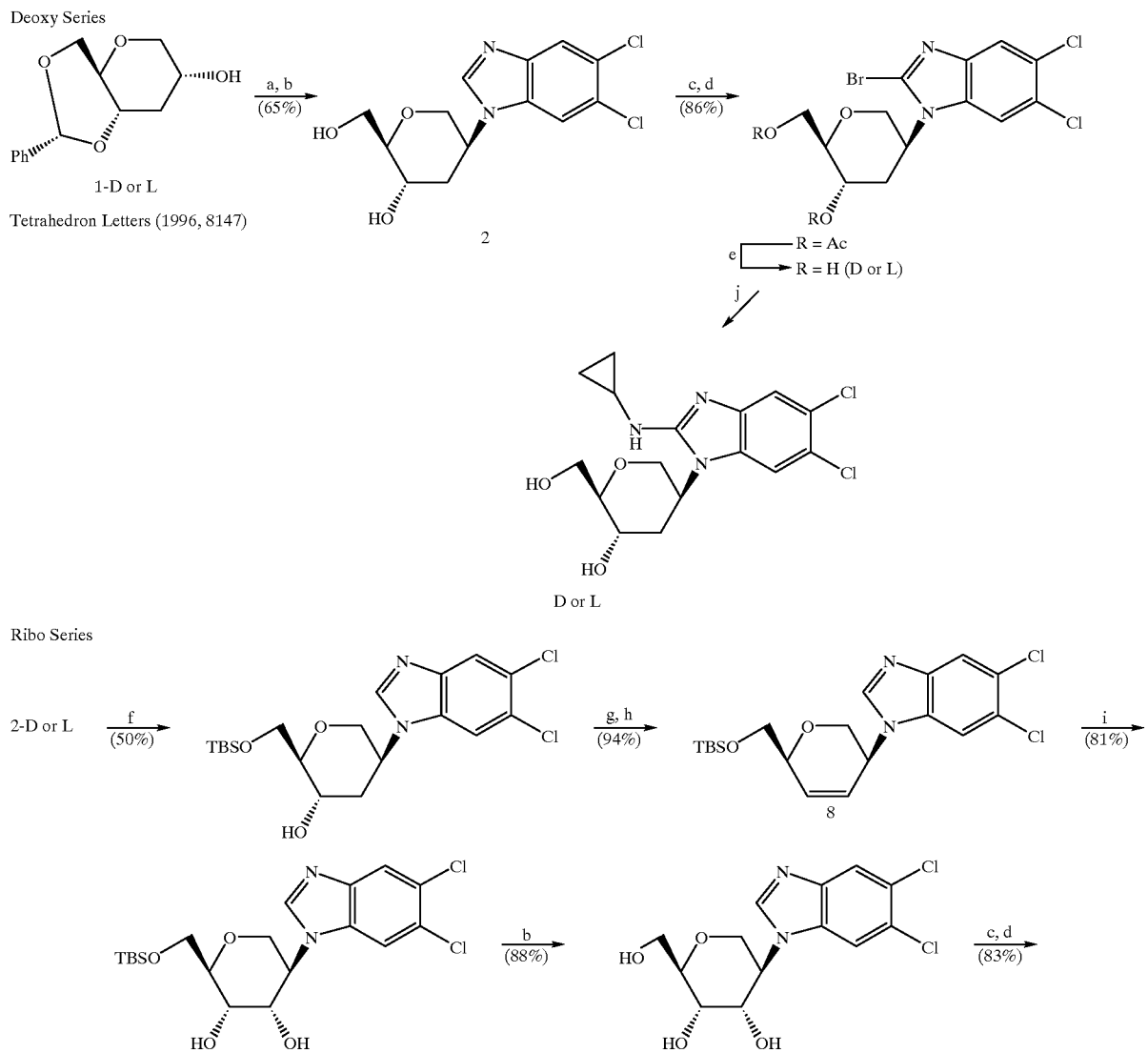

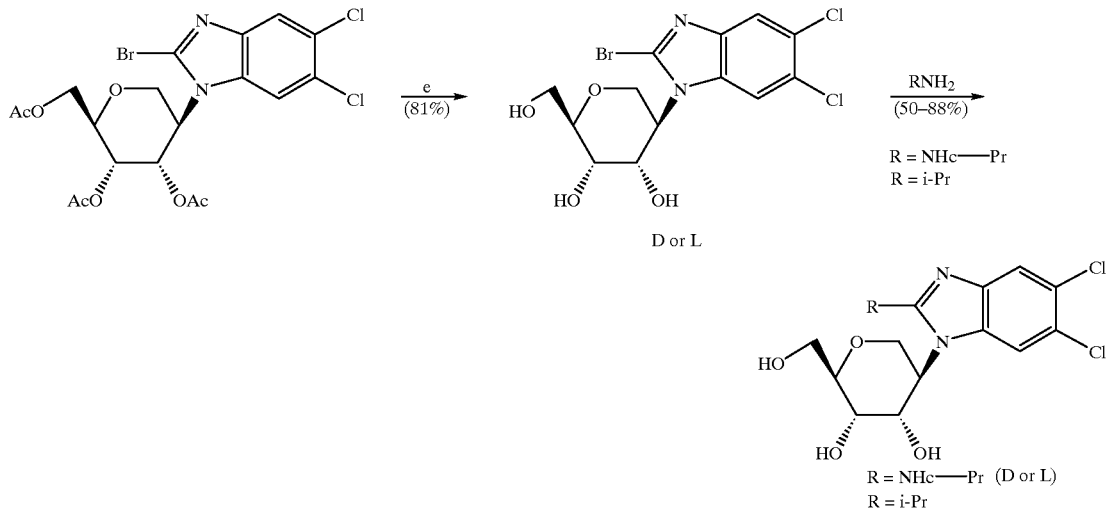

key. a) 5,6-dichlorobenzimidazolela, PPh3, DEAD, THF, 12 h. b) 0.1 N HCl, THF, RT, 12 h. c) Ac2O, Pyr. d) 2 eq. NBS, rflx THF, 10 min. e) 1 eq. Na2CO3, MeOH, EtOH, H2O, 2 h. f) TBDMSCl, imid., DMF. g) MsCl, TEA, CH2Cl2, 0° C. h) DBU, Tol, rflx, 10 h. i) cat. OsO4, NMO, acetone/H2O, 12 h. j) NH₂c——Pr, EtOH, reflux).

Compounds of formula (I) wherein Z is a substituent of formula (Vb) or (Vc) may be made according to U.S. Pat. Nos. 5,399,580, 5,534,535 and WO96/07646, incorporated herein by reference hereto.

The compounds according to the invention, also referred to herein as the active ingredient, may be administered for therapy by any suitable route including oral, rectal, nasal, topical (including transdermal, buccal and sublingual), vaginal and parenteral (including subcutaneous, intramuscular, intravenous, intradermal, and intravitreal). It will be appreciated that the preferred route will vary with the condition and age of the recipient, the nature of the infection and the chosen active ingredient.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 0.5 to 30 mg per kilogram body weight per day and particularly in the range 1.0 to 20 mg per kilogram body weight per day. Unless otherwise indicated, all weights of active ingredient are calculated as the parent compound of formula (I); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, preferably 20 to 500 mg, and most preferably 100 to 400 mg of active ingredient per unit dosage form.

While it is possible for the active ingredient to be administered alone it is preferable to present it as a pharmaceutical formulation. The formulations of the present invention comprise at least one active ingredient, as defined above, together with one or more acceptable carriers thereof and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal or parenteral (including subcutaneous, intramuscular, intravenous, intradermal, and intravitreal) administration. The formulations may conveniently be presented in unit dosage form and may be prepared by any methods well known in the art of pharmacy. Such methods represent a further feature of the present invention and include the step of bringing into association the active ingredients with the carrier which constitutes one or more accessory ingredients. In general, the formulations are prepared by uniformly and intimately bringing into association the active ingredients with liquid carriers or finely divided solid carriers or both, and then if necessary shaping the product.

The present invention further includes a pharmaceutical formulation as hereinbefore defined wherein a compound of formula (I) or a pharmaceutically acceptable derivative thereof and at least one further therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research* 3 (6), 318 (1986).

Formulations of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g.

povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in molds.

Formulations suitable for parenteral administration include aqueous and nonaqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents; and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Preferred unit dosage formulations are those containing a daily dose or daily subdose of the active ingredients, as hereinbefore recited, or an appropriate fraction thereof.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The following examples are intended for illustration only and are not intended to limit the scope of the invention in any way. "Active ingredient" denotes a compound according to the invention or multiples thereof or a physiologically functional derivative of any of the aforementioned compounds.

General Procedures

General Procedure I: Reduction of Substituted Nitroanilines to Substituted Phenylenediamines The appropriate substituted nitroaniline (115–145 mmol), ethanol and Raney nickel (7–8 g wet) (Aldrich, Milwaukee) were combined in a stirred Parr reactor which was pressurized with hydrogen (between 200 and 300 psig). The mixture was allowed to stir at rt overnight, after which time the reactor was depressurized and the mixture was filtered through Celite and the solvents were removed in vacuo to yield a solid appropriate for ring closure to a benzimidazole as describe in General Procedure II.

General Procedure II: Synthesis of Substituted Benzimidazole Bases from Substituted Phenylenediamines To the appropriate substituted phenylenediamine dissolved in enough aqueous 4N HCl to make a 100 mM solution was added 1.25–1.3 equivalents/phenylenediamine of aqueous 88% formic acid. The resulting solution was refluxed between 3 and 18 h followed by cooling to rt and neutralization to pH 7, as determined by indicator paper, with either aqueous sodium hydroxide or ammonium hydroxide. The resulting solid was filtered into a sintered glass funnel, washed with copious amounts of water, air dried then vacuum dried at 50° C. for 24 h or longer. Benzimidazoles thus prepared were suitable for coupling to peracetylated ribopyranose.

General Procedure III: Coupling of 2-bromo-1H-benzimidazoles or 2-unsubstituted Benzimidazoles with Peracetylated Pyranoses The appropriate benzimidazole was magnetically stirred under a nitrogen atmosphere in an oven dried round bottomed flask equipped with a stir bar and reflux condenser in anhydrous 1,2-dichloroethane (Aldrich, Milwaukee) or acetonitrile (Aldrich, Milwaukee). To the stirring suspension was added 1 equivalent/benzimidazole of N,O-bis(trimethylsilyl)acetamide and the resulting mixture was refluxed for 1 to 3 h. The resulting solution was allowed to cool to rt. To this solution was added 1 equivalent/benzimidazole of a peracetylated pyranose followed by 0.50 to 1.1 equivalent/benzimidazole of trimethylsilyl trifluoromethanesulfonate (Aldrich, Milwaukee) or 1.4 to 5 equivalents stannic chloride/benzimidazole from a 1 M solution in dichloromethane (Aldrich, Milwaukee). The new mixture was then heated in an oil bath ca. 85° C. between 0.5 to 24 h as determined by conversion of starting material to product(s) by TLC. Reactions were quenched by pouring the reaction into ca. 7% aqueous sodium bicarbonate and extraction with dichloromethane or ethyl acetate until product was not apparent in the aqueous layer. The organic layer was dried over magnesium sulfate, filtered and solvent removed using a rotrary evaporator. The products were further purified by silica gel column chromatography.

General Procedure IV: Bromination of N-1 Benzimidazole Pyranosides Unsubstituted at C-2

Typically a benzimidazole pyranoside unsubstituted at C-2 was dissolved in enough THF to make a solution between 10 and 30 mM. The solution was refluxed in a rb with an attached reflux condenser and magnetic stirring under a nitrogen atmosphere by an oil bath at ca. 85° C. 2 equivalents/benzimidazole pyranoside of N-bromosuccinimide (NBS, Aldrich, Milwaukee) were added every 15 min to the refluxing solution until bromination of starting material was complete as evidenced by TLC. The reaction was quenched by pouring into cold 7% aqueous sodium bicarbonate and extraction with dichloromethane until product was not apparent in the aqueous layer. The dichloromethane layer was further washed with 4 equivalent volumes of aqueous sodium bicarbonate then 1 volume of water. The organic layer was dried over magnesium sulfate, filtered and solvent removed using a rotary evaporator. The products were further purified by silica gel column chromatography.

General Procedure V: Deprotection of N-1 2-Bromobenzimidazole Acetylated Pyranosides by 1M Aqueous Lithium Hydroxide The appropriate N-1 2-bromobenzimidazole acetylated pyranoside was dissolved in enough dioxane to make a solution between 100 and 200 mM. To the solution was added 1.3 equivalents/acetate to be deblocked of aqueous 1M LiOH. The mixture was allowed to stir between 0.25 and 1 h followed by the addition of enough pH 7 phosphate buffer (VWR, West Chester) to make the resulting solution neutral as shown by pH indicator strips. The mixture was extracted with ethyl acetate until product was not present in the aqueous layer as indicated by TLC. The ethyl acetate layer was washed with 1 equal volume of water, then dried over magnesium sulfate, filtered and solvent removed using a rotary evaporator. Products were further purified by trituration of the solid in dichloromethane and collection of the solid by vacuum filtration onto a sintered glass funnel.

General Procedure VI: Deprotection of N-1 2-Bromobenzimidazole Acetylated Pyranosides by Sodium Carbonate in 4:4:1 Ethanol:Methanol:Water Mixture Every 100 mg of the appropriate N-1 2-bromobenzimidazole acetylated pyranoside was dissolved in 4 ml of methanol followed by the addition of an equivalent volume of ethanol. 2.2 equivalents of sodium carbonate/acetate to be deprotected was added dropwise to the alcoholic solution in an aqueous solution one-fourth the volume of methanol previously used. The suspension was allowed to stir between 2 and 24 h. When TLC indicated that deprotection of acetates from the pyranoside was complete, the suspension was filtered, diluted with water and the solution made neutral with acetic acid as demonstrated by pH indicator paper. The mixture was partitioned between ethyl acetate and water. The aqueous layer was repeatedly extracted with ethyl acetate until all product was in the organic layer. The combined ethyl acetate extracts were dried over magnesium sulfate, filtered and evaporated on a rotary evaporator. Products were further purified by trituration of the resulting solid in dichloromethane and collection of the new solid by vacuum filtration onto a sintered glass funnel.

SYNTHETIC EXAMPLES

Example 1

2-Bromo-5,6-dichloro-1-(2,3,4-tri-O-acetyl-beta-D-ribopyranosyl)-1H-benzimidazole As described in General Procedure III, 2-bromo-5,6-dichlorobenzimidazole (4.0 g, 15 mmol), N,O-bis (trimethylsiyl) acetamide (Aldrich, 3.7 ml, 15 mmol), and 1,2-dichloroethane (Aldrich Sure Seal, 75 ml) were combined and refluxed under nitrogen for 0.5 h. The solution was cooled to room temperature and trimethylsilyl triflate (Aldrich, 3.2 ml, 16 mmol) was added. Immediately, 4.8 g (15 mmol) solid 1,2,3,4-tetra-O-acetyl-b-D-ribopyranose (beta-D-ribopyranose 1,2,3,4-tetraacetate, Aldrich, Milwaukee) was added. The solution was stirred under nitrogen at reflux for 0.5 h, then poured into 7% aqueous sodium bicarbonate and extracted with dichloromethane. The organic layers was dried with magnesium sulfate (anhyd.), filtered, and evaporated. The crude residue was purified on a silica gel column (5×20 cm, 230–400 mesh) with $CH_2Cl_2$ to give 2-bromo-5,6/dichloro-1-(2,3,4-tri-O-acetyl-beta-D-ribopyranosyl)-1H-benzimidazole which was fractionated in two parts based on elution. The faster product fraction was impure (1.9 g) and purified by a second column to give 1.4 g (2.7 mmol); the slower product fraction was (3.0 g, 5.7 mmol) for a total yield of 56%; m.p. 100–110° C.; $^1$H NMR (DMSO-$d_6$) $\delta$8.39 (s,1H), 7.91 (s, 1H), 5.95–5.92 (d, 1H, J=9.6 Hz), 5.73–5.70 (d, 1H, J=9.6 Hz), 5.67 (bs, 2H), 4.13–4.09 (dd, 1H, J=6.3 Hz and J=5.8 Hz), 4.00–3.95 (overlapping dd, 1H), 2.19 (s, 3H), 1.98 (s, 3H), 1.74 (s, 3H).

Anal. Calcd. for $C_{18}H_{17}N_2O_7Cl_2Br$: C, 41.25; H, 3.27; N, 5.34. Found: C, 41.35; H, 3.28; N, 5.38.

Example 2

2-Bromo-5,6-dichloro-1-beta-D-ribopyranosyl-1H-benzimidazole 3.0 g (5.7 mmol) 2-Bromo-5,6-dichloro-1-(2,3,4-tri-O-acetyl-beta-D-ribopyranosyl)-1H-benzimidazole was deprotected as outlined in General Procedure V by being dissolved in 60 ml dioxane and the resultant solution cooled in an ice bath between 0 and 5° C. To this solution was added all at once, 22 ml (22 mmol) of 1M aq. LiOH. The mixture was removed from the ice bath and allowed to stir at ambient temperature for 1 h. The mixture was diluted with 120 ml of pH 7 phosphate buffer and extracted with ethyl acetate. The ethyl acetate layer was dried over magnesium sulfate (anhyd.), filtered and solvents evaporated. The residue was triturated in dichloromethane and 1.7 g (4.3 mmol, 75% yield) of 2-bromo-5,6-dichloro-1-beta-D-ribopyranosyl-1H-benzimidazole was collected by vacuum filtration. The product was dried in a vacuum oven at 50° C. overnight; m.p. 175° C. (decomposes): $^1$H NMR (DMSO-$d_6$) $\delta$7.96 (s,1H), 7.07 (s, 1H), 5.64–5.62 (d, J=9.2 Hz), 5.19–5.17 (d, 1H, J=6.4 Hz), 5.13–5.12 (d, 1H, J=3.2 Hz), 4.86–4.84 (d, 1H, J=6.5 Hz), 4.12–4.06 (m, 1H), 3.98–3.92 (m, 2H), 3.68–3.63 (m, 2H).

Anal. Calcd. for $C_{12}H_{11}N_2O_4Cl_2Br$: C, 36.21; H, 2.79; N, 7.04. Found: C, 36.18; H, 2.91; N, 6.88.

Example 3

5,6-Dichloro-N-1(1-methylethyl)-1-beta-D-ribopyranosyl-1H-benzimidazole-2-amine

2-Bromo-5,6-dichloro-1-beta-D-ribopyranosyl-1H-benzimidazole (0.15 g, 0.29 mmol) was dissolved in 5 ml of absolute ethanol, treated with 5 ml of isopropylamine (Fluka, Ronkonkoma, N.Y.), heated in a glass pressure tube (Ace, Vineland, N.J.) and stirred with a magnetic stir bar. The tube was sealed with a screw cap and heated in an oil bath at 85° C. for 3 days. At this time, TLC indicated complete conversion of starting material and the solvents were removed on a rotary evaporator. The product residue was triturated in dichloromethane to give 5,6-dichloro-N-1 (1-methylethyl)-1-beta-D-ribopyranosyl-1H-benzimidazole-2-amine (0.070 g, 0.19 mmol, 66% yield) as a tan solid;. MS (EI+): m/z (rel. intensity) 375.9 (1.0, M$^+$); $^1$H NMR (DMSO-$d_6$) $\delta$7.37 (s, 1H), 7.33 (s, 1H), 6.47–6.45 (d, 1H, J=7.5 Hz), 5.36–5.34 (d, 1H, J=9.1 Hz), 5.08–5.07 (d, 1H, J=3.2 Hz), 4.93–4.91 (d, 1H, J=7.7 Hz), 4.84–4.82 (d, 1H, J=6.5 Hz), 4.10–3.90 (overlapping m, 3H), 3.90–3.80 (m, 1H), 3.71–3.65 (overlapping dd, 1H), 3.62–3.59 (dd, 1H), 3.14–3.13 (d, 1H, J=5.1 Hz), 1.19–1.17 (d, 1H, J=6.5 Hz).

Example 4

2-Bromo-5,6-dichloro-1-(2,3,4-tri-O-acetyl-beta-L-ribopyranosyl)-1H-benzimidazole As described in General Procedure III, 2-bromo-5,6-dichlorobenzimidazole (2.0 g, 7.6 mmol), N,O-bis (trimethylsiyl) acetamide (Aldrich, 1.9 ml, 7.6 mmol), and acetonitrile (Aldrich Sure Seal, 75 ml) were combined and refluxed under nitrogen for 0.5 h. The solution was cooled to room temperature and a 1.0 M solution of stannic chloride in dichloromethane (Aldrich, 15.2 ml, 15 mmol) was added. Immediately, 2.4 g (7.6 mmol) solid 1,2,3,4-tetra-O-acetyl-beta-L-ribopyranose (as prepared and described for the D-tetraacetate by H. M. Kissman, C. Pidacks and B. R. Baker in *J. Am. Chem. Soc.* 1955, 77, 18–24; mp 110° C.) was added. The solution was stirred under nitrogen at reflux for overnight, then poured into 7% aqueous sodium bicarbonate and extracted with ethyl acetate. The organic layer was dried with magnesium sulfate (anhyd), filtered, and evaporated. The crude residue was purified on a silica gel column (2.5×20 cm, 230–400 mesh) with hexanes and a step gradient from 10 to 20% ethyl acetate to give 2-bromo-5,6/dichloro-1-(2,3,4-tri-O-acetyl-beta-L-ribopyranosyl)-1H-benzimidazole (1.61 g, 3.1 mmol, 40%); MS (API+): m/z (rel. intensify) 524 (0.17, M$^+$); $^1$H NMR (DMSO-d$_6$) δ8.39 (s,1H), 7.91 (s, 1H), 5.95–5.92 (d, 1H, J=9.6 Hz), 5.73–5.70 (d, 1H, J=9.6 Hz), 5.67 (bs, 2H), 4.13–4.09 (dd, 1H, J=6.3 Hz and J=5.8 Hz), 4.00–3.95 (overlapping dd, 1H), 2.19 (s, 3H), 1.98 (s, 3H), 1.74 (s, 3H).

Example 5

2-Bromo-5,6-dichloro-1-beta-L-ribopyranosyl-1H-benzimidazole

An alcoholic solution of 2-bromo-5,6-dichloro-1-(2,3,4-tri-O-acetyl-beta-L-ribopyranosyl)-1H-benzimidazole (0.50 g, 0.95 mmol) was deprotected according to General Procedure VI with 0.61 g (5.8 mmol) of sodium carbonate in 5 ml of water. After stirring overnight at ambient temperature, the mixture was filtered and treated as described in General Procedure VI to give 2-bromo-5,6-dichloro-1-beta-L-ribopyranosyl-1H-benzimidazole (0.27 g, 0.68 mmol, 72% yield); MS (API+): m/z (rel. intensity) 398 (1.0, M$^+$); $^1$H NMR (DMSO-d$_6$) δ7.96 (s,1H), 7.07 (s, 1H), 5.64–5.62 (d, J=9.2 Hz), 5.19–5.17 (d, 1H, J=6.4 Hz), 5.13–5.12 (d, 1H, J=3.2 Hz), 4.86–4.84 (d, 1H, J=6.5 Hz), 4.12–4.06 (m, 1H), 3.98–3.92 (m, 2H), 3.68–3.63 (m, 2H).

Example 6

5,6-Dichloro-N-1(1-methylethyl)-1-beta-L-ribopyranosyl-1H-benzimidazole-2-amine

2-Bromo-5,6-dichloro-1-(2,3,4-tri-O-acetyl-beta-L-ribopyranosyl)-1H-benzimidazole (1.0 g, 1.9 mmol) was dissolved in 5 ml of ethanol and treated with 8 ml of isopropylamine in a glass pressure tube (Ace) with a magnetic stir bar. The tube was sealed with a screw cap and the mixture heated at 100° C. for 3 days. At this time, TLC indicated complete conversion of starting material and the solvents were removed on a rotary evaporator. The product residue was triturated in dichloromethane to give 5,6-dichloro-N-1(1-methylethyl)-1-beta-D-ribopyranosyl-1H-benzimidazole-2-amine (0.070 g, 0.19 mmol, 66% yield) as a white solid; MS (API+): m/z (rel. intensity) 376 (1.0, M$^+$); $^1$H NMR (DMSO-d$_6$) δ7.37 (s,1H), 7.33 (s, 1H), 6.476–6.45 (d, 1H, J=7.0 Hz), 5.36–5.34 (d, 1H, J=8.8 Hz), 5.08–5.07 (d, 1H, J=2.4 Hz), 4.93–4.91 (d, 1H, J=7.7 Hz), 4.84–4.82 (d, 1H, J=6.3 Hz), 4.10–3.90 (bs, 3H), 3.90–3.80 (bs, 1H), 3.71–3.65 (overlapping dd, 1H), 3.62–3.59 (overlapping dd, 1H), 1.19–1.17 (d, 1H, J=6.3 Hz).

Example 7

2-Bromo-5,6-dichloro-1-(2,3,4-tri-O-acetyl-beta-D-xylopyranosyl)-1H-benzimidazole 2-Bromo-5,6-dichlorobenzimidazole (0.25 g, 0.94 mmol), N,O-bis(trimethylsiyl) acetamide (Aldrich, 1.4 ml, 5.6 mmol), and acetonitrile (Aldrich Sure Seal, 20 ml) were combined and magnetically stirred under a nitrogen atmosphere for 1.5 h. To the silylated base was added 0.30 g (0.94 mmol) 1,2,3,4-tetra-O-acetyl-xylopyranose (Aldrich, Milwaukee) followed by stannic chloride (1.4 mmol, 0.12 ml, Aldrich, Milwaukee). The solution stirred under nitrogen overnight, and additional stannic chloride (0.35 ml, 4.1 mmol) was added the following day. One hour after the second addition of stannic chloride, the reaction was poured into saturated aqueous sodium sulfate, and filtered through a celite pad which was washed with chloroform and water. The filtrate layers were separated. The chloroform layer was washed with 2×150 ml saturated aq. sodium bicarbonate then with 1×150 ml of water. The organic layer was dried with magnesium sulfate (anhyd), filtered, and evaporated. The crude residue was purified on a silica gel column (2.5×20 cm, 230–400 mesh) with hexanes and a step gradient from 0 to 25% ethyl acetate to give the product, 2-bromo-5,6-dichloro-1-(2,3,4-tri-O-acetyl-beta-D-xylopyranosyl)-1H-benzimidazole (0.13 g, 0.24 mmol, 26%); $^1$H NMR (DMSO-d$_6$) δ8.47–8.42 (bs,1H), 7.91 (s, 1H), 6.07–6.02 (bs, 1H), 5.66–5.54 (bs, 3H), 4.18–4.13 (m, 1H), 3.95–3.89 (m, 2H), 2.02 (s, 3H), 1.99 (s, 3H), 1.77 (bs, 3H).

Anal. Calcd. for $C_{18}H_{17}N_2O_7Cl_2Br$: C, 41.25; H, 3.27; N, 5.34. Found: C, 41.32; H, 3.29; N, 5.31.

Example 8

2-Bromo-5,6-dichloro-1-beta-D-xylopyranosyl-1H-benzimidazole

To 2-bromo-5,6-dichloro-1-(2,3,4-tri-O-acetyl-beta-D-xylopyranosyl)-1H-benzimidazole (0.083 g, 0.16 mmol) magnetically stirring in 7 ml of tetrahydrofuran was added sodium carbonate (0.13 g, 1.2 mmol) in 1 ml of water. The mixture was allowed to stir at rt for 7 days, then heated at reflux for 2 h. The mixture was cooled to rt, neutralized with acetic acid (0.059 ml, 1.0 mmol) and stirred for an additional 0.5 h at rt. The product, 2-Bromo-5,6-dichloro-1-beta-D-xylopyranosyl-1H-benzimidazole, was purified on a silica gel column (2.5×10 cm, 230–400 mesh) eluting with ethyl acetate (0.40 g, 0.10 mmol, 63%); m.p. 149.6° C. (decomposes); $^1$H NMR (DMSO-d$_6$) δ7.95 (s,1H), 7.90–7.80 (bs, 1H), 5.48–5.46 (d, J=5.2 Hz), 5.40–5.30 (bs, 1H), 5.23–5.19 (m, 2H), 3.96–3.90 (m, 1H), 3.85–3.50 (2 overlapping bs, 2H), 3.43–3.20 (m, 2H obscured by HOD peak).

Example 9

6-Chloro-5-methyl-(2,3,4-tri-O-acetyl-beta-D-ribopyranosyl)-1H-benzimidazole and 5-Chloro-6-methyl-(2,3,4-tri-O-acetyl-beta-D-ribopyranosyl)-1H-benzimidazole As described in General Procedure III, 5-chloro-6methylbenzimidazole (1.0 g, 6 mmol), N,O-bis(trimethylsiyl) acetamide (Aldrich, 1.3 ml, 5.2 mmol), and 1,2-dichloroethane (Aldrich Sure Seal, 300 mL) were combined and refluxed under nitrogen for 0.5 h. The solution was cooled to room temperature and trimethylsilyl triflate (Aldrich, 1.3 ml, 6.7 mmol) was added. Immediately, 2.0 g (6.3 mmol) solid 1,2,3,4-tetra-O-acetyl-b-D-ribopyranose (beta-D-ribopyranose 1,2,3,4-tetraacetate, Aldrich, Milwaukee) was added. The solution was stirred under nitrogen at reflux overnight, then poured into 7% aqueous sodium bicarbonate and extracted with chloroform. The organic layer was dried with magnesium sulfate (anhyd), filtered, and evaporated. The crude residue was purified on a silica gel column (5×20 cm, 230–400 mesh) eluting with a step gradient of 0.25 to 2.5% methanol in chloroform to give 0.07 g (0.16 mmol) 5-Chloro-6-methyl-(2,3,4-tri-O-acetyl-beta-D-ribopyranosyl)-1H-benzimidazole; MS (AP+): m/z (rel. intensity) 447 (1.0, M$^+$23 (Na)) $^1$H NMR (DMSO-d$_6$) δ8.36 (s,1H), 7.90 (s, 1H), 7.68 (s, 1H), 5.97–5.95 (d, 1H, J=9.1 Hz), 5.72–5.69 (m, 2H), 5.41–5.40 (m, 1H), 4.02–3.92 (m, 2H), 2.42 (s, 3H), 2.20 (s, 3H), 1.98 (s, 3H), 1.69 (s, 3H) and 0.090 g (0.21 mmol) 6-Chloro-5-methyl-(2,3,4-tri-O-acetyl-beta-D-ribopyranosyl)-1H-benzimidazole $^1$H NMR (DMSO-d$_6$) δ8.36 (s,1H), 8.06 (s, 1H), 7.60 (s, 1H), 5.99–5.96 (d, 1H, J=9.6 Hz), 5.73–5.66 (m, 2H), 5.45–5.40 (m, 1H), 4.02–3.92 (m, 2H), 2.37 (s, 3H), 2.20 (s, 3H), 1.98 (s, 3H), 1.69 (s, 3H) and 0.13 g (0.31 mmol) of a mixture of the two regioisomers (11% total yield).

Example 10

2-Bromo-5-chloro-6-methyl-(2,3,4-tri-O-acetyl-beta-D-ribopyranosyl)-1H-benzimidazole The title compound was prepared according to General Procedure IV using) 5-Chloro-6-methyl-(2,3,4-tri-O-acetyl-beta-D-ribopyranosyl)-1H-benzimidazole (0.12 g, 0.28 mmol), 20 ml tetrahydrofuran (Aldrich Sure Seal, Milwaukee), and a total of 2.0 g (11 mmol) of N-bromosuccinimide that was added over 2 h. The product from work-up by General Procedure IV was partially purified on a silica gel column (2.5×20 cm, 230–400 mesh) with dichloromethane containing 0.5% methanol to give 2-Bromo-5-chloro-6-methyl-(2,3,4-tri-O-acetyl-beta-D-ribopyranosyl)-1H-benzimidazole (0.097 g) of sufficient purity for the next step; $^1$H NMR (DMSO-d$_6$) δ7.99 (s,1H), 7.66 (s, 1H), 5.93–5.90 (d, 1H, J=8.9 Hz), 5.69–5.62 (m, 3H), 4.02–3.92 (m, 2H), 2.41 (s, 3H), 2.20 (s, 3H), 1.99 (s, 3H), 1.73 (s, 3H).

Example 11

2-Bromo-5-chloro-6-methyl-1-beta-D-ribopyranosyl-1H-benzimidazole

2-Bromo-5-chloro-6-methyl-(2,3,4-tri-O-acetyl-beta-D-ribopyranosyl)-1H-benzimidazole (0.097 g) was deprotected as outlined in General Procedure V by being dissolved in 5 ml dioxane and the resultant solution cooled in an ice bath between 0 and 5° C. To this solution was added all at once, 0.78 ml (0.78 mmol) of 1M aq. LiOH. The mixture was removed from the ice bath and allowed to stir at ambient temperature for 0.5 h. The mixture was diluted with 50 ml of pH 7 phosphate buffer and extracted with ethyl acetate. The ethyl acetate layer was dried over magnesium sulfate (anhyd.), filtered and solvents evaporated. The residue was triturated in dichloromethane and 0.028 g (0.074 mmol) of 2-bromo-5,6-dichloro-1-beta-D-ribopyranosyl-1H-benzimidazole was collected by vacuum filtration. The product was dried in a vacuum oven at 50° C. overnight; m.p. 150° C. (foams); MS (AP+): m/z (rel. intensity) 400 (1.0, M$^+$23 (Na)); $^1$H NMR (DMSO-d$_6$) δ7.67 (s,1H), 7.65 (s, 1H), 5.62–5.60 (d, J=8.9 Hz), 5.13 (bs, 2H), 4.88–4.87 (m, 1H), 4.13 (bs, 1H), 4.00 (bs, 2H), 3.93 (m, 1H), 2.40 (s, 3H).

Example 12

2-Bromo-6-chloro-5-methyl-(2,3,4-tri-O-acetyl-beta-D-ribopyranosyl)-1H-benzimidazole The title compound was prepared according to General Procedure IV using 6-Chloro-5-methyl-(2,3,4-tri-O-acetyl-beta-D-ribopyranosyl)-1H-benzimidazole (0.37 g, 0.87 mmol), 30 ml tetrahydrofuran (Aldrich Sure Seal, Milwaukee), and a total of 1.2 g (7.0 mmol) of N-bromosuccinimide that was added in ca 0.2 equivalents/ benzimidazole every 15 min over 1 h. The product from work-up by General Procedure IV was purified on a silica gel column (2.5×20 cm, 230–400 mesh) with dichloromethane containing 0.5% methanol to give 2-Bromo-6-chloro-5-methyl-(2,3,4-tri-O-acetyl-beta-D-ribopyranosyl)-1H-benzimidazole (0.33 g, 0.66 mmol, 75%); MS (ES+): m/z (rel. intensity) 526 (1.0, M$^+$23 (Na)); $^1$H NMR (DMSO-d$_6$) δ8.18 (s,1H), 7.62 (s, 1H), 5.97–5.904(d, 1H, J=9.4 Hz), 5.78–5.60 (m, 3H), 4.20–4.10 (m, 1H), 4.05–3.97 (m, 1H) 2.41 (s, 3H), 2.25 (s, 3H), 2.04 (s, 3H), 1.78 (s, 3H)

Example 13

2-Bromo-6-chloro-5-methyl-1-beta-D-ribopyranosyl-1H-benzimidazole

2-Bromo-6-chloro-5-methyl-(2,3,4-tri-O-acetyl-beta-D-ribopyranosyl)-1H-benzimidazole (0.097 g) was deprotected as outlined in General Procedure V by being dissolved in 6 ml dioxane at rt. To this solution was added all at once, 2.6 ml (2.6 mmol) of 1M aq. LiOH. The mixture stirred at ambient temperature for 0.25 h. The mixture was diluted with 50 ml of pH 7 phosphate buffer and extracted with ethyl acetate. The ethyl acetate layer was dried over magnesium sulfate (anhyd.), filtered and solvents evaporated. The residue was triturated in dichloromethane and 2-bromo-6-chloro-5-methyl-1-beta-D-ribopyranosyl-1H-benzimidazole was collected by vacuum filtration. The product was dried in a vacuum oven at 50° C. overnight yet still contained 0.2 mol dichloromethane as evidenced by microanalysis and $^1$H NMR; 0.15 g (57%); (m.p. 170–175° C. (decomposes); $^1$H NMR (DMSO-d$_6$) δ7.76 (s,1H), 7.62 (s, 1H), 5.67–5.63 (d, 1H,J=9.3 Hz), 5.20–5.15 (m, 2H), 4.92–4.89 (d, 1H, J=6.6 Hz), 4.15 (m, 1H), 4.05 (bs, 1H), 3.98–3.90 (m, 1H), 3.75–3.70 (m, 2H), 2.42 (s, 3H).

Anal. Calcd. for C$_{13}$H$_{14}$N$_2$O$_4$ClBr 0.20 CH$_2$Cl$_2$: C, 40.18; H, 3.68; N, 7.10. Found: C, 40.16; H, 3.66; N, 7.13

Example 14

6-Chloro-(2,3,4-tri-O-acetyl-beta-D-ribopyranosyl)-1H-benzimidazole and 5-Chloro-(2,3,4-tri-O-acetyl-beta-D-ribopyranosyl)-1H-benzimidazole As per General Procedure III. 5-chloro-1H-benzimidazole (1.0 g, 6.5 mmol), N,O-bis(trimethlsilyl)acetamide (1.6 ml, 6.6 mmol), in 50 ml 1,2-dichloroethane (Aldrich Sure Seal, Milwaukee) were heated at 85° C. for 0.75 h under a nitrogen atmosphere then allowed to cool to rt. Trimethylsilyl trifluoromethanesulfonate (1.4 ml, 7.2 mmol) and 2.0 g (6.3 mmol) solid 1,2,3,4-tetra-O-acetyl-b-D-ribopyranose (beta-D-ribopyranose 1,2,3,4-tetraacetate, Aldrich, Milwaukee) was added and the mixture was heated in an oil bath at 85° C. for 24 h under a nitrogen atmosphere. The reaction was then poured into 7% aqueous sodium bicarbonate and extracted with dichloromethane. The organic layer was dried with magnesium sulfate (anhyd), filtered, and evaporated. The crude residue was purified on a silica gel column (2.5×20 cm, 230–400 mesh) with CH$_2$Cl$_2$ and an increasing gradient of methanol from 0.25 to 0.5% to provide the title compounds as a mixture of regioisomers. The regioisomers were separated by HPLC on a semi-preparative Chiralpak OD lot No. 369-712-30802 eluting with a mobile phase of 90% hexanes and 10% ethanol at a flow rate of 8.0 ml/min and a pressure of 260 psi with signal detection at 254 nM. 5-Chloro-(2,3,4-tri-O-acetyl-beta-D-ribopyranosyl)-1H-benzimidazole eluted first (RT=18.8 min) and 0.13 g was obtained after evaporation of the solvent. $^1$H NMR (DMSO-d$_6$) δ8.46 (s,1H), 7.94–7.91 (d, 1H, J=8.7 Hz), 7.71–7.70 (d, 1H, J=1.9 Hz), 7.30–7.27 (dd, 1H, J=1.9 Hz, J=8.7 Hz), 6.02–6.00 (d, 1H, J=9.1 Hz), 5.70–5.67 (m, 2H), 5.48–5.34 (m,1H) 4.04–3.93 (m, 2H), 2.20 (s, 3H), 1.98 (s, 3H), 1.69 (s, 3H). 6-Chloro-(2,3,4-tri-O-acetyl-beta-D-ribopyranosyl)-1H-benzimidazole eluted from the chiral column last (RT=28.9 min) and 0.20 g was obtained after evaporation of the solvent. $^1$H NMR (DMSO-d$_6$) δ8.43 (s,1H), 8.10–8.09 (d, 1H, J=2.0 Hz), 7.64–7.62 (d, 1H, J=8.8 Hz), 7.25–7.23 (dd, 1H, J=2.0 Hz, J=8.7 Hz), 6.03–6.00 (d, 1H, J=9.5 Hz), 5.76–5.60 (m, 2H), 5.50–5.40 (m, 1H), 4.04–3.93 (m, 2H), 2.20 (s, 3H), 1.98 (s, 3H), 1.69 (s, 3H).

Example 15

2-Bromo-5-chloro-(2,3,4-tri-O-acetyl-beta-D-ribopyranosyl)-1H-benzimidazole

The title compound was prepared according to General Procedure IV using 5-chloro-(2,3,4-tri-O-acetyl-beta-D-ribopyranosyl)-1H-benzimidazole (0.17 g, 0.41 mmol), 30 ml tetrahydrofuran (Aldrich Sure Seal, Milwaukee), and a total of 2.6 g (7.0 mmol) of N-bromosuccinimide that was added over 2 h. The product from work-up by General Procedure IV was purified on a silica gel column (2.5×20 cm, 230–400 mesh) with dichloromethane containing 1.0% methanol to give 2-Bromo-5-chloro-(2,3,4-tri-O-acetyl-beta-D-ribopyranosyl)-1H-benzimidazole (0.15 g, 0.31 mmol, 76%); MS (ES+): m/z (rel. intensity) 511 (0.25, M$^+$23 (Na)) $^1$H NMR (DMSO-d$_6$) δ8.02–8.00 (d,1H, J=8.7), 7.68 (d, 1H, J=2.1 Hz), 7.30–7.27 (dd, 1H, J=1.9 Hz, J=8.9 Hz), 5.96–5.93 (d, 1H, J=8.9 Hz), 5.67–5.62 (m, 2H), 5.55–5.45 (m,1H), 4.20–3.90 (m, 2H), 2.20 (s, 3H), 1.99 (s, 3H), 1.73 (s, 3H).

Example 16

2-Bromo-5-chloro-1-beta-D-ribopyranosyl-1H-benzimidazole

2-Bromo-5-chloro-(2,3,4-tri-O-acetyl-beta-D-ribopyranosyl)-1H-benzimidazole (0.15 g, 0.31 mmol) was deprotected as outlined in General Procedure V by being dissolved in 5 ml dioxane at rt. To this solution was added all at once, 1.2 ml (1.2 mmol) of 1M aq. LiOH. The mixture stirred at ambient temperature for 0.25 h. The mixture was diluted with 15 ml of pH 7 phosphate buffer and extracted with ethyl acetate. The ethyl acetate layer was dried over magnesium sulfate (anhyd.), filtered and solvents evaporated. The residue was triturated in dichloromethane and 2-bromo-5-chloro-1-beta-D-ribopyranosyl-1H-benzimidazole was collected by vacuum filtration. The product was dried in a vacuum oven at 50° C. (0.041 g , 0.11 mmol 37%); m.p. 120° C. (foams), 150° C. (decomposes); $^1$H NMR (DMSO-d$_6$) δ7.70–7.67 (m,2H), 7.24–7.22 (d, 1H, J=8.7 Hz), 5.64–5.61 (d, 1H,J=9.2 Hz), 5.16 (bs, 1H), 4.07–4.05 (overlapping dd, 1H), 3.98 (bs, 1H), 3.87–3.66 (m, 1H), 3.68–3.66 (d, 2H,J=8.5 Hz).

Example 17

2-Bromo-6-chloro-(2,3,4-tri-O-acetyl-beta-D-ribopyranosyl)-1H-benzimidazole

The title compound was prepared according to General Procedure IV using 6-chloro-(2,3,4-tri-O-acetyl-beta-D-ribopyranosyl)-1H-benzimidazole (0.20 g, 0.41 mmol), 30 ml tetrahydrofuran (Aldrich Sure Seal, Milwaukee), and a total of 0.30 g (0.17 mmol) of N-bromosuccinimide that was added over 0.5 h. The product from work-up by General Procedure IV was purified on a silica gel column (2.5×20 cm, 230–400 mesh) with dichloromethane containing 1.0% methanol to give 2-Bromo-6-chloro-(2,3,4-tri-O-acetyl-beta-D-ribopyranosyl)-1H-benzimidazole (0.11 g, 0.22 mmol, 54%); MS (AP+): m/z (rel. intensity) 511 (0.10, M$^+$23 (Na)) $^1$H NMR (DMSO-d$_6$) δ8.16 (s,1H), 7.60–7.58 (d, 1H, J=8.7 Hz), 7.28–7.26 (dd, 1H, J=1.9 Hz, J=8.6 Hz), 5.95–5.92 (d, 1H, J=9.7 Hz), 5.67–5.60 (m, 3H), 4.13–4.09 (dd, 1H, J=5.3 Hz, J=9.2 Hz), 4.00–3.90 (overlapping dd, 1H) 2.20 (s, 3H), 1.98 (s, 3H), 1.74 (s, 3H).

Example 18

2-Bromo-6-chloro-1-beta-D-ribopyranosyl-1H-benzimidazole

2-Bromo-6-chloro-(2,2,4-tri-O-acetyl-beta-D-ribopyranosyl)-1H-benzimidazole (0.11 g, 0.22 mmol) was deprotected as outlined in General Procedure V by being dissolved in 5 ml dioxane at rt. To this solution was added all at once, 0.86 ml (0.86 mmol) of 1M aq. LiOH. The mixture stirred at ambient temperature for 0.25 h. The mixture was diluted with 15 ml of pH 7 phosphate buffer and extracted with ethyl acetate. The ethyl acetate layer was dried over magnesium sulfate (anhyd.), filtered and solvents evaporated. The residue was triturated in dichloromethane and 2-bromo-6-chloro-1-beta-D-ribopyranosyl-1H-benzimidazole was collected by vacuum filtration. The product was dried in a vacuum oven at 50° C. (0.028 g, 0.077 mmol 35%); m.p. 100° C. (foams), 140° C. (decomposes); $^1$H NMR (DMSO-d$_6$) δ7.74–7.73 (d,1H, J=1.8 Hz), 7.60–7.58 (d,1H, J=8.7 Hz), 7.26–7.23 (dd, 1H, J=1.9 Hz,J= 8.7 Hz), 5.64–5.61 (d, 1H,J=9.3 Hz), 5.13 (bs, 1H), 4.12–4.10 (d, 1H, J=9.2 Hz), 3.99 (s, 1H), 3.94–3.90 (m, 1H), 3.68 (s, 1H) 3.67–3.66 (d, 1H, J=3.9 Hz).

Example 19

5,6-Difluoro-1-(2,3,4-tri-O-acetyl-beta-D-ribopyranosyl)-1H-benzimidazole

As per General Procedure III. 5,6-difluoro-1H-benzimidazole (1.0 g, 6.5 mmol), N,O-bis(trimethlsilyl) acetamide (1.6 ml, 6.5 mmol), in 50 ml 1,2-dichloroethane (Aldrich Sure Seal, Milwaukee) were heated at 85° C. for 2.5 h under a nitrogen atmosphere then allowed to cool to rt. Trimethylsilyl trifluoromethanesulfonate (1.4 ml, 7.2 mmol) and 2.0 g (6.3 mmol) solid 1,2,3,4-tetra-O-acetyl-b-D-ribopyranose (beta-D-ribopyranose 1,2,3,4-tetraacetate, Aldrich, Milwaukee) was added and the mixture was heated in an oil bath at 85° C. for 24 h under a nitrogen atmosphere. The reaction was then poured into 7% aqueous sodium bicarbonate and extracted with dichloromethane. The organic layer was dried with magnesium sulfate (anhyd), filtered, and evaporated. The crude residue was purified on a silica gel column (2.5×20 cm, 230–400 mesh) with $CH_2Cl_2$ and an increasing gradient of methanol from 0.5 to 2% to provide the title compound as a white foam (1.1 g, 2.6 mmol, 40%); MS (API+): m/z (rel. intensity) 524 (0.10, M$^+$1); $^1$H NMR (DMSO-d$_6$) δ8.47 (s,1H), 8.20–8.16 (m, 1H), 7.76–7.71 (m, 1H), 6.02–6.00 (d, 1H, J=9.5 Hz), 5.75–5.69 (m, 2H), 5.53–5.40 (m, 1H), 4.05–3.94 (m, 1H), 2.22 (s, 3H), 2.00 (s, 3H), 1.73 (s, 3H).

Example 20

2-Bromo-5,6-difluoro-1-(2,3,4-tri-O-acetyl-beta-D-ribopyranosyl)-1H-benzimidazole The title compound was prepared according to General Procedure IV using 5,6-difluoro-1-(2,3,4-tri-O-acetyl-beta- D-ribopyranosyl)-1H-benzimidazole (1.1 g, 2.6 mmol), 60 ml tetrahydrofuran (Aldrich Sure Seal, Milwaukee), and a total of 2,8 g (16 mmol) of N-bromosuccinimide that was added in 3 ca. equivalent portions. The product from work-up by General Procedure IV was purified on a silica gel column (2.5×20 cm, 230–400 mesh) with hexanes and an increasing gradient from 5% to 20% ethyl acetate to give 1.0 g (2.0 mmol, 77% yield); MS (ES+): m/z (rel. intensity) 514 (1.0, M$^+$23 (Na)); $^1$H NMR (DMSO-d$_6$) δ8.26–8.21 (m, 1H), 7.73–7.69 (m, 1H), 5.93–5.91 (d, 1H, J=9.0 Hz), 5.69–5.62 (m, 3H), 4.11–3.90 (m, 2H), 2.20 (s, 3H), 1.98 (s,3H), 1.73 (s, 3H).

Example 21

2-Bromo-5,6-difluoro-1-beta-D-ribopyranosyl-1H-benzimidazole

2-Bromo-5,6-difluoro-1-(2,3,4-tri-O-acetyl-beta-D-ribopyranosyl)-1H-benzimidazole (0.88 g, 1.8 mmol), 20 ml dioxane and 7 ml (7 mmol) of 1 M aqueous LiOH was used to prepare 2-bromo-5,6-difluoro-1-beta-D-ribopyranosyl-1H-benzimidazole (0.23 g, 0.63 mmol, 35% yield) according to General Procedure V; MS (ES+): m/z (rel. intensity) 388 (1.0, M$^+$23 (Na)); $^1$H NMR (DMSO-d$_6$) δ7.83–7.79 (m, 1H), 7.73–7.68 (m, 1H), 5.62–5.60 (d, 1H, J=9.4 Hz), 4.10–4.08 (d, 1H, J=9.4 Hz), 3.97–3.95 (bs, 2H) 3.67–3.65 (d, 2H, J=8.2 Hz).

Example 22

5,6-Dichloro-4-fluoro-1-(2,3,4-tri-O-acetyl-beta-D-ribopyranosyl)-1H-benzimidazole As described in General Procedure III, 5,6-dichloro-4-fluorobenzimidazole (1.3 g, 6.3 mmol), N,O-bis(trimethylsiyl) acetamide (Aldrich, 1.6 ml, 6.3 mmol), and 1,2-dichloroethane (Aldrich Sure Seal, 30 mL) were combined and refluxed under nitrogen for 0.5 h. The solution was cooled to room temperature and trimethylsilyl triflate (Aldrich, 0.67 ml, 3.5 mmol) was added. Immediately, 2.0 g (6.3 mmol) solid 1,2,3,4-tetra-O-acetyl-b-D-ribopyranose (beta-D-ribopyranose 1,2,3,4-tetraacetate, Aldrich, Milwaukee) was added. The solution was stirred under nitrogen at reflux overnight, then poured into 7% aqueous sodium bicarbonate and extracted with dichloromethane. The organic layer was dried with magnesium sulfate (anhyd), filtered, and evaporated. The crude residue was purified on a silica gel column (5×20 cm, 230–400 mesh) eluting with 0.5% methanol in chloroform followed by purification on a Biotage medium pressure chromatography cartridge system eluting with 1:1 mixture of ethyl acetate and hexanes to give 1.3 g (2.8 mmol, 44%) of 5,6-dichloro/4-fluoro-1-(2,3,4-tri-O-acetyl-beta-D-ribopyranosyl)-1H-benzimidazole; MS (ES+): m/z (rel. intensify) 485 (1.0, M$^+$23 (Na)); $^1$H NMR (DMSO-d$_6$) δ8.57 (s,1H), 8.28 (s, 1H), 6.07–6.04 (d, 1H, J=9.6 Hz), 5.74–5.67 (m, 2H), 5.49–5.40 (m, 1H), 4.04–3.92 (m, 2H), 2.20 (s, 3H), 1.98 (s, 3H), 1.71 (s, 3H)

Example 23

2-Bromo-5,6-dichloro-4-fluoro-1-(2,3,4-tri-O-acetyl-beta-D-ribopyranosyl)-1H-benzimidazole The title compound was prepared according to General Procedure IV using 5,6-dichloro/4-fluoro-1-(2,3,4-tri-O-acetyl-beta-D-ribopyranosyl)-1H-benzimidazole (1.3 g, 2.8 mmol), 30 ml tetrahydrofuran (Aldrich Sure Seal, Milwaukee), and a total of 5.0 g (28 mmol) of N-bromosuccinimide that was added in 5 ca. equivalent portions over 35 min. The product from work-up by General Procedure IV was purified on a silica gel column (2.5×20 cm, 230–400 mesh) with 0.5% methanol in dichloromethane to give 1.5 g (2.8 mmol) 2-bromo-5,6-dichloro/4-fluoro-1-(2,3,4-tri-O-acetyl-beta-D-ribopyranosyl)-1H-benzimidazole; MS (AP+): m/z (rel. intensity) 564 (0.02, M$^+$23 (Na)); $^1$H NMR (DMSO-d$_6$) δ8.31 (s, 1H), 5.97–5.95 (d, 1H, J=9.1 Hz), 5.70–5.62 (m, 3H), 4.14–4.10 (dd, 1H), 4.02–3.97 (overlapping dd, 1H), 2.20 (s, 3H), 1.98 (s, 3H), 1.75 (s, 3H).

Example 24

2-Bromo-5,6-dichloro/4-fluoro-1-beta-D-ribopyranosyl-1H-benzimidazole

2-Bromo-5,6-dichloro/4-fluoro-1-(2,3,4-tri-O-acetyl-beta-D-ribopyranosyl)-1H-benzimidazole (1.5 g, 2.8 mmol), 25 ml dioxane and 11 ml (11 mmol) of 1 M aqueous LiOH was used to prepare 2-bromo-5,6-dichloro/4-fluoro-1-beta-D-ribopyranosyl-1H-benzimidazole (0.57 g, 1.3 mmol, 46% yield) according to General Procedure V; m.p. 165° C. (foams); MS (ES+): m/z (rel. intensity) 438 (1.0, M$^+$23 (Na)); $^1$H NMR (DMSO-d$_6$) δ7.94 (s, 1H), 5.72–5.69 (d, 1H, J=9.2 Hz), 5.28–5.26 (d, 1H, J=6.2 Hz), 5.22–5.20 (d, 1H, J=3.5Hz), 4.93–4.91 (d, 1H, J=8.6 Hz), 4.16–4.11 (m, 1H) 4.05–3.95 (bs, 2H), 3.69–3.60 (m, 2H).

Anal. Calcd. for C$_{12}$H$_{10}$N$_2$O$_4$FCl$_2$Br: C, 34.64; H, 2.42; N, 6.73. Found: C, 34.47; H, 2.48; N, 6.69.

Example 25

6-Chloro-5-fluoro-1-(2,3,4-triacetyl-beta-D-ribopyranosyl)-1H-benzimidazole and 5-Chloro-6-fluoro-1-(2,3,4-triacetyl-beta-D-ribopyranosyl)-1H-benzimidazole 6-Chloro-5-fluorobenzimidazole (Maybridge, 0.536 g, 3.1 mmoles) was slurried in 1,2-dichloroethane (Aldrich, Sure Seal, 35 ml). BSA ( Aldrich, 388 μL, 1.5 mmoles, 1 eq.) was added and the mixture refluxed in a 90° C. oil bath 1 hour. 2,3,4-Triacetyl-beta-D-pyranoside (Aldrich, 1.0 g, 3.1 mmoles, 1 eq.) was dried by boiling in toluene. Excess toluene was removed in vacuo. The carbohydrate was dissolved in 1,2-dichloroethane (15 ml) and added to the reaction by cannula. Trifluoromethyltriflate (Aldrich, 668 μL, 3.4 mmoles, 1.1 eq) was carefully added and the reaction refluxed overnight. The reaction was cooled to room temperature and washed with brine (3×) until the pH was ~7. The dichloroethane solution was dried with MgSO$_4$, filtered and solvent removed in vacuo. The products, 1:1 ratio, were purified as a mixture by chromatography on 300 g of silica gel eluted with ethyl acetate/hexane (2:1, v/v) followed by neat ethyl acetate in 33% yield; 0.45 g. $^1$H NMR (DMSO-d$_6$) δ8.48 (d,1H, Ar—H, J=9 Hz), 8.29 (d,1H, Ar—H, J=7 Hz), 8.15 (d,1H, Ar—H, J=10 Hz), 7.87 (d,1H, Ar—H, J=6 Hz), 7.69 (d,1H, Ar—H, J=10 Hz), 6.0(m, 2H, H-1'), 5.7(m, 2H), 5.65(m, 2H), 5.45 (m, 2H,), 4.0) (m, overlaps with ethyl acetate), 2.2 (s, 6H, acetate), 1.97 (s, 6H, acetate), 1.95 (s, ethyl acetate), 1.70 (s, 6H, acetate), 1.14 (t, ethyl acetate).

Example 26

2-Bromo-6-chloro-5-fluoro-1-(2,3,4-triacetyl-beta-D-ribopyranosyl)-1H-benzimidazole and 2-Bromo-5-chloro-6-fluoro-1-(2,3,4-triacetyl-beta-D-ribopyranosyl)-1H-benzimidazole 6-Chloro-5-fluoro-1-(2,3,4-triacetyl-beta-D-pyranosyl)-1H-benzimidazole and 5-Chloro-6-fluoro-1-(2,3,4-triacetylbeta-D-pyranosyl)-1H-benzimidazole (0.39 g, 0.91 mmoles) were dried by boiling with toluene. Excess toluene was removed in vacuo. THF (Aldrich, Sure Seal, 13 ml) was added and the solution heated to reflux in a 85° C. oil bath. NBS (Aldrich, 0.31 g, 1.8 mmoles, 2 eq.) was added and reaction refluxed for 7 minutes. The reaction was cooled and poured into cold saturated sodium bicarbonate solution. The products were extracted with ethyl acetate. The organic solution was dried with $MgSO_4$, filtered and solvents removed in vacuo. The residue was purified by chromatography on 40 g of silica gel eluted with ethyl acetate/hexane (1:2, v/v). The product containing fractions were combined and solvents removed. The products were obtained in an approximately 1:1 ratio in 30% yield, 0.14 g. $^1$H NMR (DMSO-$d_6$) δ8.34 (d,1H, Ar—H, J=7 Hz), 8.22 (d,1H, Ar—H, J=10 Hz), 7.86 (d,1H, Ar—H, J=7 Hz), 7.69 (d,1H, Ar—H, J=10 Hz), 5.95 (m, 2H, H-1'), 5.7(m, 6H), 4.1(m, 2H), 4.0(m, overlaps with ethyl acetate), 2.2 (s, 6H, acetate), 1.97 (s, 6H, acetate), 1.95 (s, ethyl acetate), 1.70 (s, 6H, acetate), 1.14 (t, ethyl acetate).

Example 27

2-Bromo-6-chloro-5-fluoro-1-(beta-D-ribopyranosyl)-1H-benzimidazole and 2-Bromo-5-chloro-6-fluoro-1-(beta-D-ribopyranosyl)-1H-benzimidazole 2-Bromo-6-chloro-5-fluoro-1-(2,3,4-triacetyl-beta-D-pyranosyl)-1H-benzimidazole and 2-Bromo-5-chloro-6-fluoro-1-(2,3,4-triacetyl-beta-D-pyranosyl)-1H-benzimidazole (0.14 g, 0.28 mmoles) were dissolved in dioxane (Aldrich, 5 ml). Lithium hydroxide hydrate (Aldrich, 0.037 g, 0.88 mmoles, 3 eq.) was dissolved in water (2.0 ml) and added to the reaction. The solution was stirred at room temperature for 1 hr. The pH of the reaction was adjusted to 7 with 1N HCl. The products were extracted with ethyl acetate (2×), dried with $MgSO_4$, filtered and solvents removed in vacuo. The residue was purified by chromatography on 30 g of silica gel eluted with ethyl acetate/hexane (2:1, v/v). The product containing fractions were combined and solvents removed in vacuo. The products were obtained in an approximately 1:1 ratio in 50% yield, 0.14 g. MS (FAB+); m+1/z, 381, $^1$H NMR (DMSO-$d_6$) δ7.90 (d,1H, Ar—H, J=7 Hz), 7.85 (d,1H, Ar—H, J=7 Hz), 7.79 (d,1H, Ar—H, J=10 Hz), 7.68 (d,1H, Ar—H, J=10 Hz), 5.6 (m, 2H, H-1'), 5.2(brs, 4H, OH), 4.8 (brs, 2H, OH), 4.1 (m, 2H), 4.0 (m, overlaps with ethyl acetate), 3.65 (m, 4H), 1.95 (s, ethyl acetate), 1.14 (t, ethyl acetate).

Example 28

5,6-Dichloro-1-beta-D-ribopyranosyl-1H-benzimidazole 5,6-Dichloro-1-(2,3,4-triacetyl-beta-D-ribopyranosyl)-1H-benzimidazole was prepared starting with 5,6-dichloro-benzimidazole (Townsend and Revankar, *Chem. Rev.* 1970, 70:389) by the procedure used in example 25. The title compound was prepared from the triacetyl product by the method of example 26. MS (APCH(−)): m−1/z 317 $^1$H NMR (DMSO-$d_6$) δ8.43 (s,1H, H-2), 7.97 (s,1H, Ar—H), 7.92(s, 1H, Ar—H), 5.54 (d, 1H, H-1', J=9 Hz), 5.1(brs, 2H, OH), 4.86(brs, 1H, OH), 4.0(m, overlaps with ethyl acetate), 3.8 (m,1H), 3.7 (m,1H), 3.6 (m,1H), 1.95 (s, ethyl acetate), 1.14 (t, ethyl acetate).

Example 29

4,5,6-Trifluorobenzimidazole 2,3,4-Trifluoro-6-nitroanline (Maybridge, 30 g, 156 mmoles) was dissolved in ethanol (200 ml). Water (10 ml) was added followed by Raney Nickel catalyst (3 g, wet). Reduction under 50 psi $H_2$ was continued for 4 hrs. The reaction was filtered and the solvents removed in vacuo. The residue was dissolved in 4N HCl (1 L) and formic acid (6.5 ml, 1.1 eq.) was added. The reaction was refluxed overnight. After filtration, the pH was adjusted to 7 with NaOH (5N). The crude product ( 24 g) was collected by filtration and purified by chromatography on silica gel (500 g) eluted with ethyl acetate/hexane (7:1, v/v). The product containing fractions were combined and solvents removed in vacuo. The product was obtained in 71% yield, 19 g. MS (APCH (+)): m+1/z 173, $^1$H NMR (DMSO-$d_6$) δ8.31 (s,1H, H-2), 7.49 (m,1H, H-7).

Example 30

1-(2,3,4-Triacetyl-beta-D-ribopyranosyl)-4,5,6-trifluoro-1H-benzimidazole and 1-(2,3,4-Triacetyl-beta-D-ribopyranosyl)-5,6,7-trifluoro-1H-benzimidazole The product of example 6 was converted to the title compounds by the method used in example 25. The products were obtained in a ratio of 1:5, 7-F/4-F isomers. Isomer ratios were confirmed by NMR-NOESY correlation. In the case of the 4-fluoro analog, NOE from the 7-H into the sugar protons was clearly present whereas in the case of the 7-fluoro analog no NOE was observed. MS (APCH(+)): m+1/z 431,$^1$H NMR (DMSO-$d_6$) δ8.56 (s, 0.2H, H-2, (7-fluoro analog)), 8.53 (s,1H, H-2, (4-fluoro analog)), 8.1 (m,1H, H-7, (4-fluoro analog)), 7.65 (m, 0.2H, H/4, (7-fluoro analog)), 6.02 (d, 1.2H, H-1', J=10 Hz), 5.7 (m, 2H), 5.55(m, 0.2H), 5.45 (m, 2H), 5.25 (m,0.2H), 4.0 (m, overlaps with ethyl acetate), 2.2 (s, 3.6H, acetate), 1.97 (s, 3.6H, acetate), 1.95 (s, ethyl acetate), 1.70 (s, 3.6H, acetate), 1.14 (t, ethyl acetate).

Example 31

2-Bromo-1-(2,3,4-triacetyl-beta-D-ribopyranosyl)-4,5,6-trifluoro-1H-benzimidazole and 2-Bromo-1-(2,3,4-triacetyl-beta-D-ribopyranosyl)-5,6,7-trifluoro-1H-benzimidazole The products of example 30 were converted to the title compounds by the method used in example 26. MS (EI(+)): m+1/z 508, $^1$H NMR (DMSO-$d_6$) δ8.15 (m, 1H, H-7, (4-fluoro analog)), 7.7 (m, 0.2H, H-4, (7-fluoro analog)), 6.51 (d, 0.2H, J=5 Hz), 5.7 (m, 0.2H), 5.6 (m 2.4H), 5.3 (d, 0.12H), 4.2 (m, 0,2H), 4.1 (m, 1.15H), 4.0 (m, overlaps with ethyl acetate), 2.2 (s, 6H, acetate), 1.97 (s, 6H, acetate), 1.95 (s, ethyl acetate), 1.70 (s, 6H, acetate), 1.14 (t, ethyl acetate).

Example 32

2-Bromo-1-(beta-D-ribopyranosyl)-4,5,6-trifluoro-1H-benzimidazole and 2-Bromo-1-(beta-D-ribopyranosyl)-5,6,7-trifluoro-1H-benzimidazole The products of example 31 were converted to the title compounds by the method used in example 27. Partial purification by chromatography resulted in a ratio of 1:7 for the 7-fluoro/4-fluoro compounds. $^1$H NMR (DMSO-$d_6$) δ7.75 (m, 1H, H-2, (4-fluoro analog)), 7.65 (s, 0.15H, H-2, (7-fluoro analog)), 5.63 (d, 1H, H-1', J=9 Hz), 5.25 (brs, 0.15H, OH), 5.2(m, 1.15H, OH), 5.15 (d, 1H, OH), 4.95 (d, 0.15H, OH), 4.85(d, 1H, OH), 4.1(m, 1.15H), 4.0 (m, 2.3H), 3.65 (m, 2.3H). Analysis: ($C_{12}H_{10}BrF_3N_2O_4$-1/10$H_2O$-2/10 $C_4H_8O_2$), Calculated: C-38.19, H-2.95, N-6.96. Found C-38.19, H-3.10, N-6.81.

Example 33

6-Chloro-4,5-difluoro-1-(2,3,4-triacetyl-beta-D-ribopyranosyl)-1H-benzimidazole and 5-Chloro-6,7-difluoro-1-(2,3,4-triacetyl-beta-D-ribopyranosyl)-1H-benzimidazole a) 4-Chloro-2,3/difluoro-6-nitroaniline 2,3-Difluoro-6-nitroaniline (15.4 g, 88.7 mmol), N-chlorosuccinimide (14.9 g, 111.4 mmol) and N,N-dimethylformamide (250 ml) were combined and were heated to 80–90° C. for several hours, after which time the mixture was poured into ice water. The product was extracted with ethyl acetate which was then washed with water, saturated aqueous sodium chloride, dried over magnesium sulfate, filtered and the solvents were removed in vacuo to leave a yellow, viscous oil. $^1$H NMR (DMSO-$d_6$) δ: 8.03 (dd, J=7.3, 2.2 Hz, 1H, Ar—H), 7.65 (br s, 2H, NH$_2$).

b) 6-Chloro-4,5-difluorobenzimidazole

4-Chloro-2,3-difluoro-6-nitroanline (6 g, 28.8 mmoles) was converted to the title compound by the method used in example 6. MS (APCH(−)): m−1/z 187, $^1$H NMR (DMSO-$d_6$) δ8.36 (s,1H, H-2), 7.61 (m, 1H, H-7).

c) 6-Chloro-4,5-difluoro-1-(2,3,4-triacetyl-beta-D-ribopyranosyl)-1H-benzimidazole and 5-Chloro-6,7-difluoro-1-(2,3,4-triacetyl-beta-D-ribopyranosyl)-1H-benzimidazole The product of example 33b was converted to the title compounds by the method used in example 1. The products were obtained in a ratio of 1:6, 7-F/4-F isomers. Isomer ratios were confirmed by NMR-NOESY correlation. In the case of the 4-fluoro analog, NOE from the 7-H into the sugar protons was clearly present whereas in the case of the 7-fluoro analog no NOE was observed. MS (APCH(+)): m+Na/z 469, $^1$H NMR (DMSO-$d_6$) δ8.57 (s, 1.15H, H-2), 8.2 (m,1H, H-7, (4-fluoro analog)), 7.8 (m, 0.15H, H-4, (7-fluoro analog)), 6.1 (m, 1.15H, H-1'), 5.7 (m, 2.3H), 5.55(m, 0.15H), 5.45 (m, 1H), 5.25 (m, 0.15H), 4.0 (m, 2.3H), 2.2 (s, 3.45H, acetate), 1.97 (s, 3.45H, acetate), 1.70 (s, 3.49H, acetate).

Example 34

2-Bromo-6-chloro-4,5-difluoro-1-(2,3,4-triacetyl-beta-D-ribopyranosyl)-1H-benzimidazole and 2-Bromo-5-chloro-6,7-difluoro-1-(2,3,4-triacetyl-beta-D-ribopyranosyl)-1H-benzimidazole The products of example 33c were converted to the title compounds by the method used in example 2. Partial purification by chromatography resulted in a ratio of 1:5 for the 7-fluoro/4-fluoro compounds. MS (El(+)): m+1/z 524, $^1$H NMR (DMSO-$d_6$) δ8.23 (d, 1H, H-7, J=5 Hz,(4-fluoro analog)), 7.82 (d, 0.2H, H4, J=6 Hz, (7-fluoro analog)), 5.95 (m, 1.2H), 5.7 (m, 2.4H), 5.3 (m, 0.2H), 5.1 (m, 0.2H), 4.2 (m, 0.2H), 4.1(m, 1.2H), 4.0 (m, overlaps with ethyl acetate), 3.9 (m, 0.2H), 3.5 (t, 0.4H), 2.2 (s, 3.4H, acetate), 1.97 (s, 3.4H, acetate), 1.95 (s, ethyl acetate), 1.70 (s, 3.4H, acetate), 1.14 (t, ethyl acetate).

Example 35

2-Bromo-6-chloro-4,5-difluoro-1-(beta-D-ribopyranosyl)-1H-benzimidazole

The product of example 34 was converted to the title compound by the method used in example 27. The title compound was isolated by chromatography. MS (FAB+): m+1/z 399, $^1$H NMR (DMSO-$d_6$) δ7.8 (m, 1H, H-7), 5.64 (d, 1H, H-1', J=9 Hz), 5.20 (d, 1H, OH, J=6 Hz), 5.14 (d, 1H, OH, J=3 Hz), 4.85 (d, 1H, OH, J=6 Hz), 4.1 (m, 1H), 4.0 (m, 2H+ethyl acetate), 3.65 (m, 2H), 1.95 (s, ethyl acetate), 1.14 (t, ethyl acetate).

Example 36

(3S,5S,6R)-2-Bromo-5,6-dichloro-1-(tetrahydro-5-hydroxy-6-(hydroxymethyl)-2H-pyran-3-yl)-1H-benzimadazole a) (3S,5S,6R)-5,6-Dichloro-1-(tetrahydro-5-hydroxy-6-(hydroxymethyl)-2H-pyran-3-yl)-1H-benzimidazole 2R,4-α-R,7R,8-α-S-perhydro-7-hydroxy-2-phenylpyrano(3,2-D)1,3)dioxin (Tetrahedron Letters, 1996, 8147 and references cited therein) (2.50 g, 10.6 mmol), triphenylphosphine (Aldrich, 4.16 g, 15.87 mmol as 99%) and 5,6-dichlorobenzimidazole (Townsend and Revankar, Chem. Rev. 1970, 70:389, and references cited therein) (3.00 g, 15.87 mmol) were stirred in anhydrous tetrahydrofuran (50 ml) at 0° C. (external ice bath) under nitrogen as a solution of diethyl azodicarboxylate (Aldrich, 2.60 ml, 15.87 mmol as 97%) in tetrahydrofuran (10 ml) was added over 30 min. The reaction mixture was allowed to warm to room temperature, stirred 72 hours, then diluted with chloroform (300 ml) and washed with saturated aqueous sodium bicarbonate (100 ml). The organic layer was dried (sodium sulfate), filtered, and the solvents evaporated under reduced pressure. The residual gum was treated with 300 ml of 80% aqueous acetic acid at 80° C. for 1 h. The reaction mixture was diluted with 100 ml of water and extracted with diethyl ether (4×100 ml). The aqueous phase was concentrated and purified by flash chromatography on silica gel 60. The title compound was eluted with 5–25% methanol-chloroform as a white solid (2.20 g, 65%); m.p. 197° C.; 1H-NMR (DMSO-d6, 200 MHz) δ: 8.56, 8.09, 7.99 (s, each 1H), 4.92 (d, J=5.5 Hz, 1H), 4.87 (bs, 1H), 4.69 (t, J=6.3 Hz, 1H), 4.25 (d, J=12 Hz, 1H), 3.91 (dd, J=12.9, 2.7 Hz, 1H), 3.71–2.53 (m, 4H), 2.28–2.25 (m, 1H), 1.97–1.89 (m, 1H).

Anal. Calcd. for C13H14N2O3Cl2: C, 49.23; H, 4.45; N, 8.83; Cl, 22.36. Found: C, 49.31; H, 4.48; N, 8.80; Cl, 22.26.

b) (3S,5S,6R)-2-Bromo-1-(5-acetoxy-6-acetoxymethyl)-tetrahydro-2H-pyran-3-yl)-1H-benzimidazole To a stirred solution of (3S,5S,6R)-5,6-dichloro-1-(tetrahydro-5-hydroxy-6-(hydroxymethyl)-2H-pyran-3-yl)-1H-benzimidazole (part a of this example, 1.00 g, 3.47 mmol) in anhydrous pyridine (10 ml) was added acetic anhydride (1.30 ml, 13.9 mmol). After 12 hours the reaction mixture was concentrated under reduced pressure, coevaporating with toluene to a viscous oil. Ethanol (ca. 5 ml) was added (with external ice cooling) and the mixture was again coevaporated with toluene (2×) until acetic acid. odor was absent. The oil was redissolved in chloroform (200 ml) and washed successively with 0.1 N HCl (50 ml), saturated aqueous sodium bicarbonate (50 ml), and brine (50 ml). The organic layer was dried (sodium sulfate) then suction-filtered through flash silica gel 60 (3×4 cm), washing with ethyl acetate. Evaporation of the solvents under reduced pressure left an off-white semi solid residue (1.37 g). A solution of this solid in anhydrous tetrahydrofuran (20 ml) was refluxed under nitrogen while N-bromosuccinimide (Aldrich, 1.22 g, 6.83 mmol) was added in one portion. After 10 min. at reflux, the yellow solution was cooled to room temperature, diluted with chloroform (75 ml), and washed with saturated aqueous sodium bicarbonate (3×50 ml). The organic layer was dried (sodium sulfate), filtered, and concentrated under reduced pressure, affording 1.95 g (86%) of the title compound as a brown gum which was used without further purification; 1H-NMR (DMSO-d6, 200 MHz) δ: 8.45, 7.98 (s, each 1H), 5.00 (m, 1H), 4.81 (m, 1H), 4.45–3.81 (m, 5H), 2.30 (m, 2H), 2.31 (s, 6H).

c) (3S,5S,6R)-2-Bromo-5,6-dichloro-1-(tetrahydro-5hydroxy-6-(hydroxymethyl)-2H-pyran-3-yl)-1H-benzimadazole (3S,5S ,6R)-5,6-Dichloro-1-(tetrahydro-5-hydroxy-6-(hydroxymethyl)-2H-pyran-3-yl)-1H-benzimidazole (part b of this example, 0.80 g, 1.67 mmol) was stirred in 1:1 methanol-ethanol (10 ml) with a solution of sodium carbonate (0.200 g, 1.68 mmol) in water (5 ml) for 5 hours at room temperature followed by 2 hours at 60° C. The pH was then adjusted to 5 with glacial acetic acid and the solvents evaporated in vacuo. The residual solid was slurried in water, filtered and dried in vacuo, affording the title compound as a white solid (0.500 g, 90%); m.p. 286–288° C.; [α]20D–47.2° (c 0.125, 1:1 EtOH—CHCl3); 1H-NMR (DMSO-d6, 200 MHz) δ: 8.60, 7.93 (s, 1H each), 5.07 (d, J=4.4 Hz, 1H), 4.97 (m, 1H), 4.86 (t, J=4.9 Hz, 1H), 4.26 (m, 1H), 4.04 (m, 1H), 3.74–3.39 (m, 4H), 2.18 (m, 2H).

Anal. Calcd. for C13H13BrCl2N2O3: C, 39.42; H, 3.31; N, 7.07; total halogen as Cl, 17.90. Found: C, 39.51; H, 3.35; N, 6.98; total halogen as Cl, 17.88.

Example 37

(3S,5S,6R)-5,6-Dichloro-2-(cyclopropylamino)-1-(tetrahydro-5-hydroxy-6-(hydroxymethyl)2H-pyran-3-yl)-1H-benzimidazole A solution of (3S,5S,6R)-2-bromo-5,6-dichloro-1-(tetrahydro-5-hydroxy-6-(hydroxymethyl)-2H-pyran-3-yl)-1H-benzimadazole (part c of previous example, 1.00, 2.08 mmol) and cyclopropyl amine (Aldrich, 1.50 ml, 20.0 mmol) in absolute ethanol (20 ml) was refluxed under nitrogen for 24 h at which point TLC (silica gel plates developed with 5% methanol-chloroform) indicated complete conversion to lower Rf product. 1 N sodium hydroxide (2.10 ML) was added and the reaction mixture was concentrated under reduced pressure. The residual solids were chromatographed on silica gel 60. The title compound eluted with 10% methanol-chloroform as a white foam, after evaporation of solvents (0.60 g, 75%); m.p. 130° C.; [α]20D+24.8° (c 0.25, EtOH); 1H-NMR (DMSO-d6, 200 MHz) δ: 7.77 (s, 1H), 7.44 (s, 2H,), 4.96 (d, J=5 Hz, 1H), 4.83 (t, J=5 Hz, 1H), 4.66 (m, 1H), 4.22 (m, 1H), 3.92 (m, dd, J=13.9 Hz, 4 Hz, 1H), 3.71–3.55 (m, 3H), 3.33 (m, 1H), 2.79 (m, 1H), 2.12–1.75 (m, 2H), 0.75–0.48 (m, 4H).

Anal. Calcd. for C16H19Cl2N3O.0.5 H2O: C, 50.41; H, 5.29; N, 11.02; Cl, 18.60. Found: C, 50.29; H, 5.29; N, 11.00; Cl, 18.66.

Example 38

(3R,5R,6S)-2-Bromo-5,6-dichloro-1-(tetrahydro-5-hydroxy-6-(hydroxymethyl)-2H-pyran-3-yl)-1H-benzimadazole The title compound was prepared as described in example 1, starting from L-glucose-derived 2S,4-α-S,7S,8-α-R-perhydro-7-hydroxy-2-phenylpyrano(3,2-D)1,3)dioxin ((Tetrahedron Letters, 1996, 8147 and references cited therein): m.p. 286–287° C.; [α]20D+0.16 (c 0.62, 1:1 MeOH/CHCl3; 1H-NMR (CDCl3, 200 MHz) data was identical to that of the enantiomer (example 36).

Anal. Calcd. for C13H13BrCl2N2O3, C, 39.42:H, 3.31; N, 7.07: total halogen as Cl, 17.90. Found: C, 39.70; H, 3.45; N, 7.02; total halogen as Cl, 17.85.

Example 39

(3R,5R,6S)-5,6-Dichloro-2-(cyclopropylamino)-1-(tetrahydro-5-hydroxy-6-(hydroxymethyl)2H-pyran-3-yl)-1H-benzimidazole The title compound was prepared in the same manner as the enantiomer (example 37), starting from L-glucose-derived 2S,4-α-S,7S,8-α-R-perhydro-7-hydroxy-2-phenylpyrano(3,2-D)1,3)dioxin ((Tetrahedron Letters, 1996, 8147 and references cited therein): m.p. 98–99° C.; [α]20D–23.2° (c 0.28, EtOH); 1H-NMR (CDCl 3, 200 MHz) identical to that of the enantiomer (example 37).

Anal. Calcd. for C16H19Cl2N3O3.3.0 H2O: C, 45.08; H, 5.91; N, 9.86; Cl, 16.63. Found: C, 45.00; H, 5.87; N, 9.79; Cl, 16.70.

Example 40

(3R,4S,5S,6R)-2-Bromo-5,6-dichloro-1-(tetrahydro-4,5-dihydroxy-6-(Hydroxymethyl)-2H-pyran-3-yl)-1H-benzimidazole a) (3S,5S,6R)-5,6-dichloro-1-(6-(((tert-butyldimethylsilyl)oxy)methyl)-tetrahydro-5-hydroxy-2H-pyran-3-yl)-1H-benzimidazole To a stirred suspension of (3S,5S,6R)-5,6-dichloro-1-(tetrahydro-5-hydroxy-6-(hydroxymethyl)-2H-pyran-3-yl)-1H-benzimidazole (example 36, 1.50 g, 4.73 mmol) in 15 ML of dry DMF at 0° C. was added imidazole (0.40 g, 5.68 mmol) followed by tert-butyldimethylsilyl chloride (0.81 g, 5.20 mmol). The reaction was allowed to warm to room temperature, stirred overnight then diluted with water (100 ML) and extracted with chloroform (100 ML). The organic layer was dried over sodium sulfate, filtered and the solvents were removed under reduced pressure. Purification by flash chromatography on silica gel 60 eluting with 50% ethyl acetate-hexanes afforded the title compound as a white solid (1.00 g, 50%) along with 0.40 g recovered starting material; m.p. 143–155° C.; 1H-NMR (DMSO-d6, 200 MHz) δ: 8.51, 8.09, 8.00 (s, each 1H), 4.90 (d, J=5.6 Hz, 1H), 4.89 (m, 1H), 4.26 (m, 1H), 3.91 (m, 1H), 3.86 (m, 1H), 3.55–3.42 (m, 1H), 3.32–3.24 (m, 2H), 2.29–2.19 (m, 1H), 1.97–1.83 (m, 1H), 0.91 (s, 9H), 0.97, 0.78 (s, each 3H).

Anal. Calcd. for C19H28Cl2N2O3Si.0.40 H2O: C, 52.03; H, 6.62; N; 6.39; Cl, 16.16. Found: C, 52.20; H, 6.57; N, 6.39; Cl, 16.02.

b) (3S,6R)-5,6-Dichloro-1-(3,6-dihydro-6-(((tert-butyldimethylsilyl)oxy)methyl)-2H-pyran-3-yl)-1H-benzimidazole To a stirred solution of (3S,5S,6R)-5,6-dichloro-1-(6-((tert-butyldimethylsilyl)oxy)methyl)-tetrahydro-5-hydroxy-2H-pyran-3-yl)-1H-benzimidazole (part a of this example, 1.51 g, 3.58 mmol) in 20 ML of anhydrous methylene chloride at 0° C. was added triethyl amine (1.50 ML, 10.74 mmol) followed by dropwise addition of methanesulfonyl chloride (0.42 ML, 5.37 mmol). The reaction was stirred 10 minutes then poured into ice-water (50 ML) and extracted with methylene chloride (2×50 ML). The combined organic extracts were washed successively with saturated ammonium chloride and brine (50 ML each), then dried over sodium sulfate. Filtration and removal of solvents under reduced pressure afforded the crude mesylate (1.83 g) as a white foam which was dissolved in toluene (25 ML), treated with 1,8-diazobicyclo[5.4.0]undec-7-ene (1.40 ML, 8.95 mmol) and heated at reflux for 48 h. The reaction mixture was cooled to room temperature, diluted with ethyl acetate (100 ML) and washed with saturated aqueous ammonium chloride (50 ML) then brine (50 ML). The organic extracts were suction-filtered through a plug of flash silica gel, washing with additional ethyl acetate (50 ML), and the solvents were evaporated under reduced pressure affording 1.37 g (94%) of the title compound as a tan oil; 1H-NMR (DMSO-d6, 200 MHz) δ: 8.39, 8.14, 7.98 (s, each 1H), 6.25 (bd, J=10.5 Hz, 1H), 6.10 (bd, J=10.2 Hz, 1H), 5.15 (m, 1H), 4.28 (m, 1H), 3.84 (m, 4H), 0.91 (s, 9H), 0.11, 0.97 (s, each 3H).

c) (3R,4S,5S,6R)-1-(6-((tert-butyldimethylsilyl)oxy)-tetrahydro-4,5-dihydroxy-2H-pyran-3-yl)-5,6-dichloro-1H-benzimidazole To a stirred solution of the olefin (part b of this example, 1.30 g, 3.14 mmol) in 30 ML of acetone-water (8:1) was added 4-methylmorpholine N-oxide (0.42 g, 3.45 mmol) followed by osmium tetroxide (0.60 ML of a 2.5% solution in tert-butanol). The reaction was stirred 24 h then treated with an additional 0.6 ML of osmium tetroxide solution and stirred an additional 24 h. The reaction mixture was concentrated and chromatographed on silica gel 60. The title compound eluted with 2% methanol-chloroform as a white glass, after evaporation of solvents (1.14 g, 81%); m.p. 128–130° C.; 1H-NMR (DMSO-d6, 200 MHz) δ: 8.52, 8.01, 7.98 (s, each 1s), 5.49 (d, J=4 Hz, 1H), 4.68 (d, J=6.7 Hz, 1H), 4.58 (m, 1H), 4.18 (m, 2H), 3.95 (m, 1H), 3.84 (m, 2H), 3.66 (m, 1H), 3.48 (m, 1H), 0.90 (s, 9H), 0.96, 0.07 (s, each 3H).

Anal. Calcd. for C19H28Cl2N2O4Si.1.0 H2O: C, 49.03; H, 6.50; N, 6.02; Cl, 15.23. Found: C, 49.03; H, 6.54; N, 5.98; Cl, 15.13.

d) (3R,4S,5S,6R)-5,6-dichloro-1-(tetrahydro-4,5-dihydroxy-6-hydroxymethyl)-2H-pyran-3-yl)-1H-benzimidazole A solution of (3R,4S,5S,6R)-1-(6-((tert-butyldimethylsilyl)oxy)-tetrahydro-4,5-dihydroxy-2H-pyran-3-yl)-5,6-dichloro-1H-benzimidazole (part c of this example, 1.08 g, 3.00 mmol) in THF (100 ML) and 1 N HCl (3 ML) was stirred overnight. The reaction mixture was concentrated under reduced pressure and the crude residue purified by flash chromatography on silica gel 60. The title compound eluted with 10% methanol-chloroform as a white crystalline solid, after evaporation of solvents 0.704 g, 88%); m.p. 160–162° C.; 1H-NMR (DMSO-d6, 200 MHz) δ: 8.59, 8.00 (s, each 1H), 5.46 (d, J=4.1 Hz, 1H), 4.72 (t, J=6.6 Hz, 1H), 4.73 (d, 1H), 4.58 (m, 1H), 4.15 (m, 2H), 3.96 (m, 1H), 3.70–3.39 (m, 4H).

Anal. Calcd. for C13H14Cl2N2O4.1.5 H2O: C, 43.35; H, 4.76, N, 7.78, Cl, 19.69. Found: C, 43.63; H, 4.60, N. 7.53, Cl, 19.94.

e) (3R,4S,5S,6R)-2-Bromo-5,6-dichloro-1-(4,5-diacetoxy-6-(acetoxymethyl)tetrahydro-2H-pyran-3-yl)-1H-benzimidazole To a stirred solution of (3R,4S,5S,6R)-5,6-dichloro-1-(tetrahydro-4,5-dihydroxy-6-(hydroxymethyl)-2H-pyran-3-yl)-1H-benzimidazole (part d of this example, 0.600 g, 1.80 mmol) in anhydrous pyridine (50 ml) was added acetic anhydride (2.00 ml, 21.0 mmol). After 12 hours the reaction mixture was concentrated under reduced pressure, coevaporating with toluene to a viscous oil. Ethanol (ca. 5 ml) was added (with external ice cooling) and the mixture was again coevaporated with toluene (2×) until acetic acid odor was absent. The oil was redissolved in chloroform (500 ml) and washed successively with 0.1 N HCl (100 ml), saturated aqueous sodium bicarbonate (100 ml), and brine (50 ml). The organic layer was dried (sodium sulfate) and suction-filtered through a plug (3×4 cm) of flash silica gel 60, washing with chloroform. Evaporation of the solvents under reduced pressure left an off-white foam (0.867 g, 1.89 mmol) which was dissolved in anhydrous tetrahydrofuran (Aldrich Sure Seal, 15 ml), heated to reflux under nitrogen with stirring, and N-bromosuccinimide (Aldrich, 0.670 g, 3.78 mmol) was added in one portion. After 10 min. at reflux, TLC on silica gel plates developed with 10% methanol-chloroform indicated the reaction was complete. The yellow solution was cooled to room temperature, diluted with chloroform (200 ML) and washed with saturated aqueous sodium bicarbonate (3×50 ML). The organic layer was dried (sodium sulfate), filtered, and concentrated under reduced pressure. The crude residue was purified by flash chromatography on silica gel 60. Elution with 2% methanol-chloroform afforded a yellow foam after removal of solvents. Trituration in ethanol-water and filtration gave the title compound as a white crystalline solid (0.98 g, 83%); m.p. 196–199° C.; 1H-NMR (DMSO-d6, 200 MHz) δ: 8.27, 8.00 (s, each 1H), 5.58 (dd, J=8.4, 3.1 Hz, 1H), 5.17 (t, J=2.8 Hz, 1H), 5.09 (m, 1H), 4.55–4.17 (m, 5H), 2.15, 2.04, 1.93 (s, each 3H).

Anal. Calcd. for C19H19BrCl2N2O7: C, 42.40; H, 3.56; N, 5.21; total halogen as Cl, 13.18. Found: C, 42.58; H, 3.64; N, 5.16; total halogen as Cl, 13.22.

f) (3R,4S,5S,6R)-2-Bromo-5,6-dichloro-1-(tetrahydro-4,5-dihydroxy-6-(hydroxymethyl)-2H-pyran-3-yl)-1H-benzimidazole (3R,4S,5S,6R)-2-Bromo-5,6-dichloro-1-(4,5-diacetoxy-6-(acetoxymethyl)tetrahydro-2H-pyran-3-yl)-1H-benzimidazole (part e of this example, 0.810 g, 1.53 mmol) was dissolved in 1:1 methanol-ethanol (100 ML) and treated with a solution of sodium carbonate (0.163 g, 1.53 mmol) in water (10 ML). After 0.5 h at room temperature, TLC analysis indicated a single new spot (silica gel, 10% methanol-chloroform). The pH was then adjusted to 5 with glacial acetic acid and the solvents evaporated in vacuo. The residual solid was slurried in water until the solids were free-flowing, then suction-filtered and dried overnight in vacuo affording the title compound as a white solid (0.510 g, 81%); m.p. 207–209° C.; [α]20D–162° (c 0.26, EtOH); 1H-NMR (DMSO-d6, 200 MHz) δ: 8.30, 8.28 (s, each 1H), 5.26 (d, J=5.5 Hz, 1H), 5.13 (d, J=4.2 Hz, 1H), 5.05 (t, J=4.7 Hz, 1H), 5.04 (m, 1H), 4.78 (m, 1H), 4.33–4.00 (m, 3H), 3.84–3.68 (m, 3H).

Anal. Calcd. for C13H13BrCl2N2O4: C, 37.89; H, 3.18; N, 6.80; total halogen as Cl, 17.20. Found: C, 38.08; H, 3.2; N, 6.86; total halogen as Cl, 17.15.

Example 41

(3R,4S ,5S ,6R)-5,6-Dichloro-2-(cyclopropylamino)-1-(tetrahydro-4,5-dihydroxy-6-(hydroxymethyl)-2H-pyran-3-yl)-1H-benzimidazole A solution of (3R,4S,5S,6R)-2-Bromo-5,6-dichloro-1-(tetrahydro-4,5-dihydroxy-6-(hydroxymethyl)-2H-pyran-3-yl)-1H-benzimidazole (Example 40, part e, 0.300 g, 0.728 mmol) and cyclopropyl amine (Aldrich, 2.50 ML, 36 mmol) in absolute ethanol (10 ML) was refluxed under nitrogen for 24 h. 1 N sodium hydroxide (0.73 ml) was added and the reaction mixture was concentrated under reduced pressure. The residual solids were chromatographed on silica gel 60. Title compound was eluted with 10% methanol-chloroform as a white foam, after evaporation of solvents (0.100 g, 34%); m.p. 244° C. (decomposition); [α]20D+6.4 (c 0.25, MeOH); 1H-NMR (DMSO-d6, 200 MHz) δ: 7.65, 7.41 (s, each 1H), 7.37 (bs, 1H), 5.33 (m, 1H), 4.91 (m, 2H), 4.36 (m, 1H), 4.10–3.90 (m, 3H), 3.69 (m, 3H), 2.80 (m, 1H), 2.45 (m, 1H), 0.72–0.51 (m, 4H).

Anal. Calcd. for C16H19Cl2N3O4.3.0 H2O: C, 43.10; H, 5.74; N, 9.42; Cl, 15.90. Found: C, 43.27; H, 5.56; N, 9.37; Cl, 15.64.

Example 42

(3S,4R,5R,6S)-2-Bromo-5,6-dichloro-1-(tetrahydro-4,5-dihydroxy-6-(hydroxymethyl)-2H-pyran-3-yl)-1H-benzimidazole The title compound was prepared in the same manner as the enantiomer described in example 40 starting from L-glucose-derived 2S,4-α-S,7S,8-α-R-perhydro-7-hydroxy-2-phenylpyrano(3,2-D)1,3)dioxin ((Tetrahedron Letters, 1996, 8147 and references cited therein), m.p. 207–208° C.; [α]20D +175 (c 0.25, EtOH); 1H-NMR (CDCl3, 200 Mhz) data was identical to that of the enantiomer.

Anal. Calcd. for C13H13BrCl2N2O4: C, 37.89; H, 3.18; N, 6.80; total halogen as Cl, 17.20. Found: C, 38.17; H, 3.24; N, 6.76; total halogen as Cl, 17.13.

Example 43

(3S,4R,5R,6S)-5,6-Dichloro-2-(cyclopropylamino)-1-(tetrahydro-4,5-dihydroxy-6-(hydroxymethyl)-2H-pyran-3-yl)-1H-benzimidazole The title compound was prepared in the same manner as the enantiomer (example 41) starting from L-glucose-derived 2S,4-α-S,7S,8-α-R-perhydro-7-hydroxy-2-phenylpyrano(3,2-D)1,3)dioxin ((Tetrahedron Letters, 1996, 8147 and references cited therein): m.p. 164° C.; [α]20D –8.4 (c 0.25, MeOH); 1H-NMR (CDCl3, 200 Mhz) identical to that reported in example 41.

Anal. Calcd. for C16H19Cl2N3O4.0.60 H2O: C, 48.16; H, 5.10, N, 10.53, Cl, 17.77. Found: C, 48.18; H, 5.05, N, 10.38, Cl, 17.65.

Example 44

(3S,4R,5R,6S)-5,6-Dichloro-2-(isopropylamino)-1-(tetrahydro-4,5-dihydroxy-6-(hydroxymethyl)-2H-pyran-3-yl)-1H-benzimidazole A solution of (3S,4R,5R,6S)-2-bromo-5,6-dichloro-1-(tetrahydro-4,5-dihydroxy-6-(Hydroxymethyl)-2H-pyran-3-yl)-1H-benzimidazole (Example 42, 0.328 g, 0.795 mmol) in isopropylamine (10 ml) was heated to 100° C. in a sealed tube overnight. 1 N sodium hydroxide (0.80 ml) was added and the reaction mixture was concentrated under reduced pressure. The residual solids were chromatographed on silica gel 60. Title compound was eluted with 2–10% methanol-chloroform as a white foam, after evaporation of solvents (0.15 g, 51%); m.p. 122° C.; [α]20D –23.6 (c 0.25, MeOH); 1H-NMR (DMSO-d6, 200 Mhz) δ7.59, 7.39 (s, each 1H), 7.15 (bs, 1H), 5.44 (m, 1H), 4.90 (m, 2H), 4.39 (m, 1H), 4.14–3.61 (m, 7H), 1.23 (d, J=6.4 Hz, 6H).

Anal. Calcd. for C16H21Cl2N3O.0.30 H2O.0.20 EtOH: C, 48.82; H, 5.66; N, 10.17; Cl, 17.16. Found: C, 48.84; H, 5.69; N, 10.08; Cl, 17.07.

Example 45

(±)-trans-2-(2-Bromo-5,6-dichloro-1H-benzimidazol-1-yl)cyclohexanol a) (±)-trans-2-(5,6-Dichloro-1H-benzimidazol-1-yl)cyclohexanol 5,6-Dichlorobenzimidazole (Townsend and Revankar, Chem. Rev. 1970, 70:389, and references cited therein) (5.00 g, 26.0 mmol) was dissolved in N,N-dimethylformamide (65 ml) and sodium hydride (60% oil dispersion, 50 mg) was added. The solution was heated to 145° and cyclohexene oxide (Aldrich, 7.8 g, 26 mmol) was added in 3 portions over 3 hours. The solution was neutralized with 1 N hydrochloric acid, and evaporated to a purple solid. The solid was recrystallized from ethanol to give title compound as pink crystals (12.55 g, 88%); m.p. 236–238° C.

Anal. Calcd. for C13H14Cl2N2O: C, 54.75; H, 4.95; N, 9.82; Cl, 24.86. Found: C, 54.91; H1, 4.84; N, 9.80; Cl, 24.93.

b) (±)-trans-2-(5,6-Dichloro-1H-benzimidazol-1-yl)cyclohexyl Acetate (±)-trans-2-(5,6-Dichloro-1H-benzimidazol-1-yl)cyclohexanol (part a of this example, 6.25 g, 21.9 mmol) was stirred in acetic anhydride (3 ml)-pyridine (50 ml) for 18 h. Volatiles were evaporated and the residue partitioned between chloroform and saturated aqueous sodium bicarbonate. The chloroform solution was filtered through Celite/charcoal and evaporated to give title compound as an off-white solid (6.92 g, 97%), m.p. 145–147° C.

Anal. Calcd. for C15H16Cl2N2O2: C, 55.00; H, 4.93; N, 8.56; Cl, 21.67. Found: C, 55.15; H, 4.88; N, 8.64; Cl, 21.77.

c) (±)-trans-2-(2-Bromo-5,6-dichloro-1H-benzimidazol-1-yl)cyclohexyl Acetate (±)-Trans-2-(5,6-dichloro-1H-benzimidazol-1-yl)cyclohexyl acetate (part b of this example, 6.62 g, 20.2 mmol) in tetrahydrofuran (120 ml) was refluxed while N-bromosuccinimide (7.20 g, 40.5 mmol) was added in one portion. Reflux was continued for 10 minutes. The solution was cooled and diluted with chloroform (200 ml). The chloroform solution was extracted with aqueous sodium bicarbonate, then water, and dried (sodium sulfate). Evaporation of volatiles in vacuo left white crystals, after trituration from ethyl acetate-hexanes (5.77 g, 70%), m.p. 167–169° C.

Anal. Calcd. for C15H15BrCl2N2O2: C, 44.37; H, 3.72; N, 6.90; total halogen as Cl, 26.19. Found: C, 44.41; H,3.69; N, 6.84; total halogen as Cl, 26.19.

d) (±)-Trans-2-(2-bromo-5,6-dichloro-1H-benzimidazol-1-yl)cyclohexanol (±)-Trans-2-(2-bromo-5,6-dichloro-1H-benzimidazol-1-yl)cyclohexyl acetate (part c of this example, 500 mg, 1.23 mmol) was dissolved in methanol half-saturated with ammonia (at 0° C.) and the solution stirred at room temperature for 18 hours. Volatiles were evaporated and the residual solid recrystallized from methanol-water to give title compound as white crystals (350 mg, 78%), m.p. 186–188° C.; 1H-NMR (DMSO-d6, 200 MHz) δ: 8.23, 7.93 (both s, each 1, 2 aromatic CH), 4.99 (d, J=4.7 Hz, 1, OH), 4.34.1 (m, 2, OCH and NCH), 2.4–1.3 (m, 8, 4CH2).

Anal. Calcd. for C13H13BrCl2N2O: C, 42.89; H, 3.60; N, 7.70; total halogen as Cl, 29.21. Found: C, 42.99; H,3.68; N, 7.61; total halogen as Cl, 29.14.

e) Separation of the Enantiomers of (±)-Trans-2-(2-bromo-5,6-dichloro-1H-benzimidazol-1-yl)cyclohexanol The enantiomers of (±)trans-2-(2-bromo-5,6-dichloro-1H-benzimidazol-1-yl)cyclohexanol were separated on a Rainin preparative chiral HPLC instrument using a 2 cm Chiralpak® AD amylose column (Chiral Technology Inc., Exton, Pa.). Using a mobile phase of 90% hexanes-10% isopropyl alcohol and a flow rate of 6.0 ml/min, the enantiomers were eluted with retention times of 10.40 and 13.68 min. Fractions containing each peak were pooled and solvents evaporated. Each enantiomer was shown to be free of the other by analytical chiral HPLC on an analytical Chiralpak® AD amylose column (Chiral Technology Inc., Exton, Pa.). The enantiomer with a retention time of 10.40 min was isolated, after evaporation of solvents and drying at 0.1 mm Hg, as white powder, m.p. 206–207° C.; 1H-NMR (DMSO-d6, 200 Mhz) identical with that of the racemate described in part d of this example.

Anal. Calcd. for C13H13BrCl2N2O.0.225 hexanes: C, 44.95; H, 4.25; N, 7.31; total halogen as Cl, 27.74. Found: C, 45.00; H,4.02; N, 7.26; total halogen as Cl, 27.59.

The enantiomer with a retention time of 13.79 min was isolated, after evaporation of solvents and drying at 0.1 mm Hg, as white powder, m.p. 201–202° C.; 1H-NMR (DMSO-d6, 200 Mhz) identical with that of the racemate described in part d of this example.

Anal. Calcd. for C13H13BrCl2N2O.0.285 hexanes: C, 45.46; H, 4.41; N, 7.21; total halogen as Cl, 27.37. Found: C, 45.67; H,4.13; N, 7.17; total halogen as Cl, 27.07.

Example 46

(±)-trans-2-[5,6-Dichloro-2-(cyclopropylamino)-1H-benzimidazol-1-yl]cyclohexanol (±)trans-2-(2-Bromo-5,6-dichloro-1H-benzimidazol-1-yl)cyclohexyl acetate (Example 45, part c, 1.00 g, 2.46 mmol) and cyclopropylamine (5.0 ml) were refluxed in absolute ethanol (15 ml) for 3 days. The solution was cooled and 1 N sodium hydroxide (2.4 ml) was added. The residual solid was crystallized from ethanol-water to provide title compound as off-white powder (0.56 g, 67%), m.p. 149–151° C.; 1H-NMR (DMSO-d6, 200 MHz) δ: 7.55, 7.39 (both s, each 1, 2 aromatic CH), 6.90 (m, 1, NH), 4.73 (d, J=5.2 Hz, 1, OH), 4.1–3.8 (m, 2, OCH and NCH), 2.8–2.65 (m, 1, CHNH), 2.2–1.9 and 1.8–1.2 (m, 8, 4 CH2), 0.75–0.45 (m, 4, 2 cyclopropyl CH2).

Anal. Calcd. for C16H19Cl2N3O: C, 55.89; H, 5.69; N, 12.22; Cl, 20.62. Found: C, 55.90; H,5.78; N, 12.22; Cl, 20.67.

Example 47

(±)-(1R*,2S*,3R*)-3-(2-Bromo-5,6-dichloro-1H-benzimidazol-1-yl)-1,2-cyclohexanediol a) (±)-(1R*,2S*,3R*)-3-(4,5-Dichloro-2-nitroanilino)-1,2-cyclohexanediyl Diacetate (±)-(1R*,2S*,3R*)-3-Aminocyclohexane-1,2-diol hydrochloride (Tetrahedron Letters 1984, 25: 3259) (6.42 g, 38.3 mmol) was refluxed in t-butyl alcohol (50 ml) with anhydrous potassium carbonate (Aldrich, 16.2 g, 0.115 mole as 98%) and 1,2,4-trichloro-5-nitrobenzene (9.10 g, 39 mmol as 97%) for 2 days. Volatiles were evaporated and the residue chromatographed on silica get. Elution with 1% methanol-chloroform gave the major product as a yellow powder (4.77 g, 39%), after crystallization from ethanol-water. This material was stirred in pyridine (45 ml)—acetic anhydride (8.4 ml) for 2 days. Volatiles were evaporated and the residue chromatographed on silica gel. Title compound was eluted with chloroform to give, after crystallization from ethyl acetate-hexanes, orange crystals (4.30 g, 71%, m.p. 178–180° C. dec.

Anal. Calcd. for C16H18Cl2N2O6: C, 47.42; H, 4.48; N, 6.91; Cl, 17.50. Found: C, 57.50; H, 4.47; N, 6.90; Cl, 17.41.

b) (±)-(1R*,2S*,3R*)-3-(5,6-Dichloro-1H-benzimidazol-1-yl)-1,2-cyclohexanediyl Diacetate (±)-(1R*,2S*,3R*)-3-(4,5-Dichloro-2-nitroanilino)-1,2-cyclohexanediyl diacetate (part a of this example, 5.65 g, 13.9 mmol) in n-propanol (250 ml) was shaken with Raney nickel (Aldrich, ca. 0.50 g) under hydrogen (50 psi) for 2 h. Filtration through Celite and evaporation of solvent left the 5,6-diaminobenzimidazole intermediate. Triethylorthoformate (250 ml) and 4 drops of methanesulfonic acid were added and the solution stirred at room temperature for 2 days. Volatiles were evaporated in vacuo and the residual material chromatographed on silica gel. Title compound eluted with 2% methanol-ethyl acetate as off-white solid (1.87 g, 35%), m.p. 163–165° C. Anal. Calcd. for C17H18Cl2N2O4: C, 53.00; H, 4.71; N, 7.27; Cl, 18.41. Found: C, 52.85; H, 4.72; N, 7.17; Cl, 18.35.

c) (±)-(1R*,2S*,3R*)-3-(2-Bromo-5,6-dichloro-1H-benzimidazol-1-yl)-1,2-cyclohexanediyl Diacetate (±)-(1R*,2S*,3R*)-3-(5,6-Dichloro-1H-benzimidazol-1-yl)-1,2-cyclohexanediyl diacetate (part b of this example, 1.58 g, 4.10 mmol) was dissolved in dry N,N-dimethylformamide (6.4 ml) and maintained at 65° C. under nitrogen while N-bromosuccinimide (1.46 g, 8.2 mmol) was added in 2 portions over 1 h. Volatiles were evaporated in vacuo and the residue was chromatographed on silica gel. Title compound was eluted with ethyl acetate as an off-white powder (0.95 g, 49%), m.p. 71–79° C.

Anal. Calcd. for C17H17BrCl2N2O4: C, 43.99; H, 3.69; N, 6.04; total halogen as Cl, 22.92. Found: C, 44.04; H, 3.83; N, 6.01; total halogen as Cl, 22.85.

d) (±)-(1R*,2S*,3R*)-3-(2-Bromo-5,6-dichloro-1H-benzimidazol-1-yl)-1,2-cyclohexanediol (±)-(1R*,2S*,3R*)-3-(2-Bromo-5,6-dichloro-1H-benzimidazol-1-yl)-1,2-cyclohexanediyl diacetate (part c of this example, 700 mg, 1.51 mmol) was dissolved in ethanol (12 ml)-methanol (12 ml)-water (3 ml). Sodium carbonate (160 mg, 1.5 mmol) was added and the mixture was stirred vigorously for 3 h. Volatiles were evaporated in vacuo and the residual solids were slurried in water. The solid was recrystallized from ethanol to give title compound as white powder (260 mg, 45%), m.p. 197–199° C. dec.; 1H-NMR (DMSO-d6, 200 MHz) δ: 8.26 and 7.92 (both s, each 1, 2 aromatic CH), 4.8–4.6 (m, 3, OCH and 2OH), 4.264.20 (m, 1, NCH), 4.17–3.98 (m, 1, OCH), 2.24–2.19 (m, 1, 1/2 CH2), 1.84–1.74 (m, 4, 2 CH2), 1.60–1.53 (m, 4, 1, 1/2 CH2).

Anal. Calcd. for C13H13BrCl2N2O2: C, 41.08; H, 3.45; N, 7.37; total halogen as Cl, 27.98. Found: C, 41.18; H, 3.49; N, 7.31; total halogen as Cl, 27.92.

e) Separation of the Enantiomers of (±)-(1R*,2S*,3R*)-3-(2-Bromo-5,6-dichloro-1H-benzimidazol-1-yl)-1,2-cyclohexanediol The enantiomers of (±)-(1R*,2S*,3R*)-3-(2-bromo-5,6-dichloro-1H-benzimidazol-1-yl)-1,2-cyclohexanediol were separated on a Rainin preparative chiral HPLC instrument using a 2 cm Chiralpak® AD amylose column (Chiral Technology Inc., Exton, Pa.). Using a mobile phase of 90% hexanes-10% isopropyl alcohol and a flow rate of 6.0 ml/min, the enantiomers were eluted with retention times of 14.28 and 19.25 min. Fractions containing each peak were pooled and solvents evaporated. Each enantiomer was shown to be free of the other by analytical chiral HPLC on an analytical Chiralpak® AD amylose column (Chiral Technology Inc., Exton, Pa.). After evaporation of solvents and drying at 0.1 mm Hg, both enantiomers were isolated as white powders, m.p. 200° C. dec.; 1H-NMR (DMSO-d6, 200 Mhz) identical with that of the racemate described in part d of this example.

Example 48

(±)-(1R*,2S*,3R*)-3-[5,6-Dichloro-2-(cyclopropylamino)-1H-benzimidazol-1-yl]-1,2-cyclohexanediol (±)-(1R*,2S*,3R*)-3-(2-Bromo-5,6-dichloro-1H-benzimidazol-1-yl)-1,2-cyclohexanediyl diacetate (464 mg, 1.00 mmol) and cyclopropylamine were reacted as in example 46. The solution was cooled and 1 N sodium hydroxide (one equivalent) was added. Volatiles were evaporated in vacuo and the residual solid was crystallized from methanol to provide title compound as off-white powder (271 mg, 76%), m.p. >25° C.; 1H-NMR (DMSO-d6, 200 MHz) δ: 7.62, 7.44 (both s, each 1, 2 aromatic CH), 7.00–6.95 (m, 1, NH), 4.66 (d, J=6.2 Hz, 1, OH), 4.56 (d, J=2.7 Hz, 1, OH), 4.3–3.9 (m, 3, 2 OCH and NCH), 2.8–2.65 (m, 1, NCH), 2.1–1.4 (m, 6, 3 CH2), 0.75–0.45 (m, 4, 2 CH2 of cyclopropyl).

Anal. Calcd. for C16H19Cl2N3O: C, 54.09; H, 5.39; N, 11.83; Cl, 19.69. Found: C, 53.81; H,5.44; N. 11.60; Cl, 19.98.

Example 49

(±)-(1R*,2S*,4R*)-4-(2-Bromo-5,6-dichloro-1H-benzimidazol-1-yl)cyclohexane-1,2-diol (a) (±)-{1-[2-(Trimethylsilyl)ethyl]oxycarbonylamino}cyclohex-3-ene Diphenylphosphoryl azide (8.58 ml, 39.64 mmol) was added to triethylamine (5.52 ml, 39.64 mmol) in toluene (80 ml) and the reaction was heated to 75° C. Then, (±)-cyclohex-3-enecarboxylic acid (5.00 g, 39.64 mmol) in toluene (20 ml) was added dropwise and the reaction was stirred for 1 hr. Then, 2-(trimethylsilyl)ethanol (6.53 ml, 47.56 mmol) was added and the reaction was stirred at 60° C. for 17 hr. The reaction was cooled and 1.0 N sodium hydroxide added. The mixture was extracted with ethyl acetate, dried with magnesium sulfate, filtered, and concentrated. The residue was purified by column chromatography eluting with ethyl acetate:hexanes (1:9) to give the title compound (7,46 g, 78%). Rf=0.40 (1:4 ethyl acetate:hexanes); 1H-NMR (CDCl3, 300 MHz) δ5.67–5.55 (m, 2H), 4.59 (br s, 1H), 4.12 (t, 2H, J=8), 3.80 (s, 1H), 2.36 (d, 1H, J=7), 2.09 (m, 2H), 1.89–1.81 (m, 2H), 1.57–1.48 (m, 1H), 0.95 (t, 2H, J=8), 0.01 (s, 9H); MS (ES) M+Na= 264.

(b) (±)-(1R*,3S*,5R*)-(2-Nitro-4,5-dichlorophenyl)-(2,2-dimethyl-hexahydro-benzo-1,3-dioxol-5-yl)amine and (±)-(1S*,3R*,5R*)-(2-nitro-4,5-dichlorophenyl)-(2,2-dimethyl-hexahydro-benzo-1,3-dioxol-5-yl)amine 4-Methylmorpholine N-oxide (4.85 g, 41.42 mmol) was added to (±)-{1-[2-(trimethylsilyl)ethyl]oxycarbonylamino}cyclohex-3-ene (part a of this experiment (10.00 g, 41.42 mmol) in acetone:water (9:1, 83 ml), then osmium tetroxide (10.5 mg, 41.4 mmol) was added and the reaction was stirred for 15 hr and concentrated. The residue was purified by column chromatography eluting with ethyl acetate to give the diols as a mixture of isomers (1:1) (10.53 g, 93%). The product was taken up in acetone (192 ml) and pyridinium para-toluenesulfonate (960.8 mg, 3.82 mmol) was added. The reaction was heated at reflux for 19 hr, cooled, and concentrated. The residue was purified by column chromatography eluting with ethyl acetate:hexanes (2:3) to give the acetonides (9.20 g, 76%). The residue was taken up in acetonitrile (146 ml) and tetraethylammonium fluoride hydrate (5.37 g, 32.08 mmol) was added. The mixture was heated at reflux for 19 hr, cooled, and concentrated. The residue was taken up in dioxane (146 ml) and potassium carbonate (8.06 g, 58.32 mmol) was added. Then, 2-fluoro-4,5-dichloronitrobenzene (6.43 g, 30.62 mmol) was added and the reaction was heated at 70° C. for 66 hr. The mixture was cooled, brine added, extracted with ethyl acetate, dried with magnesium sulfate, filtered, and concentrated. The residue was purified by column chromatography eluting with ethyl acetate:hexanes (1:4) to give the title compounds (8.54 g, 81%). Rf=0.24 (1:4 ethyl acetate:hexanes); 1H-NMR (CDCl3, 300 MHz) δ8.26 (s, 1H), 7.92 (d, 1H, J=7), 6.99 (s, 1H), 4.34 (m, 1H), 4.17 (q, 1H, J=8), 3.78 (m, 1H), 2.41 (d, 1H, J=14), 2.15–2.00 (m, 1H), 1.97–1.88 (m, 1H), 1.84–1.62 (m, 2H), 1.55 (s, 3H), 1.40–1.32 (m, 1H), 1.35 (s, 3H); MS (ES) M+Na=384. Rf=0.15 (1:4 ethyl acetate hexanes); 1H-NMR (CDCl3, 300 MHz) d 8.57 (d, 1H, J=7), 8.27 (s, 1H), 6.89 (s, 1H), 4.29 (q, 1H, J=5), 4.16 (q, 1H, J=6), 3.66 (m, 1H), 2.10 (m, 2H), 1.91–1.67 (m, 4H), 1.57 (s, 3H), 1.36 (s, 3H); MS (ES) M+H=361.

(c) (±)-(1R*,3S*,5R*)4,5-Dichloro-N-[2,2-dimethyl-hexahydro-benzo(1,3)dioxol-5-yl]-benzene-1,2-diamine Raney nickel (1.21 g, 100 wt %) was added to (±)-(1R*, 3S*,5R*)-(2-nitro-4,5-dichlorophenyl)-(2,2-dimethyl-hexahydro-benzo-1,3-dioxol-5-yl)amine and (±)-(1S*,3R*, 5R*)-(2-nitro-4,5-dichloro-phenyl)-(2,2-dimethyl-hexahydro-benzo-1,3-dioxol-5-yl)amine (part b of this example, 1.21 g, 3.35 mmol) in methanol (17 ml) at rt under an argon atmosphere. The reaction was fitted with a hydrogen balloon, repeatedly evacuated and purged with hydrogen, then allowed to stir for 3 hr. The reaction was purged with nitrogen, filtered through Celite®, and concentrated. The residue was purified by column chromatography eluting with ethyl acetate:hexanes (3:2) to give the title compound (720 mg, 65%). Rf=0.29 (3:2 ethyl acetate:hexanes); 1H-NMR (CD3OD, 300 MHz) δ6.74 (s, 1H), 6.58 (s, 1H), 4.36 (q, 1H, J=5), 4.18–4.12 (m, 1H), 3.57–3.47 (m, 1H), 2.33 (d, 1H, J=15), 2.00–1.86 (m, 2H), 1.74–1.59 (m, 2H), 1.52 (s, 3H), 1.33 (s, 3H), 1.30–1.22 (m, 1H); MS (ES) M+H 331.

(d) (±)-[1R*,3S*,5R*)-5,6-Dichloro-1-(2,2-dimethyl-hexahydro-benzo[1,3]dioxol-5-yl)-1H-benzimidazole (±)-(1R*,3S*,5R*)4,5-Dichloro-N-[2,2-dimethyl-hexahydro-benzo(1,3)dioxol-5-yl]-benzene-1,2-diamine (part c of this experiment, 720 mg, 2.17 mmol) was taken up in triethyl orthoformate (11 ml) and the reaction was heated at 80° C. for 14 hr and concentrated. The residue was purified by column chromatography eluting with methanol:ethyl acetate (1:99) to give the title compound (673.1 mg, 91%). Rf=0.23 (ethyl acetate); 1H-NMR (CD3OD, 300 MHz) δ8.37 (s, 1H), 7.88 (s, 1H), 7.81 (s, 1H), 4.71–4.63 (m, 1H), 4.49–4.45 (m, 1H), 4.30–4.24 (m, 1H), 2.50–2.44 (m, 1H), 2.36–2.26 (m, 1H), 2.12–2.01 (m, 2H), 1.97–1.83 (m, 2H), 1.57 (s, 3H), 1.36 (s, 3H); MS (ES) M+H=341.

(e) (±)-(1R*,2S*,4R*)-4-(5,6-Dichloro-1H-benzimidazol-1-yl)cyclohexane-1,2-diol

Pyridinium para-toluenesulfonate (33.6 mg, 134.7 mmol) was added to (±)-5,6-dichloro-1-(2,2dimethyl-hexahydro-benzo[1,3]dioxol-5-yl)-1H-benzimidazole (part d of this experiment, 459.6 mg, 1.35 mmol) in methanol (7 ml) and the reaction was heated at reflux for 19 hr and concentrated. The residue was purified by column chromatography eluting with methanol:ethyl acetate (1:9) to give the title compound (184.4 mg, 45%). Rf=0.19 (1:9 methanol:ethyl acetate); 1H-NMR (CD3OD, 300 MHz) δ8.36 (s, 1H), 7.91 (s, 1H), 7.80 (s, 1H), 4.70 (tt, 1H, J=12, 4), 4.11 (d, 1H, J=3), 3.79–3.73 (m, 1H), 2.26 (dq, 1H, J=13, 3), 2.15–2.10 (m, 2H), 2.06–1.99 (m, 2H), 1.88–1.85 (m, 1H); MS (ES) M+H=301.

(f) (±)-[1R*,3S*,5R*]-2-Bromo-5,6-dichloro-1-(2,2-dimethyl-hexahydro-benzo[1,3]dioxol-5-yl)-1H-benzimidazole N-bromosuccinimide (702 mg, 3.94 mmol) was added to (±)-(1R*,2S*,4R*)-4-(5,6-dichloro-1H-benzimidazol-1-yl)

cyclohexane-1,2-diol (part e of this example, 673.1 mg, 1.97 mmol) in tetrahydrofuran (20 ml) at reflux and the reaction was stirred for 15 min. The mixture wag poured into ice water, saturated sodium bicarbonate added, extracted with ethyl acetate, dried with magnesium sulfate, filtered, and concentrated. The residue was purified by column chromatography eluting with ethyl acetate:hexanes (2:3) to give the title compound (187.7 mg, 23%) and recovered starting material (459.6 mg, 68%). Rf=0.35 (2:3 ethyl acetate:hexanes); 1H-NMR (CDCl3, 300 MHz) δ7.78 (s, 1H), 7.49 (s, 1H), 4.96–4.92 (m, 1H), 4.50–4.48 (m, 1H), 4.39–4.33 (m, 1H), 2.39 (dt, 1H, J=14, 3), 2.16–1.92 (m, 5H), 1.60 (s, 3H), 1.38 (s, 3H); MS (ES) M+H=421.

(g) (±)-(1R*,2S*,4R*)-4-(2-Bromo-5,6-dichloro-1H-benzimidazol-1-yl)cyclohexane-1,2-diol Pyridinium para-toluenesulfonate (part f of this example, 11.2 mg, 44.7 mmol) was added to (±)-[1R*,3S*,5R*]-2-bromo-5,6-dichloro-1-(2,2-dimethyl-hexahydro-benzo[1,3]dioxol-5-yl)-1H-benzimidazole (part f of this example, 187.7 mg, 446.8 mmol) in methanol (9 ml) and the reaction was heated at reflux for 14 hr and concentrated. The residue was purified by column chromatography eluting with methanol:ethyl acetate (1:99) to give the title compound (130.2 mg, 77%). Rf=0.23 (ethyl acetate); 1H-NMR (CD3OD, 300 MHz) δ7.98 (s, 1H), 7.73 (s, 1H), 5.03 (tt, 1H, J=13, 4), 4.12 (s, 1H), 3.86 (dt, 1H, J=11, 4), 2.54 (dt, 1H, J=13, 2), 2.38 (dq, 1H, J=13, 5), 2.05–1.83 (m, 4H); MS (ES) M+H=381.

Example 50

(±)(1R*,2S*,4R*)-4-(2-Isopropylamino-5,6-dichloro-1H-benzimidazol-1-yl)cyclohexane-1,2-diol Isopropylamine (99.5 mg, 1.68 mmol) was added to (±)-(1R*,2S*,4R*)-4-(2-bromo-5,6-dichloro-1H-benzimidazol-1-yl)cyclohexane-1,2-diol (Example 49, part g, 64.0 mg, 168.4 mmol) in ethanol (3.4 ml) and the reaction was heated at 100° C. in a sealed tube for 67 hr. The reaction was cooled, saturated sodium carbonate added, extracted with ethyl acetate, dried with magnesium sulfate, and concentrated. The residue was purified by column chromatography eluting with methanol:ethyl acetate (1:19) to give the title compound (47.9 mg, 79%). Rf=0.24 (1:19 methanol:ethyl acetate); 1H-NMR (CD3OD, 300 MHz) δ7.46 (s, 1H), 7.31 (s, 1H), 4.44 (tt, 1H, J=13, 4), 4.11 (s, 1H), 4.05 (h, 1H, J=7), 3.82 (dt, 1H, J=10,4), 2.41 (dt, 1H, J=13,2), 2.26 (dq, 1H, J=13,4), 2.04–1.75 (m, 4H), 1.29 (d, 6H, J=6); MS (ES) M+H=358.

Example 51

(±)-(1S*,2R*,4R*)-4-(2-Bromo-5,6-dichloro-1H-benzimidazol-1-yl)-cyclohexane-1,2-diol (a) (±)-(1S*,2R*,4R*)-4-(5,6-Dichloro-1H-benzimidazol-1-yl)cyclohexane 1,2-diol Raney nickel (1.81 g, 25 wt %) was added to (±)-(1R*,3S*,5R*)-(2-nitro-4,5-dichlorophenyl)-(2,2-dimethyl-hexahydro-benzo-1,3-dioxol-5-yl)amine and (±)-(1S*,3R*,5R*)-(2-nitro-4,5-dichlorophenyl)-(2,2-dimethyl-hexahydro-benzo-1,3-dioxol-5-yl)amine (Example 49, part b, 7.25 g, 20.07 mmol) in methanol (100 ml) at rt under an argon atmosphere. The reaction was fitted with a hydrogen balloon, repeatedly evacuated and purged with hydrogen, then allowed to stir for 15 hr. The reaction was purged with nitrogen, filtered through Celite®, and concentrated. The residue was purified by column chromatography eluting with methanol ethyl acetate (1:99) to give the benzimidazolediol (2.88 g, 49%) as well as the other isomer. The residue was taken up in triethyl orthoformate (49 ml) and the reaction was heated at 80° C. for 17 hr and concentrated. The residue was purified by column chromatography eluting with methanol:ethyl acetate (1:19) to give the residue as a mixture of ortho ester isomers (3.39 g, 96%). Part of the residue (1.04 g, 2.91 mmol) was taken up in 1.0 N hydrochloric acid:tetrahydrofuran (1:1, 14.6 ml) and the reaction was stirred for 16 hr. Then, saturated sodium carbonate was added, the mixture was extracted with ethyl acetate, dried with magnesium sulfate, filtered, and concentrated. The residue was purified by column chromatography eluting with methanol:ethyl acetate (1:9) to give the title compound (753.2 mg, 86%). Rf=0.19 (1:9 methanol:ethyl acetate); 1H-NMR (CD3OD, 300 MHz) δ8.35 (s, 1H), 7.92 (s, 1H), 7.81 (s, 1H), 4.48 (tt, 1H, J=12, 4), 3.99 (d, 1H, J=3), 3.79 (dt, 1H, J=11, 4), 2.29 (q, 1H, J=12), 2.18 (dq, 1H, J=13, 4), 2.08–1.97 (m, 2H), 1.86–1.66 (m, 2H); MS (ES) M+H=301.

(b) (±)-(1S*,2R,4R*)-4-(2-Bromo-5,6-dichloro-1H-benzimidazol-1-yl)cyclohexane-1,2-diol Triethylamine (694.7 mg, 6.86 mmol) was added to (±)-(1S*,2R*,4R*)-4-(5,6-dichloro-1H-benzimidazol-1-yl)cyclohexanol-1,2-diol (part a of this example, 689.2 mg, 2.29 mmol) in methylene chloride (23 ml). Then, 4-dimethylaminopyridine (28.2 mg, 0.23 mmol) was added, followed by acetic anhydride (475.0 ml, 5.03 mmol) and the reaction was stirred for 14 hr. The mixture was quenched with sodium carbonate, extracted with methylene chloride, dried with magnesium sulfate, filtered, and concentrated. The residue was purified by column chromatography eluting with ethyl acetate:hexanes (9:1) to give the acetates (834.2 mg, 95%). The residue was taken up in tetrahydrofuran (20 ml) and N-bromosuccinimide (706.2 mg, 3.97 mmol) was added to the mixture at reflux. After 15 min, the mixture was poured into ice water, saturated sodium bicarbonate added, extracted with ethyl acetate, dried with magnesium sulfate, filtered, and concentrated. The residue was purified by column chromatography eluting with ethyl acetate:hexanes (1:1) to give bromide (623.2 mg, 68%). The residue was taken up in dioxane:water (1:1, 9 ml), lithium hydroxide monohydrate (316.6 mg, 7.54 mmol) added, and stirred for 3 hr. The mixture was extracted with ethyl acetate, dried with magnesium sulfate, filtered, and concentrated. The residue was purified by column chromatography eluting with methanol:ethyl acetate (1:99) to give the title compound (326.3 mg, 91%). Rf=0.26 (ethyl acetate); 1H-NMR (CD3OD, 300 MHz) δ8.01 (s, 1H), 7.75 (s, 1H), 4.68 (tt, 1H, J=13, 4), 4.00 (s, 1H), 3.80–3.73 (m, 1H), 2.67–2.43 (m, 2H), 2.05–1.98 (m, 1H), 1.91–1.86 (m, 1H), 1.73–1.62 (m, 2H); MS (ES) M+H=381.

Example 52

(+)-(1S*,2R*,4R* )-4-(2-Isopropylamino-5,6-dichloro-1H-benzimidazol-1-yl)cyclohexane-1,2-diol Isopropylamine (227.8 mg, 3.85 mmol) was added to (±)-(1S*,2R*,4R*)-4-(2-bromo-5,6-dichloro-1H-benzimidazol-1-yl)cyclohexane-1,2-diol (Example 51, part b, 146.5 mg, 385.4 mmol) in ethanol (3.9 ml) and the reaction was heated at 100° C. in a sealed tube for 68 hr. The reaction was cooled, saturated sodium carbonate added, extracted with ethyl acetate, dried with magnesium sulfate, and concentrated. The residue was purified by column chromatography eluting with methanol:ethyl acetate (1:19) to give the title compound (104.1 mg, 75%). Rf=0.20 (1:19 methanol:ethyl acetate); 1H-NMR (CD3OD, 300 MHz) δ7.53 (s, 1H), 7.36 (s, 1H), 4.31 (tt, 1H, J=13, 4), 4.06 (h, 1H, J=7), 3.97 (s, 1H), 3.75–3.68 (m, 1H), 2.50 (q, 1H, J=12), 2.39 (dq, 1H, J=13, 4), 2.02–1.96 (m, 1H), 1.78–1.49 (m, 3H), 1.29 (d, 3H, J=7), 1.28 (d, 3H, J=7); MS (ES) M+H=358.

Example 53

2-Bromo-5,6-dichloro-1-(4-deoxy-β-D-erythro-pentopyranosyl)-1H-benzimidazole

2-Bromo-5,6-dichloro-benzimidazole (0.5g, 1.9 mmoles) which can be prepared by the method of Townsend and Drach (U.S. Pat. No. 5,248,672) was added to 1,2-dichloroethane (Aldrich, Sure Seal, 35 ml). N,O-Bis (trimethylsilyl)acetamide (0.23 ml, 0.95 mmoles, 1 eq.) was added and the reaction heated to reflux for thirty minutes in a 95° C. oil bath. 4-Deoxy-1-methoxy-2,3-diacetyl-D-erythro-pentopyranoside (0.5g, 2.1 mmoles) which can be prepared by the method of Kinoshita, et. al. (Carbohydrate Research, 1982, 102, 298–301) was boiled in toluene to remove water. The excess toluene was removed in vacuo and the residue dissolved in 1,2-dichloroethane (15 ml). The carbohydrate solution was added to the reaction followed by trimethylsilyl trifluoromethanesulfonate (0.5 ml, 2.3 mmoles, 1.2 eq.). The reaction was heated for 18 hrs. Ice water (100 ml) was added. The organic layer was collected and washed with saturated sodium bicarbonate followed by brine. The organic solution was dried with $MgSO_4$, filtered, and the solvent removed in vacuo. The product was purified by chromatography on a 2.5×10 cm column of silica gel eluted with chloroform/methanol (98:2, v/v). The product containing fractions were combined and the solvents removed in vacuo. A 65% yield of 2-Bromo-5,6-dichloro-1-(4-deoxy-2,3-diacetyl-β-D-erythro-pentopyranosyl)-1H-benzimidazole was obtained. MS (GC-Cl+): m/z, 465, $M+H^+$. A portion of the diacetyl compound (0.11 g, 0.24 mmoles) was deblocked by treatment in $EtOH/H_2O$ (1/1, v/v, 16 ml) with $Na_2CO_3$ (0.1g, 0.95 mmoles, 4 eq.) at rt for 1 hr. The product was purified by chromatography on a 4×6.5 cm column of silica gel eluted with ethyl acetate/hexane (1:1, v/v). MS (GC-Cl+): m/z, 381, $M+H^+$. $^1H$ NMR (DMSO-$d_6$) δ7.98 (s, 1H, aryl), 7.92 (s,1H, aryl), 5.67 (d, 1H, H-1', $J_{1',2'b}$ =9 Hz), 5.18(bs, 1H, OH), 5.02 (bs, 1H, OH), 4.06 (m, 2H, H-2',3'), 3.8 (m, 2H, H-5'), 2.1 (m, 1H, H-4'), 1.67 (m, 1H, H4').

Example 54

1-(2,3,4-Tri-O-acetyl-α-L-lyxopyranosyl)-2,5,6-trichlorobenzimidazole

A three-necked 100 ml round bottom flask with a stirrer was charged with 2,5,6-trichlorobenzimidazole (which may be prepared in accordance with the methods described in PCT specifications WO92/07867, 354 mg; 1.6 mmol) and the system evacuated and backflushed with argon. Dry acetonitrile (40 ml) was added to this suspension followed by the addition of N,O-bis(trimethylsilyl)acetamide (325 mg, 1.6 mmol). To the stirred solution was added 1,2,3,4-tetra-O-acetyl-α-L-lyxopyranoside (M. Fuertes, J. T. Witkowski and R. K. Robins, J. Org. Chem., 40, (1975), pp. 2372–2377, 488 mg, 1.53 mmol) followed immediately by the addition of trimethylsilyl trifluoromethanesulfonate (466 mg, 2.1 mmol) via a gastight syringe. The reaction was continued at room temperature for 18 hours. The solvent was evaporated in vacuo to yield a yellow oil which was subjected to column chromatography (silica, 40×200 mm, 2% methanol in dichloromethane). The appropriate fractions were combined to yield 303 mg (42.7%) of the title compound as a white foam. $^1H$ NMR (DMSO-$d_6$; 200 MHz) δ8.012 (s, 1H), 6.013 (d, 1H, J=9.4 Hz), 5.502 (d, 1H, J=9.53 Hz), 5.426 (s, 1H), 5.051 (d, 1H, J=3.81 Hz), 4.220 (dd, 2H, J=13.70 Hz, J=22.45 Hz), 2.269 (s, 3H), 1.801 (s, 3H).

Example 55

1-(α-L-Lyxopyranosyl)-2,5,6-trichlorobenzimidazole

A 100 ml round bottom flask was charged with 1-(2,3,4-Tri-O-acetyl-α-L-lyxopyranosyl)-2,5,6-trichlorobenzimidazole (303 mg, 0.65 mmol) and this was dissolved in 50 ml of an equimolar mixture of ethanol and water. To the stirred solution was added anhydrous sodium carbonate (212 mg, 2.0 mmol) and the reaction mixture allowed to stir at room temperature for 3 hours. The solution was neutralized with acetic acid and the solvent evaporated in vacuo. the resultant solid was dissolved in ethyl acetate and this was washed successively with water, sat. $NaHCO_3$ solution, and sat. NaCl solution (1×50 ml each). The organic layer was dried over sodium sulfate and the solvent evaporated in vacuo to yield, upon vacuum drying, 205 mg (89.1%) of the title compound as a white foam. mp 184–184.5° C. $^1H$ NMR (DMSO-$d_6$, 360 at MHz) δ7.980 (s,1H), 7.922 (s, 1H), 5.644 (d,1H, J=9.26 Hz), 5.489 (d, 1H, J=3.24 Hz), 5.401 (d, 1H, J=3.76 Hz), 5.266 (d, 1H, J=6.52 Hz), 4.245 (m, 1H), 3.924 (d, 1H, J=2.81 Hz), 3.905 (dd, 2H, J=11.64 Hz, J=72.50 Hz). Anal. Calcd. for C, 40.76; H, 3.14; N, 7.92. Found: C, 40.78; H, 3.28; N, 7.75.

Example 56

2-Bromo-5,6-dichloro-1-(3'-deoxy-3'-C-hydroxymethyl-β-D-ribopyranosyl)-1H-benzimidazole a. 2,4-Di-O-Acetyl-1,6-anhydro-3-deoxy-3-C-hydroxymethyl-α-D-ribopyranose 3-Deoxy-3-C-hydroxymethyl-1,2-isopropylidene-α-D-ribofuranose (2.8g, 13.7 mmoles), which can be prepared by the method of Acton, Goerner, and etc., (J. Med. Chem. (1979), 22(5), 518–25) was dissolved in dioxane (75 ml) and 0.1 N HCl (75 ml) and heated in an 80° C. oil bath overnight. The pH of the reaction was very carefully adjusted to 5 with 0.1 N NaOH. Most of the water was removed by evaporation in vacuo. Ethanol was added and evaporated in vacuo (3×) to remove residual water. Toluene was added and evaporated (3×). The residue was dissolved in dry pyridine (50 ml, anhydrous, Aldrich Chemical Co.) and acetic anhydride (10.4 ml, 110 mmoles) was added. The reaction was stirred at RT overnight. Methanol was added and the solvents removed in vacuo. Toluene (50 ml) was added and removed in vacuo (5×) to remove residual pyridine, acetic anhydride, and acetic acid. The product was isolated by chromatography on a 4 by 15 cm column of silica gel eluted with hexane/ethyl acetate (7:3, v/v). MS (GC-Cl+): m/z, 350, $M+NH_4^+$. $^1H$ NMR (DMSO-$d_6$) δ5.2 (s,1H, H1), 4.9 (m,1H, H4), 4.75 (s,1H, H-2), 4.1(d, 1H, H-6), 3.85 (dd, 1H, H-6), 3.75 (dd, 1H, H-5), 3.2 (t, 1H, H-5), 2.8(m, 1H, H-3), 2.05 (s, 6H, acetyls).

b. 1,2,4-triacetyl-3-deoxy-3-C-hydroxymethyl-D-ribopyranose 2,4 Di-O-acetyl-1,6-anhydro-3-deoxy-3-C-hydroxymethyl-α-D-ribopyranose (0.5 g, 1.5 mmoles) was dissolved in acetic anhydride (7.5 ml) and acetic acid (19.5 ml). Concentrated sulfuric acid (1.3 ml) was added and the reaction was stirred at RT overnight. GC-MS indicated the formation of two major products in approximately a 1:1 ratio along with 2 minor products. Ice (50 g) was added to the reaction. The products were extracted with ether (2×). The organic solution was dried with magnesium sulfate, filtered, and the solvent removed in vacuo. Toluene was added to the residue and evaporated in vacuo (3×) to remove residual water. The desired product; 1,2,4-triacetyl-3-deoxy-3-C-hydroxymethyl-D-ribopyranose, was isolated as a mixture of anomers along with a second product by chromatography on 4 by 15 cm column of silica gel eluted with hexane/ethyl acetate (7:3, v/v). The mixture was used in the next step without further purification.

c. 2-Bromo-5,6-dichloro-1-(3'-deoxy-3'-C-hydroxymethyl-β-D-ribopyranosyl)-1H-benzimidazole 2-Bromo-5,6-dichloro-benzimidazole (0.36 g, 1.4 mmoles) which can be prepared by the method of Townsend and Drach (U.S. Pat. No. 5,248,672) was added to 1,2-dichloroethane (Aldrich, Sure Seal, 20 ml). N,O-Bis (trimethylsilyl)acetamide (0.19 ml, 0.76 mmoles, 1 eq.) was added and the reaction heated to reflux for thirty minutes in a 95° C. oil bath. 1,2,4-Triacetyl-3-deoxy-3-C-hydroxymethyl-D-ribopyranose (0.45 g, 1.4 mmoles, 1 eq.) was boiled in toluene to remove water. The excess toluene wag removed in vacuo and the residue dissolved in 1,2-dichloroethane (15 ml). The carbohydrate solution was added to the reaction followed by trimethylsilyl trifluoromethanesulfonate (0.365 ml, 1.7 mmoles, 1.2 eq.). The reaction was heated for 50 min in an 85° C. oil bath. The reaction was cooled to RT and ice water (100 ml) was added. The organic layer was collected and washed with saturated sodium bicarbonate and brine. The organic solution was dried with $MgSO_4$, filtered, and the solvent removed in vacuo. The product was purified by chromatography on a 4×15 cm column of silica gel eluted with chloroform/methanol (98:2, v/v). The product containing fractions were combined and the solvents removed in vacuo.

Isolation of the final product was accomplished by deprotection of the acetyl groups. The acetylated product was dissolved in 15 ml ethanol/water (1:1, v/v) $Na_2CO_3$ (1.2 g) was added and the reaction stirred at RT overnight. The reaction was neutralized by the addition of 1 N HCl then diluted with sat. NaCl (1 vol.). The product was extracted with ethyl acetate (2×). After removal of the solvent in vacuo, the product was isolated by chromatography on a 4 by 6 cm column of silica gel eluted with chloroform/methanol (95:5, v/v). MS (ES+): m/z, 411, M+H$^+$. 1-Br, 2-Cl pattern was noted. $^1$H NMR (DMSO-$d_6$) δ7.99 (s,1H, aryl), 7.96 (s,1H, aryl), 5.94 (d,1H, H-1', $J_{1',2'}$=9 Hz), 5.45(bs, 1H, OH), 5.25 (bs, 1H, OH), 4.45(bs, 1H, OH), 4.25 (m, 1H, H-2'), 4.1(m, 1H, H4') 4.0(m, 2H, H-6') 3.8 (m, 1H, H-5'), 3.7 (m, 1H, H-5'), 2.3 (m, 1H, H-3').

Example 57

2-Bromo-5,6-dichloro-1-beta-L-xylopyranosyl-1H-benzimidazole a. 1,2,3,4-tetra-O-acetyl-beta-L-xylopyranose L-xylose (11.48 g, 76.5 mmol) was combined with pyridine (Aldrich, 250 ml) and concentrated to a volume of 50 ml. The solution was cooled in an ice bath, and acetic anhydride (Aldrich, 30 ml, 321 mmol) was added dropwise over 30 min. After 4 h, the reaction was warmed to room temperature and stirred overnight. Ethanol (100 ml) was added and the reaction stirred 1 h. The reaction was concentrated to 50 ml, diluted with 200 ml ethanol and evaporated. The residue was partitioned between ethyl acetate and water. The ethyl acetate was washed successively with water, 7% aqueous sodium bicarbonate and saturated aqueous sodium chloride, then dried over anhydrous magnesium sulfate and evaporated. The residue was chilled and the resulting solid was recrystallized from isopropanol to yield 13.99 g (44.0 mmol, 57% yield) of 1,2,3,4-tetra-O-acetyl-beta-L-xylopyranose. $^1$H NMR (DMSO-$d_6$) δ5.79–5.77 (d, 1H), 5.28–5.24 (t, 1H), 4.89–4.82 (m, 2H), 3.98–3.94 (dd, 1H), 3.67–3.62 (dd, 1H), 2.03 (s, 3H), 1.98 (s, 3H), 1.97 (s, 3H), 1,96 (a, 3H).

b. 2-Bromo-5,6-dichloro-1-(2,3,4-tri-O-acetyl-beta-L-xylopyranosyl)-1H-benzimidazole As described in General Procedure III, 2-bromo-5,6-dichlorobenzimidazole (1.0 g, 3.8 mmol), N,O-bis (trimethylsilyl) acetamide (Aldrich, 1.0 ml, 4.1 mmol), and 1,2-dichloroethane (Aldrich Sure Seal, 25 ml) were combined and refluxed under nitrogen for 0.5 h. The solution was cooled to 50° C. and trimethylsilyl trifluoromethane-sulfonate (Aldrich, 0.8 ml, 4.1 mmol) was added. Immediately, 1.4 g (4.4 mmol) solid 1,2,3,4-tetra-O-acetyl-beta-L-xylopyranose was added. The solution was stirred under nitrogen at reflux for 0.25 h, then poured into 7% aqueous sodium bicarbonate and extracted with dichloromethane. The organic layers were dried with magnesium sulfate (anhyd), filtered, and evaporated. The crude residue was crystallized from chloroform and hexane to give 1.11 g (56% yield) of 2-bromo-5,6-dichloro-1-(2,3,4-tri-O-acetyl-beta-L-xylopyranosyl)-1H-benzimidazole. $^1$H NMR (CDCl$_3$) δ7.80 (s,1H), 7.76 (s, 1H), 5.68–5.64 (m, 1H), 5.55–5.51 (m, 1H), 5.32–5.25 (m, 1H), 4.48–4.43 (dd, 1H), 3.69–3.61 (t, 1H), 2.15 (s, 3H), 2.10 (s, 3H), 1.90 (s, 3H).

c. 2-Bromo-5,6-dichloro-1-beta-L-xylopyranosyl-1H-benzimidazole

An ethanolic solution of 2-bromo-5,6-dichloro-1-(2,3,4-tri-O-acetyl-alpha-L-xylopyranosyl)-1H-benzimidazole (0.81 g, 1.54 mmol) was deprotected in a modification of General Procedure VI with 0.64 g (6.03 mmol) of sodium carbonate in 5 ml of water. After stirring overnight at ambient temperature, the mixture was treated as described in General Procedure VI to give crude product which was recrystallized from 1-chlorobutane, ethyl acetate and hexane to give 0.21 g (0.53 mmol, 34% yield) of 2-bromo-5,6-dichloro-1-beta-L-xylopyranosyl-1H-benzimidazole, mp 164–165° C. $^1$H NMR (CD$_3$OD) δ8.04 (s,1H), 7.83 (s, 1H), 5.53–5.50 (d, 1H), 4.14–4.09 (dd, 1H), 3.93 (bm, 1H), 3.83–3.75 (m, 1H), 3.55–3.46 (m, 2H).

Example 58

5,6-Dichloro-N-1(1-methylethyl)-1-beta-L-xylopyranosyl-1H-benzimidazole-2-amine 2-bromo-5,6-dichloro-1-(2,3,4-tri-O-acetyl-beta-L-xylopyranosyl)-1H-benzimidazole (0.25 g, 0.48 mmol) was dissolved in 10 ml of absolute ethanol, treated with 5 ml of isopropylamine (Fluka, Ronkonkoma, N.Y.), heated in a glass pressure tube (Ace, Vineland, N.J.) and stirred with a magnetic stir bar. The tube was sealed with a screw cap and heated in an oil bath at 85° C. for 40 h. At this time, TLC indicated complete conversion of starting material and the solvents were removed on a rotary evaporator. The product residue was purified by filtration through a silica gel pad eluting with 10% methanol in chloroform to give 5,6-dichloro-N-1(1-methylethyl)-1-beta-L-xylopyranosyl-1H-benzimidazole-2-amine (0.15 g, 0.40 mmol, 83% yield). $^1$H NMR (CD,OD) δ 7.38 (s,1H), 7.31 (s, 1H), 5.34–5.31 (d, 1H), 4.10–4.02 (m, 2H), 3.90–3.84 (t, 1H), 3.77–3.69 (m, 1H), 3.51–3.42 (m, 2H), 1.30 (d, 3H), 1.28 (d, 3H).

Example 59

2-Bromo-5,6-dichloro-1-(3,4-di-O-acetyl-2-deoxy-alpha-D-erythro-pentopyranosyl)-1H-benzimidazole and 2-Bromo-5,6-dichloro-1-(3,4-di-O-acetyl-2-deoxy-beta-D-erythro-pentopyranosyl)-1H-benzimidazole

As described in General Procedure III, 2-bromo-5,6-dichlorobenzimidazole (0.52 g, 2.0 mmol), N,O-bis(trimethylsilyl) acetamide (Aldrich, 0.53 ml, 2.2 mmol), and 1,2-dichloroethane (Aldrich Sure Seal, 20 ml) were combined and refluxed under nitrogen for 0.25 h. The solution was cooled to 50° C. and trimethylsilyl trifluoromethanesulfonate (Aldrich, 0.42 ml, 2.2 mmol) was added. Immediately, 0.51 g (2.0 mmol) solid 1,3,4-tri-O-acetyl-2-deoxy-D-erythro-pentopyranose (as prepared and described by R. Allerton and W. G. Overend in *J. Chem. Soc.* 1951, 1480–1484) was added. The solution was stirred under nitrogen at 50° C. for 0.5 h, then poured into 7% aqueous sodium bicarbonate and extracted with dichloromethane. The organic layer was dried with magnesium sulfate (anhyd), filtered, and evaporated. The crude residue was purified on a silica gel column eluting with a step gradient of 0.1% to 1% methanol in dichloromethane to give 0.47 g (1.0 mmol, 52% yield) 2-bromo-5,6-dichloro-1-(3,4-di-O-acetyl-2-deoxy-alpha-D-erythro-pentopyranosyl)-1H-benzimidazole; $^1$H NMR (CD$_3$OD) $\delta$8.11 (s, 1H), 7.80 (s, 1H), 6.11–6.07 (dd, 1H), 5.37–5.32 (m, 2H), 4.24–4.19 (dd, 1H), 4.05–4.00 (dd, 1H), 2.68–2.56 (q, 1H), 2.32 (s, 3H), 2.20–2.15 (m, 1H), 2.01 (s, 3H); and 0.13 g (0.28 mmol, 14% yield) 2-bromo-5,6-dichloro-1-(3,4-di-O-acetyl-2-deoxy-beta-D-erythro-pentopyranosyly)-1H-benzimidazole; $^1$H NMR (CD$_3$OD) $\delta$8.02 (s, 1H), 7.76 (s, 1H), 6.13–6.10 (d, 1H), 5.62 (bs, 1H), 5.29–5.23 (m, 1H), 4.15–4.03 (m, 2H), 2.76–2.70 (t, 1H), 2.19 (s, 3H), 2.15–2.1 (m, 1H), 2.00 (s, 3H).

Example 60

2-Bromo-5,6-dichloro-1-(2-deoxy-alpha-D-erythro-pentopyranosyl)-1H-benzimidazole

An ethanolic solution of 2-bromo-5,6-dichloro-1-(3,4-di-O-acetyl-2-deoxy-alpha-D-erythro-pentopyranosyl)-1H-benzimidazole (0.21 g, 0.45 mmol) was deprotected in a modification of General Procedure VI with 0.12 g (1.17 mmol) of sodium carbonate in 1 ml of water. After stirring overnight at ambient temperature, the mixture was treated as described in General Procedure VI. The crude product was triturated in ethyl acetate to give 0.11 g (0.29 mmol, 65% yield) of 2-bromo-5,6-dichloro-1-(2-deoxy-alpha-D-erythro-pentopyranosyl)-1H-benzimidazole. $^1$H NMR (DMSO-d$_6$) $\delta$8.15 (s, 1H), 7.96 (s, 1H), 5.80–5.77 (d, 1H), 5.12 (bs, 1H), 4.97 (m, 1H), 3.97–3.90 (m, 2H), 3.78–3.70 (m, 2H), 2.42–2.35 (m, 1H), 1.83–1.79 (m, 1H).

Example 61

5,6-Dichloro-N-1(1-methylethyl)-1-(2-deoxy-alpha-D-erythro-pentopyranosyl)-1H-benzimidazole-2-amine

2-bromo-5,6dichloro-1-(3,4-di-O-acetyl-2-deoxy-alpha-D-erythro-pentopyranosyl)-1H-benzimidazole (0.098 g, 0.21 mmol) was dissolved in 4 ml of absolute ethanol, treated with 2 ml of isopropylamine (Fluka, Ronkonkoma, N.Y.), heated in a glass pressure tube (Ace, Vineland, N.J.) and stirred with a magnetic stir bar. The tube was sealed with a screw cap and heated in an oil bath at 85° C. for 24 h. At this time, TLC indicated complete conversion of starting material and the solvents were removed on a rotary evaporator. The residue was triturated in dichloromethane to give 0.062 g (0.17 mmol, 82% yield) 5,6-dichloro-N-1(1-methylethyl)-1-(2-deoxy-alpha-D-erythro-pentopyranosyl)-1H-benzimidazole-2-amine. $^1$H NMR (DMSO-d$_6$) $\delta$7.63 (s, 1H), 7.38 (s, 1H), 5.64–5.60 (d, 1H), 5.06 (bs, 1H), 4.93 (bs, 1H), 4.02–3.89 (m, 2H), 3.80–3.65 (m, 2H), 3.60–3.55 (d, 1H), 2.41–2.29 (q, 1H), 1.68–1.65 (d, 1H), 1.23 (s, 3H), 1.21 (s, 3H).

Example 62

2-Bromo-5,6-dichloro-1-(2-deoxy-beta-D-erythro-pentopyranosyl)-1H-benzimidazole

An ethanolic solution of 2-bromo-5,6-dichloro-1-(3,4-di-O-acetyl-2-deoxy-beta-D-erythro-pentopyranosyl)-1H-benzimidazole (0.13 g, 0.28 mmol) was deprotected in a modification of General Procedure VI with 0.077 g (0.73 mmol) of sodium carbonate in 1 ml of water. After stirring overnight at ambient temperature, the mixture was treated as described in General Procedure VI. The crude product was triturated in dichloromethane and hexane to give 0.06 g (0.16 mmol, 56% yield) of 2-bromo-5,6-dichloro-1-(2-deoxy-beta-D-erythro-pentopyranosyl)-1H-benzimidazole. $^1$H NMR (DMSO-d$_6$) $\delta$8.01 (s, 1H), 7.92 (s, 1H), 5.96–5.94 (d, 1H), 5.02 (s, 1H), 4.90–4.89 (d, 1H), 4.01 (s, 1H), 3.94–3.86 (m, 1H), 3.74–3.72 (d, 2H), 2.42–2.39 (m, 1H—partially underneath residual DMSO signal), 1.90–1.87 (d, 1H).

Example 63

2-Bromo-5-chloro-6-methylthio-1-beta-D-ribopyranosyl-1H-benzimidazole and 2-Bromo-6-chloro-5-methylthio-1-beta-D-ribopyranosyl-1H-benzimidazole a. 4-Chloro-2-nitro-5-methylthioaniline

Sodium methanethiolate (4.06 g, 58.0 mmol, Aldrich) was suspended in 80 ml dimethylformamide. 4,5-Dichloro-2-nitroaniline (10.0 g, 48.3 mmol, Aldrich) was added portionwise. Additional sodium methanethiolate (4.38 g, 62.5 mmol) was added over several h until starting material was consumed. The reaction mixture was poured into water (400 ml) and the resulting precipitate was collected by filtration and dried to give 9.05 g (41.4 mmol, 86% yield) of the title compound. $^1$H NMR (CDCl$_3$) $\delta$8.15 (s, 1H), 6.44 (s, 1H), 2.52 (s, 3H).

b. 3-Chloro-4-methylthio-1,2-phenylenediamine

A mixture of 9.05 g (41.4 mmol) 4-chloro-2-nitro-5-methylthioaniline and 28.82 g (165.6 mmol, Aldrich) sodium hydrosulfite was refluxed in 200 ml of ethanol and 80 ml of water for 1 h. The reaction mixture was evaporated, the residue was diluted with water and extracted with dichloromethane. The dichloromethane layers were washed with saturated aqueous sodium chloride, dried over anhydrous magnesium sulfate and filtered. The solvent was removed under reduced pressure to give 7.58 g (40.2 mmol, 97% yield) of the title compound. $^1$H NMR (CDCl3) $\delta$6.79 (s, 1H), 6.73 (s, 1H), 2.44 (s, 3H).

c. 5-Chloro-6-methylthiobenzimidazole

A solution of 3-chloro-4-methylthio-1,2-phenylenediamine (5.0 g, 26.5 mmol) in 75 ml ethanol was treated with triethylorthoformate (6.6 ml, 39.7 mmol, Aldrich) and trifluoroacetic acid (0.51 ml, 6.6 mmol, Aldrich). After stirring 0.25 h, the reaction mixture was concentrated under reduced pressure. The residue was crystallized from dichloromethane, ethyl acetate and hexane to give 2.19 g of the title compound in the first crop and 1.54 g in the second crop. The total yield was 3.73 g (18.8 mmol, 71% yield). $^1$H NMR (DMSO-d$_6$) δ8.49 (s, 1H), 7.80 (s, 1H), 7.52 (s, 1H), 2.56 (s, 3H).

d. 5-Chloro-6-methylthio-1-(2,3,4-tri-O-acetyl-beta-D-ribopyranosyl)-1H-benzimidazole and 6-Chloro-5methylthio-1-(2,3,4-tri-O-acetyl-beta-D-ribopyranosyl)-1H-benzimidazole As described in General Procedure III, 5-chloro-6-methylthiobenzimidazole (3.73 g, 18.8 mmol), N,O-bis(trimethylsilyl) acetamide (Aldrich, 4.9 ml, 20.7 mmol), and 1,2-dichloroethane (Aldrich Sure Seal, 100 ml) were combined and refluxed under nitrogen for 0.25 h. The solution was cooled to 40° C. and trimethylsilyl trifluoromethanesulfonate (Aldrich, 4.0 ml, 20.7 mmol) was added. Immediately, 7.17 g (22.5 mmol) solid 1,2,3,4-tetra-O-acetyl-beta-D-ribopyranose was added. The solution was stirred under nitrogen at reflux for 3 h, then poured into 7% aqueous sodium bicarbonate and extracted with dichloromethane. The organic layers were dried with magnesium sulfate (anhyd), filtered, and evaporated. The residue was purified by two successive silica gel columns eluting with dichloromethane and a step gradient from 0 to 50% acetone to give 0.36 g (0.8 mmol, 4% yield) of the title compounds as a regioisomeric mix (~1.7:1). $^1$H NMR (DMSO-d$_6$) δ8.46 (s, 1.6H), 8.22 (s, 1H), 7.82 (s, 0.6H), 7.72 (s, 0.6H), 7.58 (s, 1H), 6.12–6.03 (m, 1 .6H), 5.79–7.76 (m, 3.2H), 4.06–4.00 (m, 3.2H), 2.63 (s, 3H), 2.27–2.26 (d, 7.8H), 1.76 (s, 6.6H).

e. 2-Bromo-5-chloro-6-methylthio-1-(2,3,4-ti-O-acetyl-beta-D-ribopyranosyl)-1H-benzimidazole and 2-Bromo-6-chloro-5-methylthio-1-(2,3,4-tri-O-acetyl-beta-D-ribopyranosyl)-1H-benzimidazole The title compound was prepared according to General Procedure IV using 5-chloro-6-methylthio-1-(2,3,4-tri-O-acetyl-beta-D-ribopyranosyl)-1H-benzimidazole and 6-chloro-5-methylthio-1-(2,3,4-tri-O-acetyl-beta-D-ribopyranosyl)-1H-benzimidazole as a mixture of regioisomers (0.36 g, 0.79 mmol), 30 ml tetrahydrofuran (Aldrich Sure Seal, Milwaukee), and a total of 1.68 g (9.4 mmol) of N-bromosuccinimide that was added over 2 h. The product from work-up by General Procedure IV was purified on a silica gel column with dichloromethane and a step gradient from 0–0.5% methanol. This provided 0.18 g (0.34 mmol) of the title compounds as a mix of regioisomers. The regioisomers were separated by SFC on a semi-preparative Chiralcel OD lot No. S017OD00CJ-HC001 eluting with a mobile phase of 90% carbon dioxide and 10% methanol at a flow rate of 2.0 ml/min and a pressure of 3000 psi at a temperature of 40° C. with signal detection at 254 nm. 2-Bromo-5-chloro-6-methylthio-1-(2,3,4-tri-O-acetyl-beta-D-ribopyranosyl)-1H-benzimidazole eluted first (RT=5.78 min) and 0.047 g was obtained after evaporation of the solvent. $^1$H NMR (DMSO-d$_6$) δ7.79 (s, 1H), 7.68 (s, 1H), 6.03–6.00 (d, 1H), 5.78–5.74 (m, 2H), 5.57 (m, 1H), 4.23–4.17 (m, 1H), 4.09–4.01 (t, 1H), 2.64 (s, 3H), 2.26 (s, 3H), 2.04 (s, 3H), 1.80 (s, 3H). 2-Bromo-6-chloro-5-methylthio-1-(2,3,4-tri-O-acetyl-beta-D-ribopyranosyl)-1H-benzimidazole eluted from the chiral column last (RT=7.22 min) and 0.057 g was obtained after evaporation of the solvent. $^1$H NMR (DMSO-d$_6$) δ8.27 (s, 1H), 7.51 (s, 1H), 5.98–5.95 (d, 1H), 5.78–5.72 (m, 3H), 4.17–4.16 (m, 1H) 4.06–3.98 (t, 1H), 2.26 (3, 3H), 2.04 (s, 3H), 1.79 (s, 3H).

f. 2-Bromo-5-chloro-6-methylthio-1-beta-D-ribopyranosyl-1H-benzimidazole

An ethanolic solution of 2-bromo-5-chloro-6-methylthio-1-(2,3,4-tri-O-acetyl-beta-D-ribopyranosyl)-1H-benzimidazole (0.047 g, 0.09 mmol) was deprotected in a modification of General Procedure VI with 0.036 g (0.34 mmol) of sodium carbonate in 0.5 ml of water. After stirring 1 h at ambient temperature, the mixture was treated as described in General Procedure VI. The product was dried overnight in vacuo to give 2-bromo-5-chloro-6-methylthio-1-beta-D-ribopyranosyl-1H-benzimidazole (0.035 g, 0.09 mmol, 98% yield). $^1$H NMR (DMSO-d$_6$) δ7.73 (s, 1H), 7.37 (s, 1H), 5.63–5.60 (d, 1H), 5.16–5.14 (m, 2H), 4.91–4.89 (d, 1H), 4.00–3.99 (m, 2H), 3.86 (m, 1H), 3.71–3.68 (m, 2H), 2.52 (s, 3H).

g. 2-Bromo-6-chloro-5-methylthio-1-beta-D-ribopyranosyl-1H-benzimidazole

An ethanolic solution of 2-bromo-6-chloro-5-methylthio-1-(2,3,4-tri-O-acetyl-beta-D-ribopyranosyl)-1H-benzimidazole (0.057 g, 0.09 mmol) was deprotected in a modification of General Procedure VI with 0.044 g (0.41 mmol) of sodium carbonate in 0.5 ml of water. After stirring 1.5 h at ambient temperature, the mixture was treated as described in General Procedure VI. The product was dried overnight in vacuo to give 2-bromo-6-chloro-5-methylthio-1-beta-D-ribopyranosyl-1H-benzimidazole (0.042 g, 0.08 mmol, 98% yield). $^1$H NMR (DMSO-d$_6$) δ7.79 (s, 1H), 7.49 (s, 1H), 5.61–5.59 (d, 1H), 5.16–5.12 (m, 2H), 4.86–4.84 (d, 1H), 3.98 (m, 3H), 3.68–3.65 (m, 2H), 2.49 (s, 3H).

Examples 64–68

Scheme 1

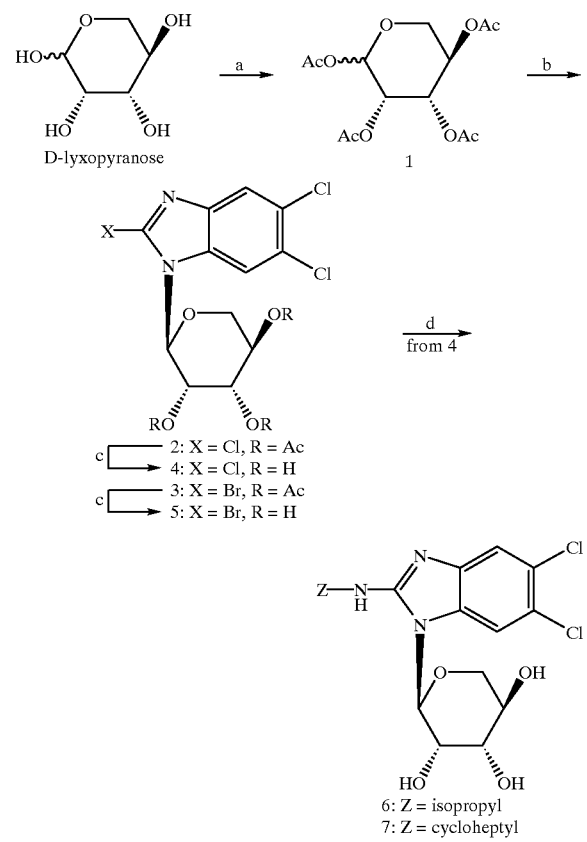

a) Ac$_2$O, pyr. b) 2 or 3, BSA, TMSOTf, CH$_3$CN. c) Na$_2$CO$_3$, EtOH/H$_2$O. d) ZNH$_2$, EtOH, 60 ÞC.

General Chemical Procedures: Melting points were determined on a Thomas-Hoover apparatus and are uncorrected. Silica gel, SilicAR 40–63 microns 230–400 mesh (Mallinckrodt) was used for column chromatography. Thin layer chromatography (TLC) was performed on prescored SilicAR 7GF plates (Analtech, Newark, Del.). TLC plates were developed in the following solvent systems: system 1 (35% EtOAc/Hexanes, v/v), system 2 (50% EtOAc/Hexanes, v/v), system 3 (10% MeOH/CH$_2$Cl$_2$, v/v), system 4 (15% MeOH/CH$_2$Cl$_2$, v/v). Compounds were visualized by illuminating with UV light (254 nm) or/and by treatment with 10% methanolic sulfuric acid followed by charring on a hot plate. Evaporations were carried out under reduced pressure (water aspirator) with the bath temperature not exceeding 50 ûC., unless specified otherwise. NMR spectra were recorded on either a Brōker 300 or 500 MHz instrument. Chemical shifts are expressed in d values (ppm) relative to the chemical shift of the residual DMSO-d$_5$ (d 2.50 ppm) contained in the solvent DMSO-d6. All NMR assignments reported were made by homonuclear decoupling experiments. Unless otherwise noted, all materials were obtained from commercial suppliers.

Example 64

1,2,3,4-Tetra-O-acetyl-D-lyxopyranose (1)

Acetic anhydride (23 mL, 240 mmol) was added to a stirred solution of D-lyxose (4.5 g, 30 mmol) in pyridine (90 mL) at room temperature. After 15 h, the reaction mixture was poured into ice water (200 mL) and extracted with dichloromethane (1×300 mL). The organic extract was washed with water (1×50 mL), dried over Na$_2$SO$_4$, filtered and the filtrate was concentrated under reduced pressure. After several coevaporations with toluene (3×10 mL), the residue was subjected to silica gel chromatography (5×15 cm) using a solution of ethyl acetate and hexane (1:1, v/v). Fraction 7 contained 1.6 g (17%) of the pure a anomer of 1 [R$_f$ (system 1): 0.40] which crystallized upon drying, and fractions 8–40 contained 6.8 g (71%) of a mixture of anomers of 1 [R$_f$ (system 1): 0.40 (major) and 0.35 (minor)] which also crystallized upon drying. Characteristics of the pure a anomer:

mp: 96–98 ûC.; $^1$H NMR (DMSO-d$_6$): d 5.89 (d, 1H, J=3.1 Hz, H-1), 5.20 (dd, 1H, J=9.1 and 3.4 Hz, H-3), 5.12 (t, 1H, J=3.3 Hz, H-2), 5.1–5.0 (m, 1H, H-4), 3.92 (dd, 1H, J=11.6 and 4.9 Hz, H-5), 3.7–3.6 (m, 1H, H-5'). Anal. (C$_{13}$H$_{18}$O$_9$) C,H.

Caracteristics of the mixture of anomers: mp: 87–89 ûC.

Example 65

2,5,6-Trichloro-1-(a-D-lyxopyranosyl)benzimidazole (4)

2,5,6-Trichlorobenzimidazole (3.0 g, 13.6 mmol) was suspended in acetonitrile (250 mL) and the mixture was stirred at 55 ûC. BSA (4.9 mL, 20 mmol) was added, and the reaction mixture stirred for an additional 15 min. Compound 1 (4.8 g, 15 mmol) in acetonitrile (20 mL) and TMSOTf (3.8 mL, 20 mmol) were added to the clear solution, and the mixture was stirred at 55 ûC. for an additional 18 h. A saturated aqueous solution of NaHCO$_3$ (10 mL) was added and the mixture was diluted with ethyl acetate (100 mL). The organic extract was washed with water (3×10 mL), dried over anhydrous sodium sulfate, filtered and concentrated under reduced pressure. The residue was subjected to silica gel chromatography [5×15 cm, eluent:gradient of methanol (0–1%) in dichloromethane]. The compound (4.9 g), isolated from fractions 9–48 [R$_f$ (system 1): 0.16], was dissolved in a solution of ethanol and water (9:1, v/v, 150 mL) and sodium carbonate (6.5 g, 61 mmol) was then added. The reaction mixture was stirred for 18 h, then acetic acid (3 mL) was added and the mixture was evaporated to dryness. Water (20 mL) and ethyl acetate (100 mL) were added to the residue. The organic extract was washed with water (2×10 mL), dried over Na$_2$SO$_4$, filtered and evaporated to dryness. The residue was suspended in boiling dichloromethane (50 mL) and methanol was added until complete dissolution. Compound 4 crystallized from this solution (2.47 g, 44%).

R$_f$ (system 3): 0.24; mp: 170–172 ûC. (decomp.); $^1$H NMR (DMSO-d$_6$): d 8.00 and 7.97 (2 s, 2H, H-4 and H-7), 5.64 (d, 1H, J=9.2 Hz, H-1'), 5.50 (d, 1H, J=2.9 Hz, D$_2$O exchangeable), 5.41 (d, 1H, J=3.6 Hz, D$_2$O exchangeable), 5.28 (d, 1H, J=6.4 Hz, OH-2'), 4.2 (m, 1H, H-2'), 4.02 (d, 1H, J=11.9 Hz), 3.92 (m, 1H), 3.8–3.6 (m, 2H, H-5' and H-5"); Anal. (C$_{12}$H$_{11}$Cl$_3$N$_2$O$_4$.1/4 H$_2$O) C,H,N.

Example 66

2-Bromo-5,6-dichloro-1-(a-D-lyxopyranosyl) benzimidazole (5)

2-Bromo-5,6-dichlorobenzimidazole (1.06 g, 4.0 mmol) was suspended in acetonitrile (70 mL) and the mixture was stirred at 35 ûC. BSA (1.46 mL, 6.0 mmol) was added, and the reaction mixture stirred for an additional 5 min. Compound 1 (1.52 g, 4.8 mmol) in acetonitrile (10 mL) and TMSOTf (1.15 mL, 1.5 mmol) were added to the clear solution, and the mixture was stirred at 35 ûC. for an additional 17 h. A saturated aqueous solution of NaHCO$_3$ (5 mL) was added and the mixture was diluted with ethyl acetate (20 mL). The organic extract was washed with water (3×5 mL), dried over anhydrous sodium sulfate, filtered and concentrated under reduced pressure. The residue was chromatographed on a silica gel column [3×15 cm, eluent:gradient of methanol (0–1%) in chloroform]. The compound (1.15 g), isolated from fractions 8–21 [R$_f$ (system 1): 0.18], was dissolved in a solution of ethanol and water (9:1, v/v, 46 mL) and sodium carbonate (1.5 g, 14 mmol) was added. The reaction mixture was stirred 17 h, then acetic acid (1 mL) was added and the mixture was evaporated to dryness. Water (30 mL) was added to the residue and the resulting precipitate was washed (2×10 mL) with more water, then suspended in boiling dichloromethane. Methanol was added until complete dissolution of the solid. 5 crystallized from this solution 220 mg, 26%), and also from the aqueous layer (150 mg, 18%). Both batches had same NMR. Characteristics of 5 crystallized in water.

R$_f$ (system 3): 0.25; mp: 169–171 ûC. (decomp.); $^1$H NMR (DMSO-d$_6$): d 7.99 and 7.95 (2 s, 2H, H-4 and H-7), 5.63 (d, 1H, J=9.1 Hz, H-1'), 5.49 (bs, 1H, D$_2$O exchangeable), 5.41 (bs, 1H, D$_2$O exchangeable), 5.22 (d, 1H, J=6.2 Hz, OH-2'), 4.24 (m, 1H, H-2'), 4.0–3.8 (m, 2H, H-3' and H-4'), 3.8–3.6 (m, 2H, H-5' and H-5"); Anal. (C$_{12}$H$_{11}$BrCl$_2$N$_2$O$_4$.H$_2$O) C,H,N.

Example 67

5,6-Dichloro-2-isopropylamino-1-(a-D-lyxopyranosyl)benzimidazole (6)

Compound 4 (300 mg, 0.85 mmol) was dissolved in ethanol (6 mL). Isopropylamine (5.5 mL, 65 mmol) was added to the solution, the flask was sealed and the reaction mixture stirred at 60 ûC. for 2 days. The mixture was decanted and evaporated to dryness. The residue from the evaporation was dissolved in ethyl acetate (50 mL) and then washed with water (3×5 mL). The organic extract was dried over sodium sulfate, filtered and the filtrate was evaporated under reduced pressure. The residue was subjected to silica gel chromatography [2×15 cm, eluent:gradient of methanol (5–8%) in dichloromethane]. Fractions that contained the major spot [R$_f$ (system 3): 0.24] were evaporated and the resulting solid was suspended in boiling chloroform. Methanol was added until complete dissolution of the solid. Compound 6 crystallized from this solution (260 mg, 81%). All attempts to obtain 6 free of chloroform failed.

R$_f$ (system 3): 0.24; mp: 214–218 ûC. (decomp.); $^1$H NMR (DMSO-d$_6$): d 7.55 and 7.36 (2 s, 2H, H-4and H-7), 6.47 (d, 1H, NH, J=6.8 Hz), 5.5–5.3 (m, 3H, H-1', OH-4' and OH-3'), 4.94 (d, 1H, J=7.9 Hz, OH-2'), 4.2 (m, 1H, H-2'), 4.1–3.9 (m, 3H, H-3', H-4' and CH(CH3)3), 3.7 (m, 2H, H-5',5"), 1.21 (d, 6H, CH(C$\underline{H}$$_3$)$_3$, J=6.4 Hz): Anal. (C$_{15}$H$_{19}$Cl$_2$N$_3$O$_4$·1/10 CHCl$_3$) C,H,N.

Example 68

2-Cycloheptylamino-5,6-dichloro-1-(a-D-lyxopyranosyl)benzimidazole (7)

Compound 4 (200 mg, 0.57 mmol) was dissolved in ethanol (4 mL). Cycloheptylamine (3.9 mL, 28 mmol) was added, the flask was sealed and the reaction mixture stirred at 60 ûC. for 2 days. The mixture was decanted and evaporated to dryness at 65 ûC. under high vacuum. The residue was dissolved in ethyl acetate (20 mL), and crystals of cycloheptylammonium chloride were removed by filtration. The organic extract was dried over sodium sulfate, filtered and the filtrate was evaporated under reduced pressure. The residue was subjected to silica gel chromatography [2×15 cm, eluent:gradient of methanol (0–6%) in dichloromethane]. Fractions that contained the major spot [R$_f$(system 3): 0.30] were evaporated and the resulting solid was suspended in boiling dichloromethane. Methanol was added until complete dissolution of the solid. Compound 7 crystallized from this solution (150 mg, 61%).

R$_f$ (system 3): 0.30; mp: 160–165 ûC. (decomp.); $^1$H NMR (DMSO-d$_6$): d 7.52 and 7.36 (2 s, 2H, H-4 and H-7), 6.43 (d, 1H, NH, J=7.0 Hz), 5.5–5.3 (m, 3H, H-1', OH-4' and OH-3'), 4.95 (d, 1H, J=8.0 Hz, OH-2'), 4.2 (m, 1H, H-2'), 4.0–3.9 (m, 3H, H-3', H4' and C$\underline{H}$(CH$_2$)$_n$), 3.7 (m, 2H, H-5',5"), 2.0–1.9 (bs, 2H, cycloheptyl), 1.7–1.4 (m, 10H, cycloheptyl); Anal. (C$_{19}$H$_{25}$Cl$_2$N$_3$O$_4$) C,H,N.

Example 69

Human Cytomegalovirus Assay

HCMV strain AD169 was grown on monolayers of human embryonic lung cells (MRC5 cells) in 96 well plates. After infection of the cells at a ratio of approximately 0.01 infectious virus particles per cell, the compounds to be tested were added to selected wells at six different concentrations, each in triplicate. The same concentrations of compound were also applied to wells containing monolayers of uninfected cells in order to assess compound cytotoxicity. The plates were incubated for 5 days, and the minimum cytotoxic dose was estimated from microscopic examination. The IC50 for antiviral effect was estimated from measurements of HCMV DNA in each well by blotting and quantitative specific DNA hybridization, similar to the method of Gadler (Antimicrob. Agents Chemother. 1983, 24, 370–374).

| Example | HCMV IC50 |
|---|---|
| 1 | 1.0 µM |
| 2 | 0.7 µM |
| 3 | 22 µM |
| 13 | 6 µM |
| 24 | 0.9 µM |

Example 70

Hepatitis B Virus Assay

The activity of compounds against Hepatitis B Virus was assessed as described in Jansen, R. et al., *Antimicrobial Agents and Chemotherapy*, Vol. 37, No. 3, pp. 441–447, 1993. Representative IC$_{50}$ values for the compounds according to the invention were in the range of 0.001–10 µM.

Example 71

Tablet Formulation

The following formulations A, B and C are prepared by wet granulation of the ingredients with a solution of povidone, followed by addition of magnesium stearate and compression.

|  | mg/tablet |
|---|---|
| Formulation A | |
| Active Ingredient | 250 |
| Lactose B.P. | 210 |
| Povidone B.P. | 15 |
| Sodium Starch Glycollate | 20 |
| Magnesium Stearate | 5 |
|  | 500 |
| Formulation B | |
| Active Ingredient | 250 |
| Lactose B.P. | 150 |
| Avicel PH 101 | 60 |
| Povidone B.P. | 15 |
| Sodium Starch Glycollate | 20 |
| Magnesium Stearate | 5 |
|  | 500 |
| Formulation C | |
| Active Ingredient | 250 |
| Lactose B.P. | 200 |
| Starch | 50 |
| Povidone | 5 |
| Magnesium Stearate | 4 |
|  | 359 |

The following formulations, D and E, are prepared by direct compression of the admixed ingredients. The lactose in formulation E is of the direct compression type (Dairy Crest-"Zeparox").

| | mg/tablet |
|---|---|
| Formulation D | |
| Active Ingredient | 250 |
| Pregelatinized Starch NF15 | 150 |
| | 400 |
| Formulation E | |
| Active Ingredient | 250 |
| Lactose B.P. | 150 |
| Avicel | 100 |
| | 500 |

Formulation F (Controlled Release Formulation)

The formulation is prepared by wet granulation of the ingredients with a solution of povidone followed by the addition of magnesium stearate and compression.

| | mg/tablet |
|---|---|
| Active Ingredient | 500 |
| Hydroxypropylmethylcellulose (Methocel K4M Premium) | 112 |
| Lactose B.P. | 53 |
| Povidone B.P. | 28 |
| Magnesium Stearate | 7 |
| | 700 |

Drug release takes place over a period of about 6–8 hours and is complete after 12 hours.

Example 72

Capsule Formulations

Formulation A

A capsule formulation is prepared by admixing the ingredients of formulation D in Example 1 above and filling into a two-part hard gelatin capsule. Formulation B (infra) is prepared in a similar manner.

| | mg/capsule |
|---|---|
| Formulation B | |
| Active Ingredient | 250 |
| Lactose B.P. | 143 |
| Sodium Starch Glycollate | 25 |
| Magnesium Stearate | 2 |
| | 420 |
| Formulation C | |
| Active Ingredient | 250 |
| Macrogel 4000 B.P. | 350 |
| | 600 |

Capsules of formulation C are prepared by melting the Macrogel 4000 B.P., dispersing the active ingredient in the melt and filling the melt into a two-part hard gelatin capsule.

| Formulation D | mg/capsule |
|---|---|
| Active Ingredient | 250 |
| Lecithin | 100 |
| Arachis Oil | 100 |
| | 450 |

Capsules of formulation D are prepared by dispersing the active ingredient in the lecithin and arachis oil and filling the dispersion into soft, elastic gelatin capsules.

| Formulation E | mg/capsule |
|---|---|
| Active Ingredient | 150.0 |
| Vitamin E TPGS | 400.0 |
| Polyethylene Glycol 400 NF | 200.5 |
| Propylene Glycol USP | 39.5 |

Four (4) kilograms (kg) of Vitamin E TPGS (obtained from Eastman Chemical Co.) was heated at 50° C. until liquefied. To the liquified Vitamin E TPGS, 2.005 kg of polyethylene glycol 400 (PEG400) (low aldehyde, <10 ppm, obtained from Union Carbide or Dow Chemical Co.) heated to 50° C. was added and mixed until a homogeneous solution was formed. The resultant solution was heated to 65° C. 1.5 kg of active ingredient was dissolved in the liquefied solution of Vitamin E TPGS and PEG 400. 0.395 kg of propylene glycol at room temperature was added and mixed until a homogenous solution was formed. The solution was cooled to 28–35° C. The solution was then de-gassed. The mixture was preferably encapsulated at 28–35° C. at a fill weight equivalent to 150 mg of volatiles-free compound, into Size 12 oblong, white opaque soft gelatin capsules using a capsule filling machine. The capsule shells were dried to a constant fill moisture of 3–6% water and a shell hardness of 7–10 Newtons, and placed in a suitable container.

Formulation F (Controlled Release Capsule)

The following controlled release capsule formulation is prepared by extruding ingredients a, b, and c using an extruder, followed by spheronization of the extrudate and drying. The dried pellets are then coated with release-controlling membrane (d) and filled into a two-piece, hard gelatin capsule.

| | mg/capsule |
|---|---|
| (a) Active Ingredient | 250 |
| (b) Microcrystalline Cellulose | 125 |
| (c) Lactose B.P. | 125 |
| (d) Ethyl Cellulose | 13 |
| | 513 |

Example 73

Injectable Formulation

| Formulation A | mg |
|---|---|
| Active ingredient | 200 |
| Hydrochloric Acid Solution 0.1M or Sodium Hydroxide Solution 0.1M q.s. to pH | 4.0 to 7.0 |
| Sterile water q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with water and filtered through a sterile micropore filter into a sterile 10 ml amber glass vial (type 1) and sealed with sterile closures and overseals.

| Formulation B | |
|---|---|
| Active ingredient | 125 mg |
| Sterile, Pyrogen-free, pH 7 Phosphate Buffer, q.s. to | 25 ml |
| Formulation C: intramuscular injection | |
| Active Ingredient | 200 mg |
| Benzyl Alcohol | 0.10 g |
| Glycofurol 75 | 1.45 g |
| Water for injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

Example 74

Syrup

| Active ingredient | 250 mg |
|---|---|
| Sorbitol Solution | 1.50 g |
| Glycerol | 2.00 g |
| Sodium Benzoate | 0.005 g |
| Flavor, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbital solution and finally the flavor. The volume is made up with purified water and mixed well.

Example 75

Suppository

| | mg/capsule suppository |
|---|---|
| Active ingredient | 250 |
| Hard Fat, B.P. (Witepsol H15-Dynamit Nobel) | 1770 |
| | 2020 |

One-fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 45° C. At a temperature of 38° C. to 40° C., 2.02 g of the mixture is filled into suitable, 2 ml plastic molds. The suppositories are allowed to cool to room temperature.

Example 76

Pessaries

| | mg/pessary |
|---|---|
| Active Ingredient | 250 |
| Anhydrate Dextrose | 380 |
| Potato Starch | 363 |
| Magnesium Stearate | 7 |
| | 1000 |

The above ingredients are mixed directly.

What is claimed is:

1. A compound of formula (I)

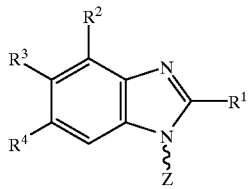

(I)

wherein:

$R^1$ is halogen, hydroxy, azido, $C_{1-8}$alkyl, $C_{1-8}$alkoxy, $C_{2-6}$alkenyl, $C_{2-6}$alkynyl, $C_{6-14}$aryl$C_{2-6}$alkenyl, $C_{6-14}$aryl$C_{2-6}$alkynyl, $-NR^{19}R^{20}$ where $R^{19}$ and $R^{20}$ may be the same or different and are hydrogen, $C_{1-8}$alkyl, cyano$C_{1-8}$alkyl, hydroxy$C_{1-8}$alkyl, halo$C_{1-8}$alkyl, $C_{3-7}$cycloalkyl, $C_{1-8}$alkyl$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-6}$alkyl, heterocycle$C_{1-8}$alkyl, $C_{1-8}$alkylcarbonyl, $C_{6-14}$arylsulfonyl, or $R^{19}R^{20}$ together with the N atom to which they are attached form a 3, 4, 5 or 6 membered heterocyclic ring; $OR^{21}$ where $R^{21}$ is hydrogen, $C_{1-8}$ alkyl, $C_{3-7}$cycloalkyl, or $C_{6-14}$aryl; or $SR^{22}$ where $R^{22}$ is hydrogen, $C_{1-8}$alkyl, hydroxy$C_{1-8}$alkyl, $C_{3-7}$cycloalkyl, or $C_{6-14}$aryl;

$R^2$ is hydrogen or halogen;

$R^3$ and $R^4$ may be the same or different and are hydrogen, halogen, $C_{1-8}$alkyl, $C_{6-14}$aryl, heterocycle $C_{6-14}$aryl, $C_{1-8}$alkoxy, halo$C_{1-8}$alkyl or —$SR^{24}$ where $R^{24}$ is hydrogen, $C_{1-8}$alkyl, $C_{6-14}$aryl, or $C_{6-14}$aryl$C_{1-8}$alkyl;

Z is a substituent of formula (Ia) or (Ib)

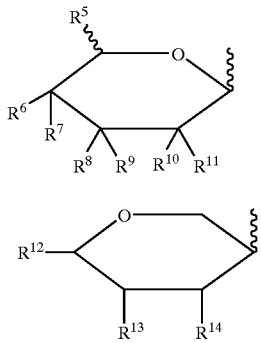

(Ia)

(Ib)

wherein:

$R^5$ is hydrogen, $C_{1-8}$alkyl, halo$C_{1-8}$alkyl or $C_{1-8}$alkoxy;

$R^6$ is hydrogen, hydroxy, halogen, $C_{1-8}$alkyl, hydroxy$C_{1-8}$alkyl, halo$C_{1-8}$alkyl or $C_{1-8}$alkoxy;

$R^7$ is hydrogen, hydroxy, halogen, $C_{1-8}$alkyl, hydroxy$C_{1-8}$alkyl, halo$C_{1-8}$alkyl, $C_{1-8}$alkoxy, or $R^6$ and $R^7$ together form a ketone or alkene;

$R^8$–$R^{11}$ are the same or different and are hydrogen, hydroxy, halogen, $C_{2-8}$alkyl, hydroxy$C_{1-8}$alkyl, halo$C_{1-8}$alkyl, $C_{1-8}$alkoxy, or any of $R^8$ and $R^9$ or $R^{10}$ and $R^{11}$ together form a ketone or alkene;

$R^{12}$–$R^{14}$ are the same or different and are hydrogen, hydroxy, $C_{1-8}$ alkyl or hydroxy$C_{1-8}$alkyl;

or a pharmaceutically acceptable derivative thereof, provided that a compound of formula (I) is not 2,5-dimethyl-1-(2,3,4-tri-O-acetyl-beta-D-xylopyranosyl)-1H-benzimidazole or 5,6-dimethyl-1-(2,3,4-tri-O-acetyl-beta-D-arabinopyranosyl)-benzimidazole-2-thione;

further provided that when Z is a substituent of formula (Ia):

a) $R^2$, $R^3$, and $R^4$ are not all hydrogen; and b) $R^1$ is not $NR^{19}R^{20}$ where $R^{19}$ and $R^{20}$ together with the N atom to which they are attached form a 5 membered heterocyclic ring containing S; and further provided that when Z is a substituent of formula (Ib):

a) $R^1$ is not $NR^{19}R^{20}$ where $R^{19}$ and $R^{20}$ together with the N atom to which they are attached form a 5 membered heterocyclic ring containing S.

2. A compound of formula (II)

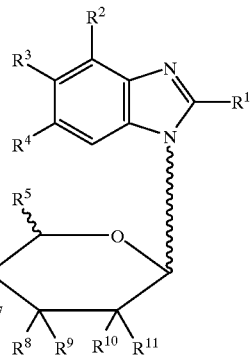

(II)

wherein:

$R^1$ is halogen, hydroxy, azido, $C_{1-8}$alkyl, $C_{1-8}$alkoxy, $C_{2-6}$alkenyl, $C_{2-6}$alkynyl, $C_{6-14}$aryl$C_{2-6}$alkenyl, $C_{6-14}$aryl$C_{2-6}$alkynyl, —$NR^{19}R^{20}$ where $R^{19}$ and $R^{20}$ may be the same or different and are hydrogen, $C_{1-8}$alkyl, cyano$C_{1-8}$alkyl, hydroxy$C_{1-8}$alkyl, halo$C_{1-8}$alkyl, $C_{3-7}$cycloalkyl, $C_{1-8}$alkyl$C_{3-7}$cycloalkyl, $C_{2-6}$alkenyl, $C_{3-7}$cycloalkyl $C_{1-8}$alkyl, $C_{2-6}$alkynyl, $C_{6-14}$aryl, $C_{6-14}$aryl$C_{1-6}$alkyl, heterocycle$C_{1-8}$alkyl, $C_{1-8}$alkylcarbonyl, $C_{6-14}$arylsulfonyl, or $R^{19}R^{20}$ together with the N atom to which they are attached form a 3, 4, 5 or 6 membered heterocyclic ring, $OR^{21}$ where $R^{21}$ is hydrogen, $C_{1-8}$alkyl, $C_{3-7}$cycloalkyl, or $C_{6-14}$aryl, or $SR^{22}$ where $R^{22}$ is hydrogen, $C_{1-8}$alkyl, hydroxy$C_{1-8}$alkyl, $C_{3-7}$cycloalkyl, or $C_{6-14}$aryl;

$R^2$ is hydrogen or halogen;

$R^3$ and $R^4$ are the same or different and are hydrogen, halogen, $C_{1-8}$alkyl, $C_{6-14}$aryl, heterocycle$C_{6-14}$aryl, $C_{1-8}$alkoxy, halo$C_{1-8}$alkyl or —$SR^{24}$ where $R^{24}$ is hydrogen, $C_{1-8}$alkyl, $C_{6-14}$aryl, or $C_{6-14}$aryl$C_{1-8}$alkyl;

$R^5$ is hydrogen, $C_{1-8}$alkyl, halo$C_{1-8}$alkyl, or $C_{1-8}$alkoxy;

$R^6$ is hydrogen, hydroxy, halogen, $C_{1-8}$alkyl, hydroxy$C_{1-8}$alkyl, halo$C_{1-8}$alkyl, or $C_{1-8}$alkoxy;

$R^7$ is hydrogen, hydroxy, halogen, $C_{1-8}$alkyl, hydroxy$C_{1-8}$alkyl, halo$C_{1-8}$alkyl, $C_{1-8}$alkoxy, or $R^6$ and $R^7$ together form a ketone or alkene;

$R^8$–$R^{11}$ are the same or different and are hydrogen, hydroxy, halogen, $C_{2-8}$alkyl, hydroxy$C_{1-8}$alkyl, halo$C_{1-8}$alkyl, $C_{1-8}$alkoxy, or any of $R^8$ and $R^9$ or $R^{10}$ and $R^{11}$ together form a ketone or alkene;

or a pharmaceutically acceptable derivative thereof, provided that a compound of formula (II) is not 2,5-dimethyl-1-(2,3,4-tri-O-acetyl-beta-D-xylopyranosyl)-1H-benzimidazole or 5,6-dimethyl-1-(2,3,4-tri-O-acetyl-beta-D-arabinopyranosyl)-benzimidazole-2-thione;

further provided that:

a) $R^2$, $R^3$, and $R^4$ are not all hydrogen; and b) $R^1$ is not $NR^{19}R^{20}$ where $R^{19}$ and $R^{20}$ together with the N atom to which they are attached form a 5 membered heterocyclic ring containing S.

3. A compound of formula (III)

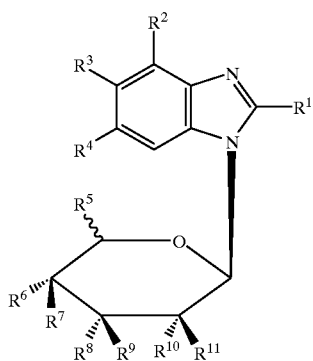

(III)

wherein;

R$^1$ is halogen, hydroxy, azido, C$_{1-8}$alkyl, C$_{1-8}$alkoxy, C$_{2-6}$alkenyl, C$_{2-6}$alkynyl, C$_{6-14}$arylC$_{2-6}$alkenyl, C$_{6-14}$arylC$_{2-6}$alkynyl, —NR$^{19}$R$^{20}$ where R$^{19}$ and R$^{20}$ may be the same or different and are hydrogen, C$_{1-8}$alkyl, cyanoC$_{1-8}$alkyl, hydroxyC$_{1-8}$alkyl, haloC$_{1-8}$alkyl, C$_{3-7}$cycloalkyl, C$_{1-8}$alkylC$_{3-7}$cycloalkyl, C$_{2-6}$alkenyl, C$_{3-7}$cycloalkylC$_{1-8}$alkyl, C$_{2-6}$alkynyl, C$_{6-14}$aryl, C$_{6-14}$arylC$_{1-8}$alkyl, heterocycleC$_{1-8}$alkyl, C$_{1-8}$alkylcarbonyl, C$_{6-14}$arylsulfonyl, or R$^{19}$R$^{20}$ together with the N atom to which they are attached form a 3, 4, 5 or 6 membered heterocyclic ring, OR$^{21}$ where R$^{21}$ is hydrogen, C$_{1-8}$alkyl, C$_{3-7}$cycloalkyl, or C$_{6-14}$aryl, or SR$^{22}$ where R$^{22}$ is hydrogen, C$_{1-8}$alkyl, hydroxyC$_{1-8}$alkyl, C$_{3-7}$cycloalkyl, or C$_{6-14}$aryl;

R$^2$ is hydrogen or halogen;

R$^3$ and R$^4$ are the same or different and are hydrogen, halogen, C$_{1-8}$alkyl, C$_{6-14}$aryl, heterocycleC$_{6-14}$aryl, C$_{1-8}$alkoxy, haloC$_{1-8}$alkyl or —SR$^{24}$ where R$^{24}$ is hydrogen, C$_{1-8}$alkyl, C$_{6-14}$aryl, or C$_{6-14}$arylC$_{1-8}$alkyl;

R$^5$ is hydrogen, C$_{1-8}$alkyl, haloC$_{1-8}$alkyl, or C$_{1-8}$alkoxy;

R$^6$ is hydrogen, hydroxy, halogen, C$_{1-8}$alkyl, hydroxyC$_{1-8}$alkyl, haloC$_{1-8}$alkyl, or C$_{1-8}$alkoxy;

R$^7$ is hydrogen, hydroxy, halogen, C$_{1-8}$alkyl, hydroxyC$_{1-8}$alkyl, haloC$_{1-8}$alkyl, C$_{1-8}$alkoxy, or R$^6$ and R$^7$ together form a ketone or alkene;

R$^8$–R$^{11}$ are the same or different and are hydrogen, hydroxy, halogen, C$_{2-8}$alkyl, hydroxyC$_{1-8}$alkyl, haloC$_{1-8}$alkyl, C$_{1-8}$alkoxy, or any of R$^8$ and R$^9$ or R$^{10}$ and R$^{11}$ together form a ketone or alkene;

or a pharmaceutically acceptable derivative thereof, provided that a compound of formula (III) is not 2,5-dimethyl-1-(2,3,4-tri-O-acetyl-beta-D-xylopyranosyl)-1H-benzimidazole or 5,6-dimethyl-1-(2,3,4-tri-O-acetyl-beta-D-arabinopyranosyl)-benzimidazole-2-thione;

further provided that:
a) R$^2$, R$^3$, and R$^4$ are not all hydrogen; and
b) R$^1$ is not NR$^{19}$R$^{20}$ where R$^{19}$ and R$^{20}$ together with the N atom to which they are attached form a 5 membered heterocyclic ring containing S.

4. A compound of Formula (I)

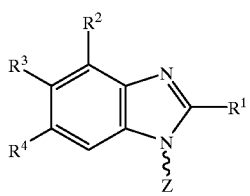

(I)

wherein Z is a substituent of Formula (Ia) or (Ib)

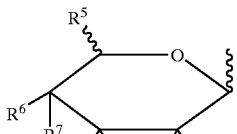

(Ia)

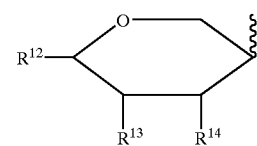

(Ib)

and wherein R$^1$ is halogen; R$^2$ is hydrogen; R$^3$ and R$^4$ are halogen; R$^5$ and R$^7$ are hydrogen; R$^6$ is hydroxy or hydrogen; R$^8$ and R$^{10}$ are hydroxy; R$^9$ and R$^{11}$ are hydrogen; R$^{12}$ is hydrogen, C$_{1-8}$alkyl, or hydroxyC$_{1-8}$ alkyl; R$^{13}$ is hydroxy; R$^{14}$ is hydrogen or hydroxy; or a pharmaceutically acceptable derivative thereof.

5. A compound of Formula (II)

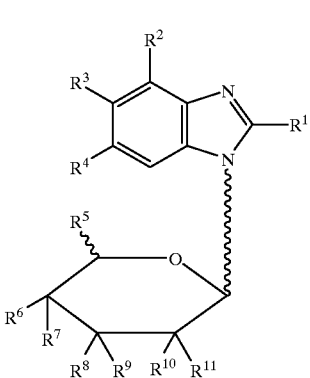

(II)

wherein R$^1$ is halogen; R$^2$ is hydrogen; R$^3$ and R$^4$ are halogen; R$^5$ and R$^7$ are hydrogen; R$^6$ is hydroxy or hydrogen; R$^8$ and R$^{10}$ are hydroxy; R$^9$ and R$^{11}$ are hydrogen; or a pharmaceutically acceptable derivative thereof.

6. A compound of formula (III)

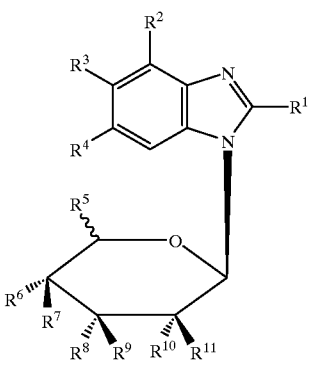

(III)

wherein $R^1$ is halogen; $R^2$ is hydrogen; $R^3$ and $R^4$ are halogen; $R^5$ and $R^7$ are hydrogen; $R^6$ is hydroxy or hydrogen; $R^8$ and $R^{10}$ are hydroxy; $R^9$ and $R^{11}$ are hydrogen; or a pharmaceutically acceptable derivative thereof.

7. A compound selected from the group consisting of
(3S,4R,5R,6S)-2-Bromo-5,6-dichloro-1-(tetrahydro-4,5-dihydroxy-6-(hydroxymethyl)-2H-pyran-3-yl)-1H-benzimidazole;
(±)-Trans-2-(2-bromo-5,6-dichloro-1H-benzimidazol-1-yl) cyclohexanol;
(±)-(1R*,2S*,3R*)-3-(2-Bromo-5,6-dichloro-1H-benzimidazol-1-yl)-1,2-cyclohexanediol;
2-bromo-5,6-dichloro-1-β-D-ribopyranosyl-1H-benzimidazole;
5,6-dichloro-N-(1-methylethyl)-1-β-D-ribopyranosyl-1H-benzimidazol-2-amine;
2-bromo-5,6-dichloro-4-fluoro-1-β-D-ribopyranosyl-1H-benzimidazole;
2-bromo-5,6,-dichloro-1-(2,3,4-tri-O-acetyl-β-D-ribopyranosyl)-1H-benzimidazole;
2-bromo-5,6-dichloro-1-β-L-ribopyranosyl-1H-benzimidazole;
2-bromo-6-chloro-5-methyl-1-β-D-ribopyranosyl-1H-benzimidazole; and
2-bromo-5,6,-dichloro-1-(4-deoxy-β-D-erythro-pentopyranosyl)-1H-benzimidazole;
and pharmaceutically acceptable derivatives thereof.

8. A pharmaceutical composition comprising a compound as defined in claim 1 together with a pharmaceutically acceptable carrier therefor.

9. A method of treatment of a herpes virus infection in an animal which comprises administering to said animal a therapeutically effective amount of a compound as defined according to claim 1.

10. A method according to claim 9 wherein the herpes virus infection is a cytomegalovirus infection.

11. A compound of formula (X):

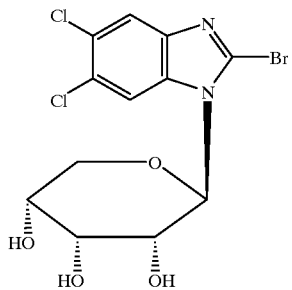

(XI)

or a pharmaceutically acceptable derivative thereof.

12. 2-Bromo-5,6-dichloro-1-β-D-ribopyranosyl-1H-benzimidazole.

13. A pharmaceutically acceptable derivative of a compound according to claim 12.

14. A pharmaceutical formulation comprising 2-bromo-5,6-dichloro-1-β-D-ribopyranosyl-1H-benzimidazole together with a pharmaceutically acceptable carrier therefor.

15. A method of treatment or prevention of the symptoms or effects of a herpes virus infection in an infected animal which comprises administering to said animal a therapeutically effective amount of a compound as defined according to claim 11.

16. A method according to claim 15 wherein the herpes virus infection is a cytomegalovirus infection.

17. A method for preventing or treating restenosis following surgical techniques comprising administering to a subject in need thereof a therapeutically effective amount of a compound of claim 1.

18. A pharmaceutical formulation comprising a pharmaceutically acceptable derivative of 2-bromo-5,6-dichloro-1-β-D-ribopyranosyl-1H-benzimidazole together with a pharmaceutically acceptable carrier therefor.

19. A method of treatment of a Hepatitis B virus infection in an animal which comprises administering to said animal a therapeutically effective amount of a compound as defined according to claim 1.

20. The method according to claim 9 wherein the herpes virus infection is selected from the group consisting of cytomegalovirus, herpes simplex virus 1, herpes simplex virus 2, varacella zoster virus, Epstein Barr virus, human herpes virus 6, human herpes virus 7 and human herpes virus 8.

21. The method according to claim 9 wherein the herpes virus infection is Epstein Barr Virus.

22. The method according to claim 15 wherein the herpes virus infection is selected from the group consisting of cytomegalovirus, herpes simplex virus 1, herpes simplex virus 2, varacella zoster virus, Epstein Barr virus, human herpes virus 6, human herpes virus 7 and human herpes virus 8.

23. The method according to claim 15 wherein the herpes virus infection is Epstein Barr Virus.

24. A pharmaceutical formulation comprising a pharmaceutically acceptable derivative of 2-bromo-5,6-dichloro-1-β-D-ribopyranosyl-1H-benzimidazole together with a pharmaceutically acceptable carrier therefor.

25. A method of treatment of a Hepatitis B virus infection in an animal which comprises administering to said animal a therapeutically effective amount of a compound as defined according to claim 1.

26. The method according to claim 9 wherein the herpes virus infection is selected from the group consisting of cytomegalovirus, herpes simplex virus 1, herpes simplex virus 2, varacella zoster virus, Epstein Barr virus, human herpes virus 6, human herpes virus 7 and human herpes virus 8.

27. The method according to claim 9 wherein the herpes virus infection is Epstein Barr Virus.

28. The method according to claim 15 wherein the herpes virus infection is selected from the group consisting of cytomegalovirus, herpes simplex virus 1, herpes simplex virus 2, varacella zoster virus, Epstein Barr virus, human herpes virus 6, human herpes virus 7 and human herpes virus 8.

29. The method according to claim 15 wherein the herpes virus infection is Epstein Barr Virus.

* * * * *

UNITED STATES PATENT AND TRADEMARK OFFICE
CERTIFICATE OF CORRECTION

PATENT NO.     : 6,455,507 B1
DATED          : September 24, 2002
INVENTOR(S)    : John C. Drach et al.

It is certified that error appears in the above-identified patent and that said Letters Patent is hereby corrected as shown below:

<u>Title page,</u>
Item [73], Assignees, should read as follows:
-- SmithKline Beecham Corporation
Philadelphia, PA (US)
The Regents of the University of Michigan
Ann Arbor, MI (US) --

<u>Column 72,</u>
Lines 34-58, delete claims 24-29.

Signed and Sealed this

Second Day of September, 2003

JAMES E. ROGAN
*Director of the United States Patent and Trademark Office*